United States Patent [19]

Branca et al.

[11] Patent Number: 5,393,875

[45] Date of Patent: Feb. 28, 1995

[54] AMINO ACID DERIVATIVES HAVING RENIN INHIBITING ACTIVITY

[75] Inventors: Quirico Branca, Basel, Switzerland; Marie-Paule Heitz; Werner Neidhart, both of Bartenheim, France; Heinz Stadler, Rheinfelden; Eric Vieira, Basel, both of Switzerland; Wolfgang Wostl, Grenzach-Wyhlen, Germany

[73] Assignee: Hoffmann-La Roche Inc., Nutley, N.J.

[21] Appl. No.: 100,959

[22] Filed: Aug. 3, 1993

Related U.S. Application Data

[63] Continuation of Ser. No. 868,054, Apr. 13, 1992, abandoned.

[30] Foreign Application Priority Data

Apr. 17, 1991 [CH] Switzerland ............ 1146/91
Feb. 20, 1992 [CH] Switzerland ............ 523/92

[51] Int. Cl.⁶ ............ C07C 317/44; A61K 37/00; A61K 31/415; C07D 295/12
[52] U.S. Cl. ............ 536/17.2; 536/18.7; 548/315.1; 548/314.7; 548/311.1; 548/331.5; 548/338.5; 548/365.7; 548/364.1; 548/375.1
[58] Field of Search ............ 536/17.2, 18.7; 514/400, 616; 548/335, 344

[56] References Cited

U.S. PATENT DOCUMENTS 4,902,706  2/1990  Hanson et al. ............ 514/400
5,134,123  7/1992  Branca et al. ............ 514/616

FOREIGN PATENT DOCUMENTS 0189203  7/1986  European Pat. Off. .
0229667  7/1987  European Pat. Off. .
0230266  7/1987  European Pat. Off. .
WO8704349  7/1987  European Pat. Off. .
0309766  4/1989  European Pat. Off. .
0309841  4/1989  European Pat. Off. .
0332008  9/1989  European Pat. Off. .
0377139  7/1990  European Pat. Off. .
0416373  3/1991  European Pat. Off. .

OTHER PUBLICATIONS

English Abstract of EP# 0 309 841.
Burger, *Medicinal Chemistry*, 1960, pp. 565-571, 578-581, 600 & 601.
Plattner et al., *J. Med. Chem.*, 1988, 31(12), pp. 2277-2288.
Denkewalter et al., *Progress in Drug Research*, 1966, vol. 10, pp. 510-512.
Haber et al., *J. Cardiovasc. Pharmacol.*, 1987, 10 (Supp. 7), pp. S54–S58.
Bolis et al., *J. Med. Chem.*, 1987, 30 (10), pp. 1729-1737.

Primary Examiner—Ronald W. Griffin
Attorney, Agent, or Firm—George M. Gould; William H. Epstein; Bruce A. Pokras

[57] ABSTRACT

The compounds of the formula

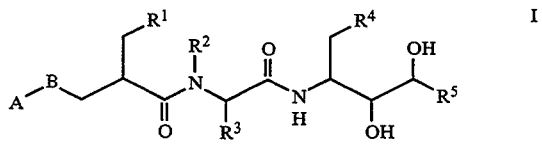

wherein A, $R^1$, $R^2$, $R^3$, $R^4$ and $R^5$ have the significance given in claim 1, in the form of optically pure diastereomers, mixtures of diastereomers, diastereomeric racemates or mixtures of diastereomeric racemates as well as pharmaceutically usable salts thereof inhibit the activity of the natural enzyme renin and can accordingly be used in the form of pharamaceutical preparations in the control or prevention of high blood pressure and cardiac insufficiency. They can be manufactured according to various methods which are known per se.

26 Claims, No Drawings

AMINO ACID DERIVATIVES HAVING RENIN INHIBITING ACTIVITY

This is a continuation of application Ser. No. 07/868,054, filed Apr. 13, 1992, now abandoned.

SUMMARY OF THE INVENTION

The present invention is concerned with amino acid derivatives. In particular, it is concerned with amino acid derivatives of the formula:

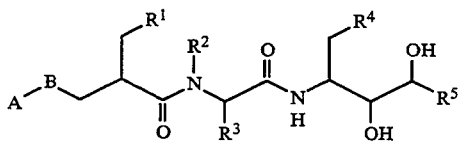

wherein $R^1$ is cycloalkyl, phenyl, substituted phenyl, naphthyl, thienyl, pyridyl, quinolyl, isoquinolyl or benzyl, $R^2$ is hydrogen or methyl, $R^3$ is hydrogen, hydroxy, alkyl, alkoxy, alkenyloxy, alkylthio, alkylthioalkyl or alkoxycarbonyl, or imidazol-1-ylmethyl, imidazol-2-ylmethyl or imidazol-4-ylmethyl, each of which can be methylated on a carbon atom and/or nitrogen atom, 2-aminoimidazol-4-ylmethyl, 5-iodoimidazol-4-ylmethyl, pyrazol-1-ylmethyl, pyrazol-3-ylmethyl, thiazol-2-ylmethyl, thiazol-4-ylmethyl, thiazol-5-ylmethyl, 2-aminothiazol-4ylmethyl, thienylmethyl, furanylmethyl, pyridylmethyl, aminocarbonyl, aminocarbonylalkyl or alkoxycarbonylalkyl, $R^4$ is cycloalkyl, substituted cycloalkyl, phenyl or halophenyl, $R^5$ is cycloalkyl, cycloalkylalkyl or alkyl, B is a sulphur atom or a sulfinyl or sulfonyl group and A is the group

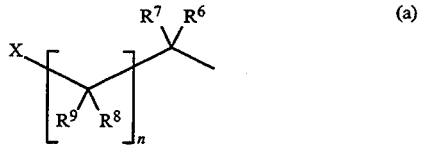

in which $R^6$, $R^7$ and $R^8$ each independently are hydrogen or alkyl, $R^9$ is hydrogen, alkyl, hydroxyalkyl, amino, alkoxycarbonylamino or benzyloxycarbonylamino, n is the integer zero or one and X is the group Y—CO— or, where n is the integer one, also the group Z—O—, wherein Y is cycloalkylamino, sulphoalkylamino or bisalkoxyalkylamino, or pyridylalkylamino or morpholinoalkylamino, each of which can be substituted at the amino group by alkyl; pyrazinylalkylamino, which can be substituted at the nitrogen atom and/or at the amino group by alkyl; 4-piperidinylalkylamino, which can be substituted at the nitrogen atom by alkyl, benzyl, benzyloxycarbonyl, alkoxycarbonyl or hydroxyalkyl and/or at the amino group by alkyl; alkoxycarbonylalkylamino, hydroxyalkoxyalkylamino, hydroxyalkylamino, bishydroxyalkylamino, the group $(R^a)(R^b)N-$ in which $R^1$ and $R^b$ each independently are hydrogen or alkyl or together with the nitrogen atom to which they are attached are a saturated 5- or 6-membered heterocyclic ring which can contain an additional nitrogen atom or an oxygen or sulphur atom as a further hetero atom or can carry an oxo group, whereby the sulphur atom can also be present in the form of a sulfinyl or sulfonyl group, or which can be substituted on one or two carbon atoms by alkyl, hydroxy, hydroxyalkyl or alkoxyalkoxy or on a second nitrogen atom which may be present by alkyl, benzyl, benzyloxycarbonyl, alkoxycarbonyl or hydroxyalkyl, or in which the optionally present second nitrogen atom can carry an oxygen atom, alkoxyalkoxyalkoxy, cycloalkylalkoxy, 1,3-dimethyldioxolan-2-ylalkoxy, the group $(R^a)(R^b)N-$alkoxy, the residue of a natural aminodesoxy sugar or, where $R^9$ is different from hydrogen or alkyl, also alkoxy and Z is $C_5-C_{17}$-alkylcarbonyl, benzoyl, alkoxyalkylcarbonyl, cycloalkylcarbonyl, aminoalkylcarbonyl which can be substituted at the nitrogen atom by alkoxycarbonyl or benzyloxycarbonyl, alkylaminocarbonyl, phenylaminocarbonyl or, where $R^9$ is different from hydrogen or alkyl, also hydrogen,
in the form of optically pure diastereomers, mixtures of diastereomers, diastereomeric racemates or mixtures of diastereomeric racemates as well as pharmaceutically usable salts of these compounds.

These compounds are novel and are distinguished by valuable pharmacodynamic properties.

Objects of the present invention are the compounds of the invention and their pharmaceutically usable salts per se and for use as therapeutically active substances, the manufacture of these compounds, medicaments containing these and the manufacture of such medicaments as well as the use of compounds of the invention and their pharmaceutically usable salts in the control or prevention of illnesses or in the improvement of health, especially in the control or prevention of high blood pressure and cardiac insufficiency.

DETAILED DESCRIPTION OF THE INVENTION

The following definitions of the general terms used in the present description apply irrespective of whether the terms in question appear alone or in combination.

The term "cycloalkyl" used in the present description signifies saturated, cyclic hydrocarbon residues with 3–6 carbon atoms, i.e., cyclopropyl, cyclobutyl, cyclopentyl and cyclohexyl. The term "substituted phenyl" denotes phenyl mono- or multiply-substituted by alkyl, alkoxy, alkylcarbonyloxy, hydroxy, halogen or trifluoromethyl, such as 4-hydroxyphenyl, 4-methoxyphenyl, 4-methylphenyl, 4-chlorophenyl and the like. The term "alkyl" signifies straight-chain and branched, saturated hydrocarbon residues with 1–6, preferably 1–4, carbon atoms such as methyl, ethyl, n-propyl, isopropyl, n-butyl, isobutyl, sec.-butyl, tert-butyl, pentyl, hexyl and the like. The term "alkoxy" signifies alkyl ether groups in which the term "alkyl" has the above significance, such as methoxy, ethoxy, propoxy, isopropoxy, butoxy, isobutoxy, sec.-butoxy, tert-butoxy and the like. The term "alkenyloxy" relates to an unsaturated hydrocarbon residue with 3–6 carbon atoms which is attached via an oxygen atom, such as allyloxy and the like. The term "substituted cycloalkyl" signifies cycloalkyl mono- or multiply-substituted by alkyl, hydroxy or halogen, whereby the term "cycloalkyl" has the above significance, such as 4-hydroxycyclohexyl, 4-fluorocyclohexyl, 4,4-difluorocyclohexyl and the like.

The term "bisalkoxyalkylamino" or "bishydroxyalkylamino" defines an amino group which at the nitrogen atom is either disubstituted by two alkoxyalkyl or hydroxyalkyl residues or is monosubstituted by a dialkoxyalkyl or dihydroxyalkyl residue. Examples of such groups are bis(dimethoxyethyl)amino, 1-hydroxy-2-hydroxymethyl-2-propylamino and the like.

Pyrrolidinyl, piperidinyl, piperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl, 2,6-dimethylmorpholinyl and the like are examples of saturated 5- and 6-membered heterocyclic rings. Glucosamine, mannosamine, galactosamine and the like are examples of natural aminodesoxy sugars.

The term "pharmaceutically usable salts" embraces salts of inorganic or organic acids such as hydrochloric acid, hydrobromic acid, nitric acid, sulphuric acid, phosphoric acid, citric acid, o formic acid, maleic acid, acetic acid, succinic acid, tartaric acid, methanesulphonic acid, p-toluenesulphonic acid and the like or, where Y signifies sulphoalkylamino, also of inorganic or organic bases such as sodium or potassium hydroxide, ammonia, triethylamine, diisopropylethylamine, pyridine and the like. Such salts can be manufactured readily by any person skilled in the art having regard to the state of the art and taking into consideration the nature of the compound to be converted into a salt.

The compounds of the invention have at least four asymmetric carbon atoms and are therefore present in the form of optically pure diastereomers, mixtures of diastereomers, diastereomeric racemates or mixtures of diastereomeric racemates. The present invention embraces all forms. Mixtures of diastereomers, diastereomeric racemates or mixtures of diastereomeric racemates can be separated according to usual methods, e.g., by column chromatography, thin-layer chromatography, HPLC and the like.

The invention comprises amino acid derivatives of the formula:

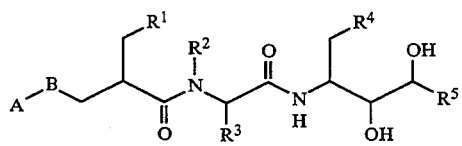

I wherein $R^1$ is cycloalkyl, phenyl, substituted phenyl, naphthyl, thienyl, pyridyl, quinolyl, isoquinolyl or benzyl, $R^2$ is hydrogen or methyl, $R^3$ is hydrogen, hydroxy, alkyl, alkoxy, alkenyloxy, alkylthio, alkylthioalkyl or alkoxycarbonyl, or imidazol-1-ylmethyl, imidazol-2-ylmethyl or imidazol-4-ylmethyl, each of which can be methylated on a carbon atom and/or nitrogen atom, 2-aminoimidazol-4-ylmethyl, 5-iodoimidazol-4-ylmethyl, pyrazol-1-ylmethyl, pyrazol-3-ylmethyl, thiazol-2-ylmethyl, thiazol-4-ylmethyl, thiazol-5-ylmethyl, 2-aminothiazol-4-ylmethyl, thienylmethyl, furanylmethyl, pyridylmethyl, aminocarbonyl, aminocarbonylalkyl or alkoxycarbonylalkyl, $R^4$ is cycloalkyl, substituted cycloalkyl, phenyl or halophenyl, $R^5$ is cycloalkyl, cycloalkylalkyl or alkyl, B is a sulphur atom or a sulfinyl or sulfonyl group and A is the group

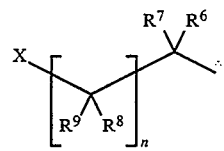

(a)

in which $R^6$, $R^7$ and $R^8$ each independently are hydrogen or alkyl, $R^9$ is hydrogen, alkyl, hydroxyalkyl, amino, alkoxycarbonylamino or benzyloxycarbonylamino, n is the integer zero or one and X is the group Y—CO— or, where n is the integer one, also the group Z—O—, wherein Y is cycloalkylamino, sulphoalkylamino or bisalkoxyalkylamino, or pyridylalkylamino or morpholinoalkylamino, each of which can be substituted at the amino group by alkyl; pyrazinylalkylamino, which can be substituted at the nitrogen atom and/or at the amino group by alkyl; 4-piperidinylalkylamino, which can be substituted at the nitrogen atom by alkyl, benzyl, benzyloxycarbonyl, alkoxycarbonyl or hydroxyalkyl and/or at the amino group by alkyl; alkoxycarbonylalkylamino, hydroxyalkoxyalkylamino, hydroxyalkylamino, bishydroxyalkylamino, the group $(R^a)(R^b)N-$ in which $R^a$ and $R^b$ each independently are hydrogen or alkyl or together with the nitrogen atom to which they are attached are a saturated 5- or 6-membered heterocyclic ring which can contain an additional nitrogen atom or an oxygen or sulphur atom as a further hetero atom or can carry an oxo group, whereby the sulphur atom can also be present in the form of a sulfinyl or sulfonyl group, or which can be substituted on one or two carbon atoms by alkyl, hydroxy, hydroxyalkyl or alkoxyalkoxy or on a second nitrogen atom which may be present by alkyl, benzyl, benzyloxycarbonyl, alkoxycarbonyl or hydroxyalkyl, or in which the optionally present second nitrogen atom can carry an oxygen atom, alkoxyalkoxyalkoxy, cycloalkylalkoxy, 1,3-dimethyldioxolan-2-ylalkoxy, the group $(R^a)(R^b)N$-alkoxy, the residue of a natural aminodesoxy sugar or, where $R^9$ is different from hydrogen or alkyl, also alkoxy and Z is $C_5$–$C_{17}$-alkylcarbonyl, benzoyl, alkoxyalkylcarbonyl, cycloalkylcarbonyl, aminoalkylcarbonyl which can be substituted at the nitrogen atom by alkoxycarbonyl or benzyloxycarbonyl, alkylaminocarbonyl, phenylaminocarbonyl or, where $R^9$ is different from hydrogen or alkyl, also hydrogen, in the form of optically pure diastereomers, mixtures of diastereomers, diastereomeric racemates or mixtures of diastereomeric racemates as well as pharmaceutically usable salts of these compounds.

In particular, the invention comprises amino acid derivatives of formula I wherein Z is alkoxyalkylcarbonyl, cycloalkylcarbonyl, aminoalkylcarbonyl which can be substituted at the nitrogen atom by alkoxycarbonyl or benzyloxycarbonyl, or alkylaminocarbonyl, and all other groups are as above.

Especially, the invention comprises amino acid derivatives of formula I wherein Z is $C_1$–$C_4$-alkoxy-$C_1$–$C_4$-alkylcarbonyl, cyclopropylcarbonyl, tert-butoxycarbonylamino-$C_1$–$C_4$-alkylcarbonyl, benzyloxycarbonylamino-$C_1$–$C_4$-alkylcarbonyl or $C_1$–$C_4$-alkylaminocarbonyl, and all other groups are as above.

The invention also comprises compounds of formula I in which $R^1$ is cycloalkyl, phenyl, substituted phenyl, naphthyl, thienyl, pyridyl, quinolyl, isoquinolyl or benzyl, $R^2$ is hydrogen or methyl, $R^3$ is hydrogen, hydroxy, alkyl, alkoxy, alkenyloxy, alkylthio, alkylthioalkyl or alkoxycarbonyl, or imidazol-2-ylmethyl or imidazol-4-yl-methyl, each of which can be methylated on a carbon atom and/or nitrogen atom, 2-aminoimidazol-4-ylmethyl, 5-iodoimidazol-4-ylmethyl, thiazol-4-ylmethyl, thienylmethyl, furanylmethyl, pyridylmethyl, aminocarbonyl, aminocarbonylalkyl or alkoxycarbonylalkyl, $R^4$ is cycloalkyl, substituted cycloalkyl, phenyl or halophenyl, $R^5$ is cycloalkyl, cycloalkylalkyl or alkyl, B is a sulphur atom or a sulfinyl or sulfonyl group, $R^6$, $R^7$ and $R^8$ each independently are hydrogen or alkyl, $R^9$ is hydrogen, alkyl, hydroxyalkyl, amino, alkoxycarbonylamino or benzyloxycarbonylamino, n is the integer zero or one and X is the group Y—CO— or, where n is the integer one, also the group Z—O—, wherein Y is cycloalkylamino, sulphoalkylamino, bisalkoxyalkylamino or pyridylalkylamino, or 4-piperidinylalkylamino which can be substituted at the nitrogen atom by alkyl, benzyl, benzyloxycarbonyl, alkoxycarbonyl or hydroxyalkyl; alkoxycarbonylalkylamino, hydroxyalkylamino, bishydroxyalkylamino, the group $(R^a)(R^b)N$- in which $R^a$ and $R^b$ each independently are hydrogen or alkyl or together with the nitrogen atom to which they are attached are a saturated 5- or 6-membered heterocyclic ring which can contain an additional nitrogen atom or an oxygen or sulphur atom as a further hetero atom, whereby the sulphur atom can also be present in the form of a sulfinyl or sulfonyl group, which can be substituted on one or two carbon atoms by alkyl, hydroxy, hydroxyalkyl or alkoxyalkoxy on a second nitrogen atom which may be present by alkyl, benzyl, benzyloxycarbonyl, alkoxycarbonyl or hydroxyalkyl or which can carry an oxo group, alkoxyalkoxyalkoxy, cycloalkylalkoxy, 1,3-dimethyldioxolan-2-ylalkoxy, the group $(R^a)(R^b)$N-alkoxy, the residue of a natural aminodesoxy sugar or, where $R^9$ is different from hydrogen or alkyl, also alkoxy and Z is $C_5$-$C_{17}$-alkylcarbonyl, benzoyl, alkoxyalkylcarbonyl, cycloalkylcarbonyl, aminoalkylcarbonyl, which can be substituted at the nitrogen atom by alkoxycarbonyl or benzyloxycarbonyl, alkylaminocarbonyl, phenylaminocarbonyl or, where $R^9$ is different from hydrogen or alkyl, also hydrogen.

The invention also comprises compounds of formula I wherein $R^1$ is cycloalkyl, phenyl, substituted phenyl, naphthyl, thienyl or pyridyl, $R^2$ is hydrogen, $R^3$ is hydrogen, hydroxy, alkyl, alkoxy, allyloxy, alkythio, alkylthiomethyl, alkoxycarbonyl, imidazol-1-ylmethyl, imidazol-4-ylmethyl, 2-aminoimidazol-4-ylmethyl, 5-iodoimidazol-4-ylmethyl, pyrazol-1-ylmethyl, thiazol-4-ylmethyl, thien-2-ylmethyl, furan-2-ylmethyl, pyridylmethyl or aminocarbonyl, $R^4$ is cycloalkyl or phenyl, $R^5$ is cycloalkyl or alkyl, B is sulfonyl, $R^6$ and $R^7$ each are hydrogen or $C_1$-$C_4$-alkyl, Y is cycloalkylamino, sulphoalkylamino or bisalkoxyalkylamino, or pyridylalkylamino, which can be substituted at the amino group by alkyl; 4-piperidinylalkylamino, which can be substituted at the nitrogen atom by alkyl, benzyl, benzyloxycarbonyl, alkoxycarbonyl or hydroxyalkyl; alkoxycarbonylalkylamino, hydroxyalkylamino, bishydroxyalkylamino or the group $(R^a)(R^b)$N- in which $R^a$ and $R^b$ each independently are hydrogen or alkyl or together with the nitrogen atom to which they are attached are a saturated 5- or 6-membered heterocyclic ring which can contain an additional nitrogen atom or an oxygen or sulphur atom or can carry an oxo group, whereby the sulphur atom can also be present in the form of a sulfinyl or sulfonyl group, or which can be substituted on one or two carbon atoms by alkyl, hydroxy, hydroxyalkyl or alkoxyalkoxy or on a second nitrogen atom which may be present by alkyl, benzyl, benzyloxycarbonyl, alkoxycarbonyl or hydroxyalkyl, and n is the integer zero.

The invention also comprises amino acid derivatives of formula I wherein $R^1$ is cyclohexyl, phenyl, napthyl or thienyl, $R^2$ is hydrogen, $R^3$ is hydrogen, hydroxy, $C_1$-$C_4$-alkyl, $C_1$-$C_4$-alkoxy, allyloxy, $C_1$-$C_4$-alkylthio, $C_1$-$C_4$-alkylthiomethyl, $C_1$-$C_4$-alkoxycarbonyl, imidazol-4-ylmethyl, thiazol-4-ylmethyl or pyridylmethyl, $R^4$ is cyclohexyl, $R^5$ is cyclopropyl, isopropyl or isobutyl, B is sulfonyl, $R^6$ and $R^7$ each are methyl, n is the integer zero and Y is the group $(R^a)(R^b)$N-.

The invention also comprises compounds of formula I in which $R^1$ is phenyl, $R^2$ is hydrogen, $R^3$ is imidazol-4-ylmethyl or 3-pyridylmethyl, $R^4$ is cyclohexyl, $R^5$ is cyclopropyl, B is sulfonyl, $R^6$ and $R^7$ each are methyl, n is the integer zero and Y is pyrrolidinyl, piperidinyl, piperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4-oxopiperidinyl, 3,5-dimethylmorpholinyl, 4,4-dioxothiomorpholinyl, 4-oxothiomorpholinyl or 2,6-dimethylmorpholinyl.

The invention also comprises compounds of formula I in which $R^1$ is phenyl, $R^2$ is hydrogen, $R^3$ is imidazol-4-ylmethyl or pyridylmethyl, R4 is cyclohexyl, $R^5$ is cyclopropyl, B is sulfonyl, $R^6$ and $R^7$ each are methyl, n is the integer zero and Y is morpholinyl.

The invention also comprises compounds of formula I wherein $R^1$ is cycloalkyl, phenyl, substituted phenyl, naphthyl, thienyl or pyridyl, $R^2$ is hydrogen, $R^3$ is hydrogen, hydroxy, alkyl, alkoxy, allyloxy, alkythio, alkylthiomethyl, alkoxycarbonyl, imidazol- 1-ylmethyl, imidazol-4-ylmethyl, 2-aminoimidazol-4-ylmethyl, 5-iodoimidazol-4-ylmethyl, pyrazol-1-ylmethyl, thiazol-4-ylmethyl, thien-2-ylmethyl, furan-2-ylmethyl, pyridylmethyl or aminocarbonyl, R4 is cycloalkyl or phenyl, $R^5$ is cycloalkyl or alkyl, B is sulfonyl, $R^6$ and $R^7$ each are hydrogen or $C_1$-$C_4$-alkyl, and X is the group Y—CO— wherein Y is 4-piperidinylamino which can be substituted at the nitrogen atom by alkyl, benzyl, benzyloxycarbonyl, alkoxycarbonyl or hydroxyalkyl; and n is the integer zero.

Specially preferred compounds of the invention are:
(S)-N-[(1S,2R,3S)-1-(cyclohexylmethyl)-3-cyclopropyl-2,3-dihydroxypropyl]-α-[(S)-α-[[[1-[[2-hydroxy-1-(hydroxymethyl)-1-methylethyl]carbamoyl]-1-methylethyl]sulfonyl]methyl]hydrocinnamamido]imidazole-4-propionamide;

N-(tert-butoxycarbonyl)glycine 2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl ester;

cyclopropylmethyl 2-[[(R)-2-[[(S)-1-[[(1S,2R,3S)-1-(cyclohexylmethyl)-3-cyclopropyl-2,3  -dihydroxypropyl]carbamoyl]-2-imidazol-4-ylethyl]carbamoyl]-3-phenylpropyl]sulfonyl]-2-methylpropionate;

(S)-α-[(R or S)-α-[[[1-[(2-pyridylmethyl)carbamoyl]-1-methylethyl]sulfonyl]methyl]hydrocinnamamido]-N-[(1S,2R,3S)-1 -(cyclohexylmethyl)-3-cyclopropyl-2,3-dihydroxypropyl]imidazole-4-propionamide; and (S)-α-[(R or S)-α-[[[1-[(1-benzyl-4-piperidinyl)carbamoyl]1-methylethyl]sulfonyl]methyl]hydrocinnamamido[-N-[(1S,2R,3S)-1-(cyclohexylmethyl)-3-cyclopropyl-2,3-dihydroxypropyl[imidazole-4-propionamide.

Further specially preferred compounds of the invention are:

2-[2-[[(S)-2-[[(S)-1-[[(1S,2R,3S)-1-(cyclohexylmethyl)3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose;

2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl methoxyacetate;

tert-butyl [(R)-2-[[(S or R)-2-[[(S)-1-[[(1S,2R,3S)-1-(cyclohexylmethyl)-3-cyclopropyl-2,3 -dihydroxypropyl]carbamoyl]-2-imidazol-4-ylethyl]carbamoyl]-3-phenylpropyl]sulfonyl]-2-(morpholinocarbonyl)ethyl]carbamate;

(S)-α-[(R or S)-α-[[[1-[bis(2-methoxyethyl)carbamoyl]-1-methylethyl]sulfonyl]methyl]hydrocinnamamido]-N-[(1S,2R,3S)-1-(cyclohexylmethyl)-3-cyclopropyl-2,3-dihydroxypropyl]imidazole-4-propionamide;

(S)-60 -[(S or R)-α-[[[(R)-2-amino-2-(morpholinocarbonyl)ethyl]sulfonyl]methyl]hydrocinnamamido]-N-[(1S,2R,3S )-1-(cyclohexylmethyl)-3-cyclopropyl-2,3-dihydroxypropyl]imidazole-4-propionamide; and (S or R)-N-[(1S,2R,3S)-1-(cyclohexylmethyl)-3-cyclopropyl-2,3-dihydroxypropyl]-α-[(S)-α-[[[1-methyl-1-[morpholinocarbonyl[ethyl]ethyl]sulfonyl]methyl]hydrocinnamamido]-3-(thiazolyl-4-yl)propionamide.

Quite specially preferred compounds of the invention are:

tert-butyl [(S)-2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate;

(S)-N-[(1S,2R,3S)-1-(cyclohexylmethyl)-3-cyclopropyl-2,3-dihydroxypropyl]-α-[(S)-α-[[[1-(morpholinocarbonyl)-1-methylethyl]hydrocinnamamido]imadazole-4-propionamide;

(S)-N-[(1S,2R,3S)-1-(cyclohexylmethyl)-3-cyclopropyl-2,3-dihydroxypropyl]-α-[(S)-α-[[[1-[(4-hydroxypiperidino)carbonyl]1-methylethyl]sulfonyl]methyl]hydrocinnamamido]imidazole-4-propionamide; and (S or R)-N-[(1S,2R,3S)-1-(cyclohexylmethyl)-3-cyclopropyl--2,3-dihydroxypropyl]-α-[(S)-α-[[[1-methyl-1-[morpholinocarbonyl]ethyl]sulfonyl]methyl]hydrocinnamamido]-3-(pyridin-3-yl)propionamide.

Compounds of the invention in the form of optically pure diastereomers, mixtures of diasteromers, diastereomeric racemates or mixtures of diastereomeric racemates as well as pharmaceutically usable salts thereof can be manufactured by a) reacting a compound of the formula:

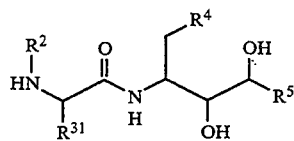

wherein $R^{31}$ is hydrogen, alkyl, alkylthioalkyl or alkoxycarbonyl, or imidazol-1-ylmethyl, imidazol-2-ylmethyl or imidazol-4-ylmethyl, each of which can be methylated on a carbon atom and/or nitrogen atom, 2-aminoimidazol-4-ylmethyl 5-iodoimidazol-4-ylmethyl, pyrazol-1-ylmethyl, pyrazol-3-ylmethyl, thiazol-2-ylmethyl, thiazol-4-ylmethyl, thiazol-5-ylmethyl, 2-aminothiazol-4-ylmethyl, thienylmethyl, furanylmethyl, pyridylmethyl, aminocarbonyl, aminocarbonylalkyl or alkoxycarbonylalkyl and $R^2$, $R^4$ and $R^5$ have the significance given above, with an acid of the formula:

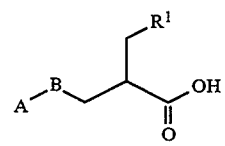

wherein A,B and $R^1$ have the significance given above, or an activated derivative thereof, or b) reacting a compound of the formula:

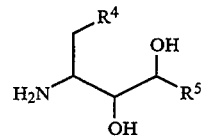

wherein $R^4$ and $R^5$ have the significance given above, with an acid of the formula:

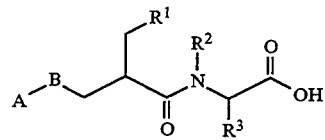

wherein A, B, $R^1$, $R^2$ and $R^3$ have the significance given above,
or an activated derivative thereof, or c) for the manufacture of a compound of the invention in which A contains free primary or secondary amino groups and/or free primary or secondary hydroxy groups, cleaving off the N- or O-protecting group(s) from a compound of the formula:

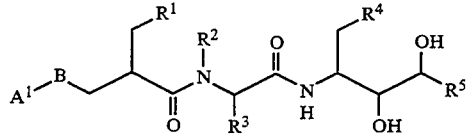

wherein $A^1$ has the same significance as A, with the proviso that A contains a N- or 0-protecting group, and d) if desired, separating a mixture of diastereomeric racemates into the diastereomeric racemates or optically pure diastereomers, and/or e) if desired, separating a mixture of diastereomers into the optically pure diastereomers, and/or f) if desired, converting a compound obtained into a pharmaceutically usable salt.

The acylation of a compound of formula II with an acid of formula III or an activated derivative thereof is effected according to methods known per se in peptide chemistry. Especially suitable acylating agents are activated derivatives such as esters, mixed esters, acid halides, acid anhydrides or mixed anhydrides. The reaction is carried out in an organic solvent or solvent mixture which is inert under the reaction conditions at a temperature between about 0° C. and room temperature. As solvents there come into consideration especially aromatic hydrocarbons such as benzene, toluene or xylene, chlorinated hydrocarbons such as methylene chloride or chloroform, ethers such as diethyl ether, tetrahydrofuran or dioxan, and the like. Furthermore, the acylation can be effected in the presence of a condensation agent such as HBTU [O-benzotriazolyl-N,N,N',N'-tetramethyluronium hexafluorophosphate, BOP [benzotriazol-1-yloxy-bis(dimethylamino)phosphonium hexafluorophosphate], BOPC [bis(2-oxo-2-oxozolidinyl)phosphine chloride], HOBT [N-hydroxybenzotriazole], DCC [dicyclohexylcarbodiimide hydrochloride], EDC [N-(3-dimethylaminopropyl)-N'-ethylcarbodiimide hydrochloride] and the like. The reaction is conveniently carried out in an organic solvent or solvent mixture which is inert under the reaction conditions at a temperature between about 0° and 50° C., preferably at about room temperature. As solvents there come into consideration especially dimethyl-formamide, methylene chloride, acetonitrile, tetrahydrofuran and the like.

The reaction of a compound of formula IV with an acid of formula V or an activated derivative thereof is also effected according to methods which are known per se in peptide chemistry, i.e. under the same conditions as given above for the acylation of a compound of formula II. Examples of suitable activated compounds of formula V are likewise acid halides, acid anhydrides, mixed anhydrides, esters, mixed esters and the like.

The cleavage of the N- or O-protecting group(s) in accordance with process variant c) is also effected according to methods known per se depending on the nature of the N- or O-protecting group to be cleaved off. However, the cleavage is conveniently effected by acidic or basic hydrolysis or by hydrogenolysis. A solution of a mineral acid such as hydrochloric acid, hydrobromic acid, sulphuric acid, phosphoric acid and the like in an inert solvent or solvent mixture is advantageously used for the acidic hydrolysis. Alcohols such as methanol or ethanol, ethers such as tetrahydrofuran or dioxan, chlorinated hydrocarbons such as methylene chloride, and the like are suitable solvents. Alkali metal hydroxides and carbonates such as potassium or sodium hydroxide or potassium or sodium carbonate, organic amines such as piperidine, and the like can be used for the basic hydrolysis. Inert organic solvents, such as those mentioned above for the acidic hydrolysis, can be used as solubilizers. The reaction temperature for the acidic and basic hydrolysis can be varied in a range of 0° C. to the reflux temperature, preferably between about 0° C. and room temperature. The tert-butoxycarbonyl residue is conveniently cleaved off with aqueous hydrochloric acid or hydrochloric acid/dioxan or with trifluoroacetic acid or formic acid in the presence or absence of an inert solvent. The benzyloxycarbonyl group can be cleaved off in a known manner by acidic hydrolysis as described above or hydrogenolitically. The cleavage of the acetal protecting group can be carried out in a known manner by aqueous-acidic hydrolysis or, for example, using iron trichloride/silica gel.

The starting materials of formula II are partly novel and partly known. These compounds can be prepared by reacting a compound of formula IV with a compound of the general formula

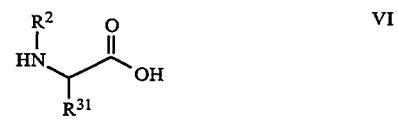

wherein $R^2$ and $R^{31}$ have the significance given above. This reaction is effected according to methods which are known in peptide chemistry, i.e. under the reaction conditions described above for the acylation of a compound of formula II.

The starting materials of formula IV are also partly novel and partly known and can be prepared by cleaving off the amino protecting group and, where applicable, simultaneously also the O-protecting group in a compound of the formula:

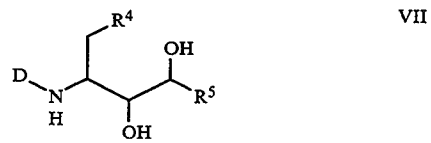

or

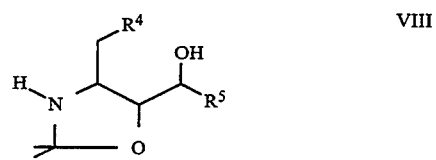

wherein D is an amino protecting group, preferably tert-butoxycarbonyl or benzyloxycarbonyl, and $R^4$ and $R^5$ have the significance given above.

The cleavage of the N-protecting group and, where applicable, the O-protecting group is also effected according to methods known per se, for example in an organic solvent or solvent mixture which is inert under the reaction conditions at a temperature between about 0° and 50° C. with an acid such as hydrochloric acid, trifluoroacetic acid, and the like. Suitable solvents are ethers such as tetrahydrofuran or dioxan, alcohols such as methanol or chlorinated hydrocarbons such as methylene chloride, and the like. Under these conditions the oxazolidine ring in a compound of formula VIII is—as already mentioned—simultaneously cleaved. Of course, if only the cleavage of the oxazolidine ring is desired, then other reaction conditions must be chosen: the reaction must be carried out at lower temperatures and in aqueous solvents or, for example, with iron trichloride/silica gel.

The compounds of formulae VII and VIII are also partly novel and partly known and can be prepared as shown by way of formulae in Reaction Scheme I hereinafter.

The compounds of formula VI are known or can be obtained in analogy to the preparation of the known compounds.

The acids of formula III and their activated derivatives are novel and are also an object of the present invention. The preparation of the acids of formula III is presented by way of formulae in Reaction Scheme II hereinafter. The activated derivatives can be prepared readily by any person skilled in the art having regard to the state of the art and taking into consideration the nature of the activated derivative.

The acids of formula V and their activated derivatives are also novel and are an object of the present invention. Those acids in which $R^3$ has the significance of $R^{31}$ can be prepared readily by reacting a corresponding acid of formula III with a compound of formula VI. The reaction is effected according to methods known per se in peptide chemistry, i.e., under the reaction conditions described above for the acylation of a compound of formula II. Those acids in which $R^3$ is hydroxy, alkoxy, alkenyloxy or alkylthio can be prepared as shown by way of formulae in Reaction Scheme III hereinafter. The activated derivative of the acids of formula V can be prepared readily by any person skilled in the art like those of the acids of formula III.

The steps which are presented in Reaction Schemes I to III are without exception reactions which are usual in synthetic chemistry, all of which are carried out according to methods known per se. The reaction of the carboxyamides of formula XXII, which are also novel and an object of the present invention, is effected according to the process described in EPA 0331921. With experimental section. The symbols $R^1$, $R^4$, $R^5$, $R^6$, $R^7$, $R^8$, $R^9$, A, B, n, Y, Z and D used in the Reaction Schemes have the significance given above, while B* is a sulphur atom or a sulfonyl group, R is alkyl or benzyl and $R^{32}$ is alkoxy, alkenyloxy or alkylthio.

The starting materials of formula IX, XIII, XIV and XV used in the Reaction Schemes are known or can be obtained in analogy to preparation of the known compounds.

Scheme I

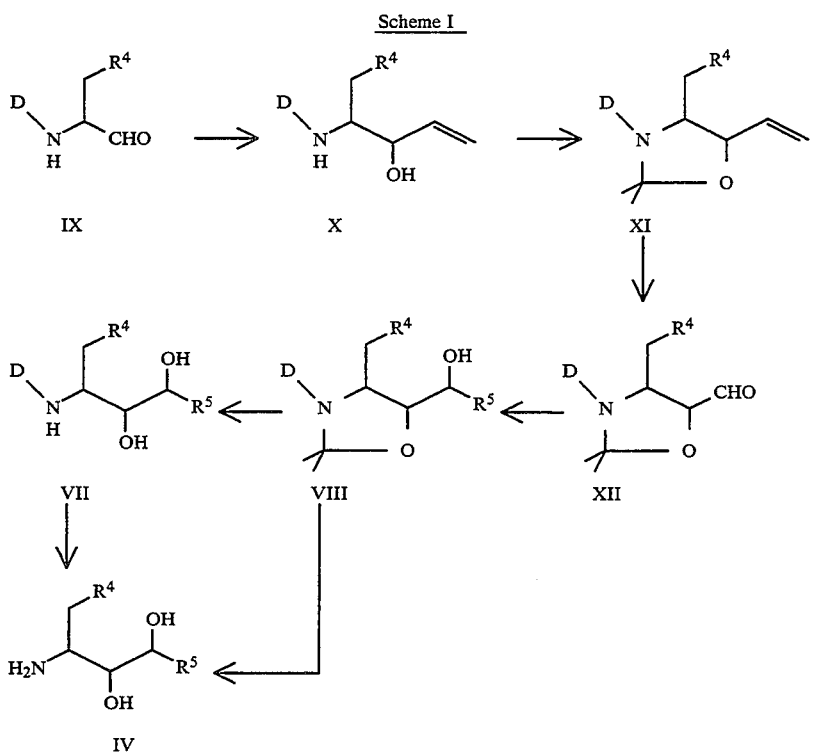

Scheme II

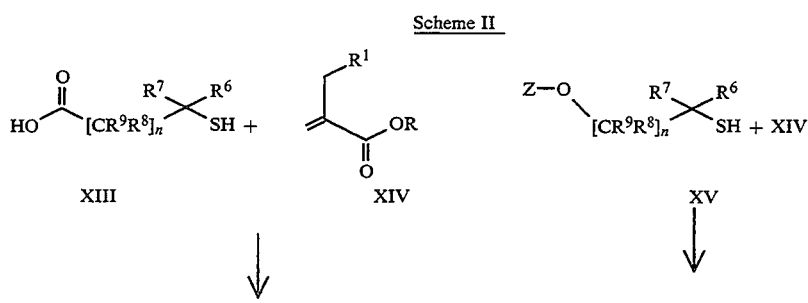

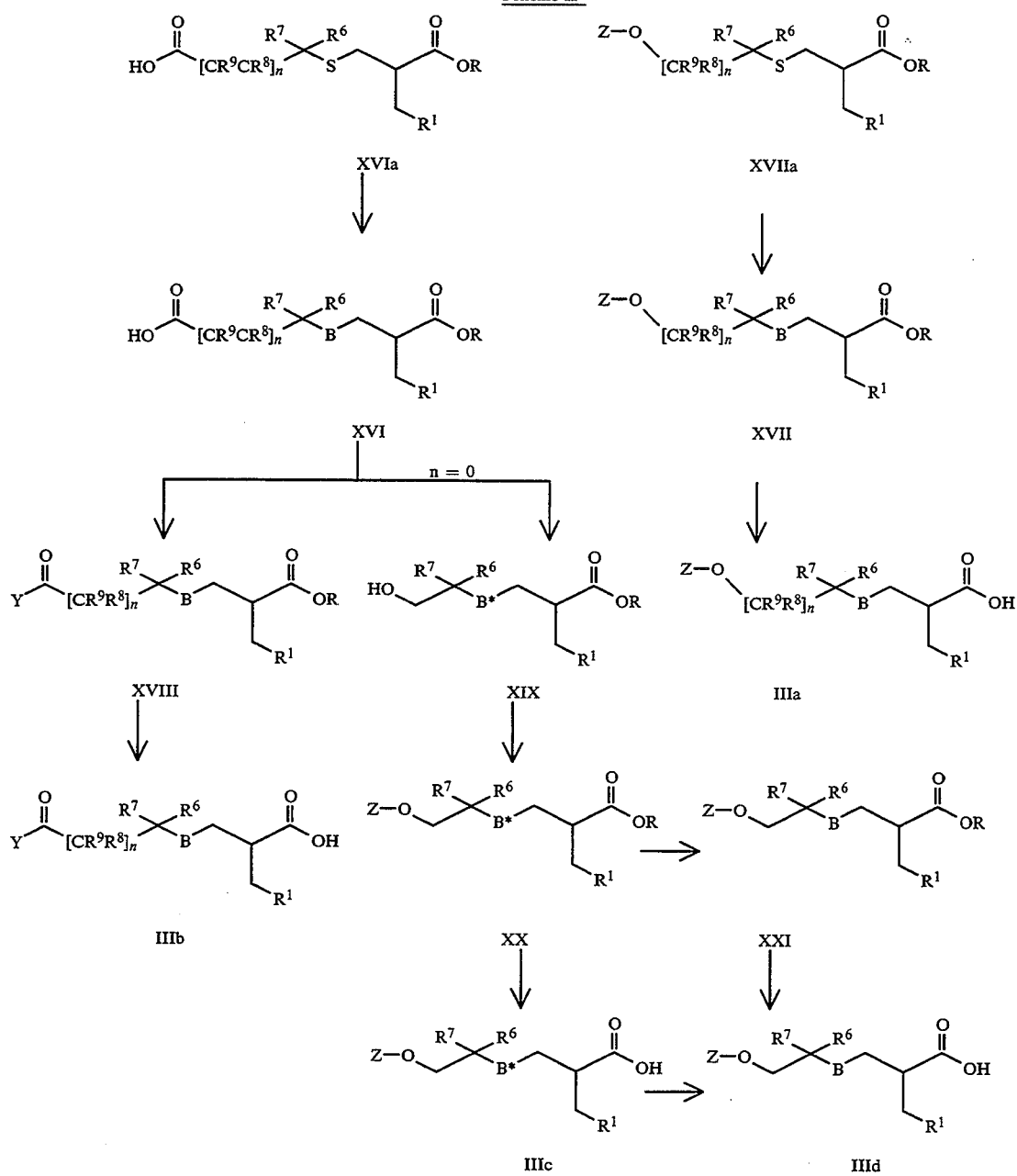
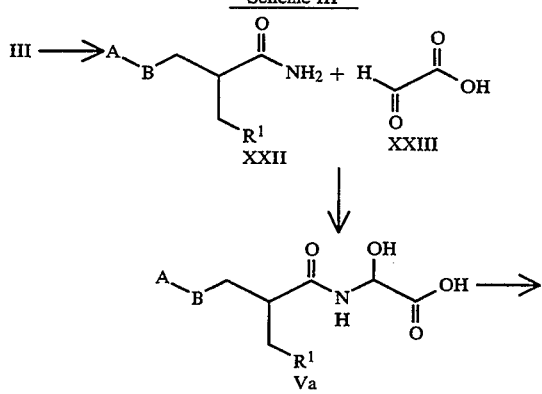
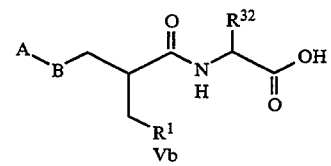
The compounds of the invention and their pharmaceutically usable salts have an inhibitory activity on the natural enzyme renin. The latter passes from the kidneys into the blood and there brings about the cleavage of angiotensinogen with the formation of the decapeptide angiotensin I which is then cleaved in the lungs, the kidneys and other organs to the octapeptide angiotensin II. Angeotensin II increases the blood pressure not only directly by arterial constriction, but also indirectly by the liberation of the sodium ion-retaining hormone aldosterone from the adrenal gland, with which is associated an increase in the extracellular fluid volume. This increase is attributed to the action of angiotensin II itself or to the heptapeptide angiotensin III which is formed therefrom as a cleavage product. Inhibition of the enzymatic activity of renin brings about a decrease in the formation of angiotensin I and as a consequence thereof the formation of a smaller amount of angiotensin II. The reduced concentration of this active peptide hormone is the actual reason for the blood pressure-lowering activity of renin inhibitors.

The activity of renin inhibitors can be demonstrated experimentally by means of the in vitro tests described hereinafter:

A. In vitro test with pure human renin

The test is carried out in Eppendorf test tubes. The incubation mixture consists of (1) 100 μl of human renin in buffer A (0.1M sodium phosphate solution, pH 7.4, containing 0.1% bovine serum albumin, 0.1% sodium azide and 1 mM ethylenediaminetetraacetic acid), sufficient for a renin activity of 2-3 ng of angiotensin I/ml/hr; (2) 145 μl of buffer A: (3) 30 μl of 10 μM human tetradecapeptide renin substrate (hTD) in 10 mM hydrochloric acid: (4) 15 μl of dimethyl sulphoxide with or without inhibitor and (5) 10 μl of a 0.03 molar solution of hydroxyquinoline sulphate in water.

The samples are incubated for three hours at 37° C. and, respectively, 4° C. in triplicate. 2×100 μl samples per experimental test tube are used in order to measure the production of angiotensin I via RIA (standard radioimmunoassay; clinical assay solid phase kit). Cross reactivities of the antibody used in the RIA are: angiotensin I 100%; angiotensin II 0.0013%; hTD (angiotensin I-Val-Ile-His-Ser-OH 0.09%. The production of angiotensin I is determined by the difference between the experiment at 37° C. and that at 4° C.

The following controls are carried out:
(a) Incubation of hTD samples without renin and without inhibitor at 37° C. and 4° C. The difference between these two values gives the base value of the angiotensin I production.
(b) Incubation of hTD samples with renin, but without inhibitor at 37° C. and 4° C. The difference between these values gives the maximal value of angiotensin I production.

In each sample the base value of the angiotensin I production is subtracted from the angiotensin I production which is determined. The difference between the maximal value and the base value gives the value of the maximal substrate hydrolysis (=100%) by renin.

The results are given as $IC_{50}$ values which denote that concentration of the inhibitor at which the enzymatic activity is inhibited by 50%. The $IC_{50}$ values are determined from a linear regression curve from a logit-log plot.

B. In vitro test with human plasma

The test solution comprises (1) 225 μl of plasma, (2) 10 μl of 8-hydroxyquinoline sulphate in water, (3) 12 μl of sodium phosphate buffer (0.1M), pH 7.4, and 13 ml of different concentrations of renin inhibitor in dimethyl sulphoxide. Tho resulting pH value (pH 6) of tho test solution is stable for the duration of the subsequent incubation. The test tubes are then incubated at 37° C. for 3 hours. The enzyme activity is expressed by determining the angiotensin I produced, which is determined using a comercially available radioimmunoassay kit (Clinical Assays, Cambridge, Mass.).

The following controls are carried out:
MaxP: Maximal production (maximal enzyme activity) in the absence of a renin inhibitor.
MinP: Minimal production (enzyme activity blank) in the presence of a supramaximal concentration of a renin inhibitor.

The MinP is subtracted from the respective angiotensin production in each experiment. These values are converted into percentage inhibition by comparison with the maximal enzyme activity MaxP-MinP. The degree of inhibition is expressed by the $IC_{50}$ value, i.e. the concentration of inhibitor which reduces the accumulation of angiotensin I by 50%.

The results obtained in these tests are compiled in the following Table:

TABLE

| Compound | $IC_{50}$ values in nmol/lt | |
|---|---|---|
| | Test A | Test B |
| A | 0.03 | 0.10 |
| B | 0.30 | 0.11 |
| C | 0.061 | 0.14 |
| D | 0.20 | <0.10 |

A=(S)-N-[(1S,2R,3S)-1-(Cyclohexylmethyl)-3-cyclopropyl-2,3-dihydroxypropyl]-α-[(S)-α-[[[1-(morpholinocarbonyl)-1-methylethyl]sulfonyl]methyl]hydrocinnamamido]imadazole-4-propionamide B=2-[2-[[(S)-2-[[(S)-1-[[(1S,2R,3S)-1-(Cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose C=tert-Butyl [(S)-2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate D=2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl methoxyacetate The compounds of formula I as well as their pharmaceutically usable salts can be used as medicaments, e.g., in the form of pharmaceutical preparations. The pharmaceutical preparations can be administered enterally such as orally, e.g., in the form of tablets, coated tablets, dragees, hard and soft gelatine capsules, solutions, emulsions or suspensions, nasally, e.g., in the form of nasal sprays, or rectally, e.g., in the form of suppositories. However, the administration can also be effected parenterally such as intramuscularly or intravenously, e.g., in the form of injection solutions.

The compounds of formula I as well as their pharmaceutically usable salts can be processed with pharmaceutically inert, inorganic or organic excipients for the manufacture of tablets, coated tablets, dragees and hard gelatine capsules. Lactose, corn starch or derivatives thereof, talc, stearic acid or its salts, etc., can be used, e.g., as such excipients for tablets, dragees and hard gelatine capsules.

Suitable excipients for soft gelatine capsules are, e.g., vegetable oils, waxes, fats, semi-solid and liquid polyols, etc.

Suitable excipients for the manufacture of solutions and syrups are, e.g., water, polyols, saccharose, invert sugar, glucose, etc.

Suitable excipients for injection solutions are, e.g., water, alcohols, polyols, glycerol, vegetable oils, etc.

Suitable excipients for suppositories are, e.g., natural or hardened oils, waxes, fats, semi-liquid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, coating agents or antioxidants. They can also contain still other therapeutically valuable substances.

The compounds of the invention as well as their pharmaceutically usable salts can be used in the control or prevention of high blood pressure and cardiac insufficiency. The dosage can vary within wide limits and will, of course, be fitted to the individual requirements in each particular case. In general, in the case of oral administration there should suffice a daily dosage of about 3 mg to about 3 g, preferably about 10 mg to about 1 g, e.g., approximately 300 mg per person, divided in preferably 1–3 unit doses, which can, e.g., be of the same amount, whereby, however, the upper limit just given can also be exceeded when this is found to be indicated. Usually, children receive half of the adult dosage.

The following Examples are intended to illustrate the present invention, but are not intended to be limiting in any manner. All temperatures are given in degrees Celsius. The following abbreviations are used:

His-OH=L-Histidine
Boc=t-Butoxycarbonyl
Fmoc=9-Fluorenylmethoxycarbonyl
DBU=1,8-Diazabicyclo[5.4.0]undec-7-ene[1,5-5]

EXAMPLE 1

A mixture of 239 mg (0.76 mmol) of rac-α-[[(1-carbamoyl-1-methylethyl)sulfonyl]methyl]hydrocinnamic acid, 250 mg (0.69 mmol) of (S)-α-amino-N-[(1S,2R,3S)-1-(cyclohexylmethyl)-3-cyclopropyl-2,3-dihydroxypropyl]imidazole-4-propionamide, 77 mg (0.76mmol) of triethylamine, 118 mg (0.76 mmol) of HOBT and 289 mg (0.76 mmol) of HBTU in 10 ml of dimethylformamide was stirred at room temperature overnight. Subsequently, the reaction solution was evaporated to dryness in a high vacuum, the residue was taken up in 75 ml of ethyl acetate and washed twice with 20 ml of saturated sodium hydrogen carbonate solution each time. The ethyl acetate solutions were dried over sodium sulphate and subsequently evaporated under reduced pressure. For purification and separation of the two epimeric products, the residue (450 mg) was chromatographed on 30 g of silica gel using a 97:3:0.1 o mixture of methylene chloride, methanol and ammonia as the eluent. After lyophilization from dioxan and water there were obtained the less polar epimer (S)-α-[(R)-α-[[(1-carbamoyl-1-methylethyl)sulfonyl]methyl]hydrocinnamamido]-N-[(1S,2R,3S)-1-(cyclohexylmethyl)-3-cyclopropyl-2,3-dihydroxypropyl]-imidazole-4-propionamide as a colourless amorphous powder, MS: 660 (M+H)+, and the more polar epimer (S)-α-[(S)-α-[[(1-carbamoyl-1-methylethyl)sulfonyl]methyl]hydrocinnamamido]-N-[(1S ,2R,3S)-1-(cyclohexylmethyl )-3-cyclopropyl-2,3-dihydroxypropyl]imidazole-4-propionamide, likewise as a colourless amorphous powder, MS: 660 (M+H)+.

The (S)-α-amino-N-[(1S,2R,3S)-1-(cyclohexylmethyl)-3-cyclopropyl-2,3-dihydroxypropyl]imidazole-4-propionamide used as the starting material was prepared as follows:

(a) A solution of 3.21 g of tert-butyl (4S,5R)-4-(cyclohexylmethyl)-5-formyl-2,2-dimethyl-3-oxazolidinecarbonate (WO 87/05302) in 25 ml of tetrahydrofuran was added dropwise at about 15° to a solution of the Grignard compound prepared from 3.94 ml (49 mmol) of bromocyclopropane and 1.2 g (0.049 gram atom) of magnesium shavings in 22 ml of tetrahydrofuran and the reaction mixture Was subsequently stirred at room temperature under argon for 16 hours. Thereafter, the reaction mixture was poured into 40 ml of an ice-cold saturated ammonium chloride solution and extracted twice with 50 ml of ethyl acetate each time. The ethyl acetate extracts were washed with 40 ml of ice-cold saturated ammonium chloride solution, then combined, dried over sodium sulphate and evaporated under reduced pressure. For purification, the residue (4.33 g) was chromatographed over a column of 110 g of silica gel prepared with toluene and 1% triethylamine using a 95:5 mixture of toluene and ethyl acetate as the eluent. There were obtained 1.9 g of tert-butyl (4S,5R)-4-(cyclohexylmethyl)-5-[(S)-cyclopropylhydroxymethyl]-2,2-dimethyl-3-oxazolidinecarbonate, MS: 368 (M+H)+, and 0.5 g of tert-butyl (4S,5R)-4-(cyclohexylmethyl)-5-[(R)-cyclopropylhydroxymethyl]-2,2-dimethyl-3-oxazolidinecarbonate, MS: 368 (M+H)+, each as a colourless oil.

(b) 1.42 g (3.86mmol) of tert-butyl (4S,5R)-4-(cyclohexylmethyl)-5-[(S)-cyclopropylhydroxymethyl]-2,2-dimethyl-3-oxazolidinecarbonate dissolved in 15 ml of methanol and 10 ml of water were treated with 4 ml of 7.5N hydrochloric acid and stirred at 500 for 3 hours. The reaction solution was cooled to 3° in an ice bath, treated dropwise with 4 ml of 7.5N sodium hydroxide solution and stirred for a further 1 hour. The suspension obtained was evaporated under reduced pressure, water was removed by two-fold azeotroping with 10 ml of toluene and the residue was stirred three times with 10 ml of a 95:5 mixture of methylene chloride and methanol. The insoluble residue was filtered off and the filtrate was evaporated under reduced pressure. The resulting crude product (1.14 g) was suspended in 15 ml of ether and thereafter filtered off under suction. There was obtained 0.58 g of (1S,2R,3S)-3-amino-4-cyclohexyl-1-cyclopropyl-1,2-butanediol as colourless crystals, m.p. 141–142°.

(c) A mixture of 343 mg (1.51 mmol) of (1S,2R,3S)-3-amino-4-cyclohexyl-1-cyclopropyl-1,2-butanediol, 995mg (1.66mmol) of Fmoc-His(Fmoc)-OH, 0.21 ml (1.61 mmol) of 4-ethylmorpholine, 449 mg (3.22 mmol) of HOBT and 347 mg (1.81 mmol) of EDC in 20 ml of dimethylformamide was left to stand at room temperature overnight. Thereafter, the reaction mixture was evaporated in a high vacuum, the residue was poured into a mixture of ice and 90 ml of sodium bicarbonate solution and extracted three times with 150 ml of ethyl acetate each time. The three ethyl acetate extracts were washed in succession with 70 ml of saturated ammonium chloride solution, 70 ml of 2N sodium bicarbonate solution and 70 ml of saturated sodium chloride solution, combined, dried over magnesium sulphate, filtered and evaporated. The crude product obtained was stirred at room temperature for 3 hours in 60 ml of methylene chloride and 2 ml of piperidine. Then, the reaction mixture was evaporated and the residue was triturated with 50 ml of hexane and filtered off. The filtrate was chromatographed on 70 g of silica gel with a 65:10:1 mixture of methylene chloride, methanol and ammonia as the eluent, whereby there were obtained 390 mg of (S)-α-amino-N-[(1S,2R,3S)-1-(cyclohexylmethyl)-3-cyclopropyl-2,3-dihydroxypropyl]imidazole-4-propionamide as a colourless foam; MS: 365 (M+H)+.

The rac-α-[[(1-carbamoyl-1-methylethyl)sulfonyl]methyl]hydrocinnamic acid used as the starting material was prepared as follows:

(d) 8.4 g (55.4 mm01) of DBU were added dropwise to a solution of 3.3 g (27.7 mmol) of 2-mercaptoisobutyric acid [Can. J. Chem. 61(8), 1872]and 6.9 g (27.7 mmol) of benzyl 2-benzylacrylate (EPA 0117429), whereby the temperature of the reaction mixture was held between 5 and 10°. After completion of the addition the mixture was stirred at 10° for a further 5 hours. Subsequently, the reaction mixture was treated dropwise with 22.5 g (36.6 mmol) of potassium monopersulphate triple salt suspended in 450 ml of water while cooling with ice, whereby the temperature was held below 10°. Thereafter, the mixture was stirred at the same temperature for a further hour, then cooled to 0° and a further 22.5 g (36.6 mmol) of potassium monopersulphate triple salt were added spatulawise. The mixture was left to warm slowly to room temperature and was stirred for a further 15 hours. For the working-up, the mixture was diluted with 200 ml of water and extracted four times with 60 ml of ethyl acetate each time. The combined organic extracts were dried over sodium sulphate and evaporated under reduced pressure until the product began to crystallize. Then, 30 ml of hexane and 20 ml of ether were added while stirring, the separated product was subsequently filtered off under suction and dried. There were obtained 9.7 g of (RS)-2-[[2-[(benzyloxy)carbonyl]-3-phenylpropyl]sulfonyl]-2-methylpropionic acid as a colourless solid; MS: 422 (M+NH4)+.

(e) A solution of 1.0 g (2.5 mmol) of (RS)-2-[[2-[(benzyloxy)carbonyl]-3-phenylpropyl]sulfonyl]-2-methylpropionic acid and 1.07 ml (12.5 mmol) of oxalyl chloride in 2 ml of tetrahydrofuran was heated at 500 for 18 hours. Thereafter, the reaction solution was evaporated under reduced pressure. The residue was taken up twice in 30 ml of toluene each time and again evaporated under reduced pressure each time. (RS)-2-[[2-[(Benzyloxy)carbonyl]-3-phenylpropyl]sulfonyl]-2-methylpropionyl chloride was obtained as a yellowish oil in quantitative yield and was used in the following step without purification and characterization.

(f) A solution of 1.05 g (2.5 mmol) of crude (RS)-2-[[2-[(benzyloxy)carbonyl]-3-phenylpropyl]sulfonyl]-2-methylpropionyl chloride in 29 ml (9.3 mmol) of 0.32M ammonia in tetrahydrofuran was stirred at room temperature for 5 hours. Subsequently, the reaction solution was diluted with 40 ml of ethyl acetate and extracted with 20 ml of 1N hydrochloric acid. The ethyl acetate extract was then washed with 20 ml of saturated sodium hydrogen carbonate solution and 20 ml of saturated sodium chloride solution, dried over sodium sulphate and evaporated under reduced pressure. There was obtained 0.92 g of benzyl rac-α-[[(1-carbamoyl-1-methylethyl)sulfonyl]methyl]hydrocinnamate as a colourless solid, MS: 312 (M-benzyl)+.

(g) A suspension of 0.74 g (1.83 mmol) of benzyl rac-α-[[(1-carbamoyl-1-methylethyl)sulfonyl]methyl]hydrocinnamate and 200 mg of palladium/charcoal (5%) in 30 ml of methanol was hydrogenated at room temperature under normal pressure for 2 hours. Subsequently, the catalyst was filtered off and the solution was evaporated under reduced pressure. There was obtained 0.54 g of rac-α-[[(1-carbamoyl-1-methylethyl)sulfonyl]methyl]hydrocinnamic acid as a colourless solid, MS: 314 (M+H)+.

EXAMPLE 2

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl]imidazole-4-propionamide and rac-α-[[[1-(morpholinocarbonyl)-1-methylethyl]sulfonyl]methyl]hydrocinnamic acid the (S)-N-[(1S,2R,3S)-1-(cyclohexylmethyl)-3-cyclopropyl-2,3-dihydroxypropyl]-α-[(R)-α-[[[1-(morpholinocarbonyl)-1-methylethyl]sulfonyl]methyl]hydrocinnamamido]imidazole-4-propionamide as a colourless solid MS: 730 (M+H)+, and the epimeric (S)-N-[(1S,2R,3S)-1-(cyclohexylmethyl)-3-cyclopropyl-2,3-dihydroxypropyl]-α-[(S)-α-[[[1-(morpholinocarbonyl)-1-methylethyl]sulfonyl]methyl]hydrocinnamamido]imidazole-4-propionamide as a colourless foam, MS: 730 (M+H)+;

from (S)-α-amino-N-[(1S,2R,3S)-1-(cyclohexylmethyl)-3-cyclopropyl-2,3-dihydroxypropyl]imidazole-4-propionamide and (RS)-α-[[[1-(cyclopropylcarbamoyl)-1-methylethyl]sulfonyl]methyl]hydrocinnamic acid the (S)-N-[(1S,2R,3S)-1-(cyclohexylmethyl)-3-cyclopropyl-2,3-dihydroxypropyl]-α-[(R)-α-[[[1-(cyclopropylcarbamoyl)-1-methylethyl]sulfonyl]methyl]hydrocinnamamido]imidazole-4-propionamide, MS: 700 (M+H)+, and the epimeric (S)-N-[(1S,2R,3S)-1-(cyclohexylmethyl)-3-cyclopropyl-2,3-dihydroxypropyl]-α-[(S)-α-[[[1-(cyclopropylcarbamoyl)-1-methylethyl]sulfonyl]methyl]hydrocinnamamido]imidazole-4-propionamide, MS: 700 (M+H)+, each as a colourless, amorphous solid;

from (S)-α-amino-N-[(1S,2R,3S)-1-(cyclohexylmethyl)-3-cyclopropyl-2,3-dihydroxypropyl]imidazole-4-propionamide and rac-α-[[[1-methyl-1-[(2-sulphoethyl)carbamoyl]ethyl]sulfonyl]methyl]hydrocinnamic acid the 2-[2-[[(R)-2-[[(S)-1-[[(1S,2R,3S)-1-cyclohexylmethyl)-3-cyclopropyl-2,3-dihydroxypropyl]-carbamoyl]-2-imidazol-4-ylethyl]carbamoyl]-3-phenylpropyl]sulfonyl]-2-methylpropionamido]ethanesulphonic acid, MS: 768 (M+H)+, and the epimeric 2-[2-[[(S)-2-[[(S)-1--[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]ethanesulphonic acid, MS: 768 (M+H)+, each as an amorphous solid;

from (S)-α-amino-N-[(1S,2R,3S)-1-(cyclohexylmethyl)-3-cyclopropyl-2,3-dihydroxypropyl-]imidazole-4-propionamide and rac-α-[[[1-[(4-hydroxypiperidino)carbonyl]-1-methylethyl]sulfonyl]methyl]hydrocinnamic acid the (S)-N-[(1S,2R,3S)-1-(cyclohexylmethyl)-3-cyclopropyl-2,3-dihydroxypropyl]-α-[(R)-α-[[[1-[(4-hydroxypiperidino)carbonyl]-1-methylethyl]sulfonyl]methyl]hydrocinnamamido]imidazole-4-propionamide, MS: 744 (M+H)+, and the epimeric (S)-- N-[(1S,2R,3S)-1-(cyclohexylmethyl)-3-cyclopropyl-2,3-dihydroxypropyl]-α-[(S)-α-[[[1-[(4-hydroxypiperidino)carbonyl]-1-methylethyl]sulfonyl]methyl]hydrocinnamamido]imidazole-4-propionamide, MS: 744 (M+H)+, each as an amorphous solid;

from (S)-α-amino-N-[(1S,2R,3S)-1-(cyclohexylmethyl)-3-cyclopropyl-2,3-dihydroxypropyl-]imidazole-4-propionamide and rac-α-[[[1-[(1-benzyl-4-piperidinyl)carbamoyl]-1-methylethyl]sulfonyl]methyl]hydrocinnamic acid the (S)-α-[(S or R)-α-[[[1-[(1-benzyl-4-piperidinyl)carbamoyl]-1-methylethyl]sulfonyl]methyl]hydrocinnamamido]-N-[(1S,2R,3S)-1-(cyclohexylmethyl)- 3-cyclopropyl-2,3-dihydroxypropyl]imidazole-4-propionamide, MS: 833 (M+H)+, and the epimeric (S)-α-[(R or S)-α-[[[1-[(1-benzyl-4-piperidinyl)carbamoyl]-1-methylethyl]sulfonyl]methyl]hydrocinnamamido]-N-[(1S,2R,3S)-1-(cyclohexylmethyl)-3-cyclopropyl-2,3-dihydroxypropyl]imidazole-4-propionamide, MS: 833 (M+H)+, each as a colourless solid;

from (S)-α-amino-N-[(1S,2R,3S)-1-(cyclohexylmethyl)-3-cyclopropyl-2,3-dihydroxypropyl-]imidazole-4-propionamide and rac-α-[[[1-[[4-(2-hydroxyethyl)-1-piperazinyl]carbonyl]-1-methylethyl]sulfonyl]methyl]hydrocinnamic acid the (S)-N-[(1S,2R,3S)-1-(cyclohexylmethyl)-3-cyclopropyl-2,3-dihydroxypropyl]-α-[(R or S)-α-[[[1-[4-(2-hydroxyethyl)-1-piperazinyl]carbonyl]-1-methylethyl]sulfonyl]methyl]hydrocinnamamido]imidazole-4-propionamide, MS: 773 (M+H)+, and the epimeric (S)-N-[(1S,2R,3 S)-1-(cyclohexylmethyl)-3-cyclopropyl-2,3-dihydroxypropyl]-α-[(S or R)-α-[[[1-[4-(2-hydroxyethyl)-1-piperazinyl]carbonyl]-1-methylethyl]sulfonyl]methyl]hydrocinnamamido]imidazole-4-propionamide, MS: 773 (M+H)+, each as a colourless solid;

from (S)-α-amino-N-[(1S,2R,3S)-1-(cyclohexylmethyl)-3-cyclopropyl-2,3-dihydroxypropyl-]imidazole-4-propionamide and (RS)-α-[[[1-[[(RS)-3-hydroxyl-1-pyrrolidinyl]carbonyl]-1-methylethyl]sulfonyl]methyl]hydrocinnamic acid the (S)-N-[(1S,2R,3S)-1-(cyclohexylmethyl)-3-cyclopropyl-2,3-dihydroxypropyl]-α-[(R or S)-α-[[[1-[[(RS)-3-hydroxy-1-pyrrolidinyl]carbonyl]-1-methylethyl]sulfonyl]methyl]hydrocinnamamido]imidazole-4-propionamide, MS: 730 (M+H)+, and the epimeric (S)-N-[(1S,2R,3S)-1-(cyclohexylmethyl)-3-cyclopropyl-2,3-dihydroxypropyl]α-[(S or R)-α-[[[1-[[(RS)-3-hydroxyl-1-pyrrolidinyl]carbonyl]-1-methylethyl]sulfonyl]methyl]hydrocinnamamido]imidazole-4-propionamide, MS: 730 (M+H)+, each as a colourless solid;

from (S)-α-amino-N-[(1S,2R,3S)-1-(cyclohexylmethyl)-3-cyclopropyl-2,3-dihydroxypropyl-]imidazole-4-propionamide and (RS)-α-[[[1-[[(3RS,4RS)-3,4-dihydroxy-1-pyrrolidinyl]carbonyl]-1-methylsulfonyl]methyl]hydrocinnamic acid the (S)-N-[(1S,2R,3S)-1-(cyclohexylmethyl)-3-cyclopropyl-2,3-dihydroxypropyl-α-[ (RS)-α-[1-[[[(all-RS)-3,4-dihydroxy-1-pyrrolidinyl]carbonyl]methyl]sulfonyl]-1-methylethyl]hydrocinnamamido]imidazole-4-propionamide, MS: 746 (M+H)+, as an amorphous solid;

from (S)-α-amino-N-[(1S,2R,3S)-1-(cyclohexylmethyl)-3-cyclopropyl-2,3-dihydroxypropyl-]imidazole-4-propionamide and (RS)-α-[[[1-[(R)-2-(hydroxymethyl)-1-pyrrolidinyl]carbamoyl ]-1-methylethyl]sulfonyl]methyl]hydrocinnamic acid the (S)-N-[(1S,2R,3S)-1-(cyclohexylmethyl)-3-cyclopropyl-2,3-dihydroxypropyl]-α-[(S or R)-α-[[[1-[[(R)-2-(hydroxymethyl)-1-pyrrolidinyl]carbonyl]-1-methylethyl]sulfonyl]methyl]hydrocinnamamido]imidazole-4-propionamide, MS: 744 (M+H)+, as a colourless foam and the epimeric (S)-N-[(1S,2R,3S)-1-(cyclohexylmethyl)-3-cyclopropyl-2,3-dihydroxypropyl]-α-[(R or S)-{z-[[[1-[[(R)-2-(hydroxymethyl)-1-pyrrolidinyl]carbonyl]-1-methylethyl]sulfonyl]methyl]hydrocinnamamido]imidazole-4-propionamide, MS: 744 (M+H)+, each as a colourless solid;

from (S)-α-amino-N-[(1S,2R,3S)-1-(cyclohexylmethyl)-3-cyclopropyl-2,3-dihydroxypropyl-]imidazole-4-propionamide and rac-α-[[[1-methyl-1-[(2-pyridylmethyl)carbamoyl]ethyl]sulfonyl]methyl]hydrocinnamic acid the (S)-α-[(R or S)-α-[[[1-[(2pyridylmethyl)carbamoyl]-1-methylethyl]sulfonyl]methyl]hydrocinnamamido]-N-[(1S,2R,3S)-1-(cyclohexylmethyl)-3-cyclopropyl-2,3-dihydroxypropyl]imidazole-4-propionamide, MS: 751 (M+H)+, and the epimeric (S)-α-[(S or R)-α-[[[1-[(2-pyridylmethyl)carbamoyl]-1-methylethyl]sulfonyl]methyl]hydrocinnamamido]-N-[(1S,2R,3S)-1-(cyclohexylmethyl)-3-cyclopropyl-2,3-dihydroxypropyl]imidazole-4-propionamide, MS: 75 1 (M+H)+, each as a colourless solid;

from (S)-α-amino-N-[(1S,2R,3S)-1-(cyclohexylmethyl)-3-cyclopropyl-2,3-dihydroxypropyl-]imidazole-4-propionamide and (RS)-α-[[[1-[[1-(methoxycarbonyl)-1-methylethyl]carbamoyl]-1-methylethyl]sulfonyl]methyl]hydrocinnamic acid the methyl 2-[2-[[[(R or S)-2-[[(S)-1-[[(1S,2R,3S)-1-(cyclohexylmethyl)-3-cyclopropyl-2,3-dihydroxypropyl]carbamoyl]-2-imidazol-4 -ylethyl]carbamoyl]-3-phenylpropyl]sulfonyl]-2-methylpropionamido]-2-methylpropionate, MS: 760 (M+H)+, and the epimeric methyl 2-[2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2methylpropionamido]-2-methylpropionate, MS: 760 (M+H)+, each as a colourless solid;

from (S)-α-amino-N-[(1S,2R,3S)-1-(cyclohexylmethyl)-3-cyclopropyl-2,3-dihydroxypropyl-]imidazole-4-propionamide and rac-α-[[[1-[bis(2-methoxyethyl)carbamoyl]-1-methylethyl]sulfonyl]methyl]hydrocinnamic acid the (S)-α-[(S or R)-α-[[[1-[bis(2-methoxyethyl)carbamoyl]-1-methylethyl]sulfonyl]methyl]hydrocinnamamido]-N-[(1S ,2R,3S)-1-(cyclohexylmethyl)-3-cyclopropyl-2,3-dihydroxypropyl]imidazole-4-propionamide, MS: 776 (M+H)+, and the epimeric (S)-α-[(R or S)-α-[[[1-[bis(2-methoxyethyl)carbamoyl]-1-methylethyl]sulfonyl]methyl]hydrocinnamamido]-

N-[(1S,2R,3S)-1-(cyclohexylmethyl)-3-cyclopropyl-2,3-dihydroxypropyl]imidazole-4-propionamide, MS: 776 (M+H)+, each as a colourless solid; from (S)-α-amino-N-[(1S,2R,3S)-1-(cyclohexylmethyl)-3-cyclopropyl-2,3-dihydroxypropyl]imidazole-4-propionamide and rac-α-[[[1-[[4-(tert-butoxycarbonyl)-1-piperazinyl]carbonyl]-1-methylethyl]sulfonyl]methyl]hydrocinnamic acid the tert-butyl 4-[2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionyl]-1-piperazinecarbonate MS: 829 (M+H)+, and the epimeric tert-butyl 4-[2-[[(S)-2-[[(R or S)-1-[[(1S,2R,3S)-1-(cyclohexylmethyl-3-cyclopropyl-2,3-dihydroxypropyl]carbamoyl]-2-imidazol-4-ylethyl]carbamoyl]-3-phenylpropyl]sulfonyl]-2-methylpropionyl]-1-piperazinecarbonate, MS: 829 (M+H)+, each as a colourless, amorphous solid.

The acids used as the starting materials were prepared as follows: rac-α-[[[1-(Morpholinocarbonyl)-1-methylethyl]sulfonyl]methyl]hydrocinnamic acid:

(a) 0.64 ml (7.3 mmol) of morpholine dissolved in 1 ml of tetrahydrofuran was added dropwise while cooling with ice to a solution of 0.97 g (2.3 mmol) of crude (RS)-2-[[2-[(benzyloxy)carbonyl]-3-phenylpropyl]sulfonyl]-2-methylpropionyl chloride in 1 ml of tetrahydrofuran. The reaction mixture was left to warm to room temperature within 1 hour, whereby a precipitate formed. Subsequently, the mixture was diluted with 20 ml of ethyl acetate and the solution was adjusted to pH 2 with 1N hydrochloric acid. The ethyl acetate phase was washed with 20ml of saturated sodium hydrogen carbonate solution and 20 ml of saturated sodium chloride solution, dried over sodium sulphate and evaporated under reduced pressure. For purification, the crude product was chromatographed on 30 g of silica gel with a 3:1 mixture of toluene and ethyl acetate as the eluent. There was obtained 0.98 g of benzyl rac-α-[[1-methyl-1(morpholinocarbonyl)ethyl](morpholinocarbonyl)ethyl]sulfonyl]methyl]hydrocinnamate as a colourless oil, MS: 473 (M)+.

(b) In an analogous manner to that described in Example 1, paragraph (g), by catalytically hydrogenating benzyl rac-α-[[1-methyl-1-(morpholinocarbonyl)ethyl]sulfonyl]methyl]hydrocinnamate there was obtained rac-α-[[[1-(morpholinocarbonyl)-1-methylethyl]sulfonyl]methyl]hydrocinnamic acid as a colourless foam, MS: 383 (M)+.

rac-α-[[[1-(Cyclopropylcarbamoyl)-1-methylethyl]sulfonyl]methyl]hydrocinnamic acid:

(c) A solution of 1.07 g (2.5 mmol) of (RS)-2-[[2-[(benzyloxy)carbonyl]-3-phenylpropyl]sulfonyl]-2-methylpropionyl chloride and 0.42 g (7.4 mmol) of cyclopropylamine in 20 ml of pyridine was stirred at room temperature for 2 hours. Thereafter, the reaction solution was evaporated under reduced pressure and the residue was chromatographed on 30 g of silica gel using a 99:1 mixture of methylene chloride and methanol as the eluent. There was obtained 0.96 g of benzyl rac-α-[[[1-(cyclopropylcarbamoyl)-1-methylethyl]sulfonyl]methyl]hydrocinnamate as a yellowish solid, MS: 444 (M)+.

(d) In an analogous manner to that described in Example 1, paragraph (g), by catalytically hydrogenating benzyl rac-α-[[1-(cyclopropylcarbamoyl)-1-methylethyl]sulfonyl]methyl]hydrocinnamate there was obtained rac-α-[[[1-(cyclopropylcarbamoyl)-1-methylethyl]sulfonyl]methyl]hydrocinnamic acid as a colourless solid, MS: 354 (M+H)+.

The following acids were prepared in an analogous manner to that described in paragraphs (c) and (d) above:

(e) From (RS)-2-[[2-[(benzyloxy)carbonyl]-3-phenylpropyl]sulfonyl]-2-methylpropionyl chloride and 2-aminoethanesulphonic acid in pyridine the benzyl rac-α-[[[1-methyl-1-[(2sulphoethyl)carbamoyl]ethyl]sulfonyl]methyl]hydrocinnamate, MS: 510 (M+H)−, as a colourless foam ,catalytic hydrogenation of which yielded rac-α-[[[1-methyl-1-[(2-sulphoethyl)carbamoyl]ethyl]sulfonyl]methyl]hydrocinnamic acid, MS: 460 (M+K)+, as a colourless foam;

(f) from (RS)-2-[[2-[(benzyloxy)carbonyl]-3-phenylpropyl]sulfonyl]-2-methylpropionyl chloride and 4-hydroxypiperidine in pyridine the benzyl rac-α-[[[1-[(4-hydroxypiperidino)carbonyl]-1-methylethyl]sulfonyl]methyl]hydrocinnamate, MS: 488 (M+H)+, as an amorphous solid, catalytic hydrogenation of which yielded rac-α-[[[1-[(4-hydroxypiperidino)carbonyl]-1-methylethyl]sulfonyl]methyl]hydrocinnamic acid, MS: 397 (M)+, as a colourless foam.

The following acids were prepared in an analogous manner to that described in paragraphs (a) and (b) above:

(g) From (RS)-2-[[2-[(benzyloxy)carbonyl]-3-phenylpropyl]sulfonyl]-2-methylpropionyl chloride and 4-amino-N-benzylpiperidine the benzyl rac-α-[[[1-[(1-benzyl-4-piperidinyl)carbamoyl]-1-methylethyl]sulfonyl]methyl]hydrocinnamate, MS: 577 (M+H)+, as a colourless oil, catalytic hydrogenation of which yielded rac-α-[[[1-[(1-benzyl-4-piperidinyl)carbamoyl]-1-methylethyl]sulfonyl]methyl]hydrocinnamic acid as a colourless foam which was used directly in the next step;

(h) from (RS)-2-[[2-[(benzyloxy)carbonyl]-3-phenylpropyl]sulfonyl]-2-methylpropionyl chloride and N-(2-hydroxyethyl)piperazine the benzyl rac-α-[[(1-[[4-(2-hydroxyethyl)-1-piperazinyl]carbonyl]-1-methylethyl]sulfonyl]methyl]hydrocinnamate, MS: 517 (M+H)+, as a colourless, amorphous solid, catalytic hydrogenation of which yielded rac-α-[[(1-[[4-(2-hydroxyethyl)-1-piperazinyl]carbonyl]-1-methylethyl]sulfonyl]methyl]hydrocinnamic acid as a colourless foam which was used directly in the next step;

(i) from (RS)-2-[[2-[(benzyloxy)carbonyl]-3-phenylpropyl]sulfonyl]-2-methylpropionyl chloride and 3-hydroxypyrrolidine the benzyl (RS)-α-[[[1-[[(RS)-3-hydroxyl-1-pyrrolidinyl]carbonyl]-1-methylethyl]sulfonyl]methyl]hydrocinnanate, MS: 474 (M+H)+, as a colourless oil, catalytic hydrogenation of which yielded (RS)-α-[[[1-[[(RS)-3-hydroxyl-1-pyrrolidinyl]carbonyl]-1-methylethyl]sulfonyl]methyl]hydrocinnamic acid as a colourless oil which was used directly in the next step;

(j) from (RS)-2-[[2-[(benzyloxy)carbonyl]-3-phenylpropyl]sulfonyl]-2-methylpropionyl chloride and (R)-(-)-2-(hydroxymethyl)pyrrolidine the benzyl (RS)-α-[[[1-[[(R)-2-(hydroxymethyl)-1-pyrrolidinyl]carbonyl]-1-methylethyl]sulfonyl]methyl]hydrocinnamate, MS: 488 (M+H)+, as a colourless oil, catalytic hydrogenation of which yielded (RS)-α-[[[1-[(R)-2-hydroxymethyl)-1-pyrrolidinyl]carbamoyl]-1-methylethyl]sulfonyl]methyl]hydrocinnamic acid as a colourless oil which was used directly in the next step;

(k) from (RS)-2-[[2-[(benzyloxy)carbonyl]-3-phenylpropyl]sulfonyl]-2-methylpropionyl chloride and 2-(aminomethyl)pyridine the benzyl rac-α-[[[1-methyl-1-[(2-pyridylmethyl)carbamoyl] ethyl]sulfonyl]methyl]hydrocinnamate, MS: 495 (M+H)+, as a colourless oil, catalytic hydrogenation of which yielded rac-α-[[[1-methyl-1-[2-pyridylmethyl)carbamoyl]ethyl]sulfonyl]methyl]hydrocinnamic acid as a colourless foam which was used directly in the next step;

(l) from (RS)-2-[[2-[(benzyloxy)carbonyl]-3-phenylpropyl]sulfonyl]-2-methylpropionyl chloride and methyl 2-aminoisobutyrate the benzyl (RS)-α-[[[1-[[1-(methoxycarbonyl)-1-methylethyl]carbamoyl]-1-methylethyl]sulfonyl]methyl]hydrocinnamate, MS: 504 (M+H)+, as a colourless solid, catalytic hydrogenation of which yielded (RS)-α-[[[1-[[1-(methoxycarbonyl)-1-methylethyl]carbamoyl]-1-methylethyl]sulfonyl]methyl]hydrocinnamic acid as a colourless foam which was used directly in the next step;

(m) from (RS)-2-[[2-[(benzyloxy)carbonyl]-3-phenylpropyl]sulfonyl]-2-methylpropionyl chloride and bis(2-methoxyethyl)amine the benzyl rac-α-[[[1-[bis(2-methoxyethyl)carbamoyl]-1-methylethyl]sulfonyl]methyl]hydrocinnamate, MS: 520 (M+H)+, as a colourless oil, catalytic hydrogenation of which yielded rac-α-[[[1-[bis(2-methoxyethyl)carbamoyl]-1-methylethyl]sulfonyl]methyl]hydrocinnamic acid as a colourless oil which was used directly in the next step;

(n) from (RS)-2-[[2-[(benzyloxy)carbonyl]-3-phenylpropyl]sulfonyl]-2-methylpropionyl chloride and tert.butyl 1-piperazinecarboxylate [J. Org. Chem. 48(5), 661] the benzyl rac-α-[[[1-[[4-(tert-butoxycarbonyl)-1-piperazinyl]carbonyl]-1-methyethyl]sulfonyl]methyl]hydrocinnamate, MS: 595 (M+Na)+, as a colourless solid, catalytic hydrogenation of which yielded rac-α-[[[1-[[4-(tert-butoxycarbonyl)-1-piperazinyl]carbonyl]-1-methylethyl]sulfonyl]methyl]hydrocinnamic acid, MS: 426 (M−C₄H₈)+, as an amorphous solid.

(RS)-α-[[[1-[[(3RS,4RS)-3,4-Dihydroxy-1-pyrrolidinyl]carbonyl]-1-methylethyl]sulfonyl]methyl]hydrocinnamic acid:

(o) In an analogous manner to that described in paragraph (a) above from (RS)-2-[[2-[(benzyloxy)carbonyl]-3-phenylpropyl]sulfonyl]-2-methylpropionyl chloride and 3-pyrroline there was obtained benzyl rac-α-[[[1-methyl-1-(3-pyrrolin-1-ylcarbonyl)ethyl]sulfonyl]methyl]hydrocinnamate, MS: 456 (M+H)+, as a colourless oil.

(p) 832 mg (6.16mmol) of 4-methylmorpholine 4-oxide monohydrate and 10 ml of an osmium tetroxide solution [1.0 g of osmium tetroxide and 1 ml of tert-butyl hydroperoxide (70% in water) in 199 ml of tert-butanol]were added at room temperature to a solution of 935 mg (2.05 mmol) of benzyl rac-α-[[[1-methyl-1-(3-pyrrolin-1-ylcarbonyl)ethyl]sulfonyl]methyl]hydrocinnamate in 30 ml of acetone and 10 ml of water. The reaction mixture was stirred at room temperature for three days. Subsequently, the solvent was evaporated under reduced pressure, the residue was poured into 80 ml of ice-cold 10% citric acid solution and extracted with 240 ml of ethyl acetate. The organic extracts were washed twice with 80 ml of water each time and the combined aqueous phases were back-extracted twice with 80 ml of ethyl acetate each time. The combined ethyl acetate extracts were dried over magnesium sulphate and evaporated under reduced pressure. For purification, the crude product (1.1 g) was chromatographed on 80 g of silica gel with a 1:4 mixture of toluene and ethyl acetate as the eluent. There were obtained 750 mg of benzyl (RS)-α-[[[1-[[(3RS,4RS)-3,4-dihydroxy-1-pyrrolidinyl]carbonyl]-1-methylethyl]sulfonyl]methyl]hydrocinnamate as a colourless oil, MS: 490 (M+H)+.

(q) Catalytic hydrogenation of benzyl (RS)-α-[[[1-[[(3RS,4RS)-3,4-dihydroxy-1-pyrrolidinyl]carbonyl]-1-methylethyl]sulfonyl]methyl]hydrocinnamate in an analogous manner to that described in paragraph (b) above gave (RS)-α-[[[1-[[(3RS,4RS)-3,4-dihydroxy-1-pyrrolidinyl]carbonyl]-1-methylethyl]sulfonyl]methyl]hydrocinnamic acid as a colourless oil which was used directly in the next step.

EXAMPLE 3

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl]imidazole-4-propionamide and (RS)-α-[[[RS)-2,3-dihydroxypropyl]sulfonyl]methyl]hydrocinnamic acid the (S)-N-[(1S,2R,3S)-1-(cyclohexylmethyl)-3-cyclopropyl-2,3-dihydroxypropyl[-α-[(RS)-2,3-dihydroxypropyl]sulfonyl]methyl]hydrocinnamamido]imidazole-4-propionamide, MS: 649 (M+H)+, as a colourless foam;

from (S)-α-amino-N-[(1S,2R,3S)-1-(cyclohexylmethyl)-3-cyclopropyl-2,3-dihydroxypropyl]imidazole-4-propionamide and (RS)-α-[[[(R)-2-(1-tert-butoxyformamido)-2-(morpholinocarbonyl)ethyl]sulfonyl]methyl]hydrocinnamic acid the tert-butyl [(R)-2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-(morpholinocarbonyl)ethyl]carbamate, MS: 831 (M+H)+, and the epimeric tert-butyl [(R)-2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-(morpholinocarbonyl)ethyl]carbamate, MS: 831 (M+H)+, each as a colourless solid;

from (S)-α-amino-N-[(1S,2R,3S)-1-(cyclohexylmethyl)-3-cyclopropyl-2,3-dihydroxypropyl]imidazole-4-propionamide and (RS)-α-[[[(S)-2-(1-tert-butoxyformamido)-2-(morpholinocarbonyl)ethyl]sulfonyl]methyl]hydrocinnamic acid the tert-butyl [(S)-2-[[(S or R)-2-[[(S)-1-[[(1S,2R,3S)-1-(cyclohexylmethyl)-3-cyclopropyl-2,3-dihydroxypropyl]carbamoyl]-2-imidazol-4ylethyl]carbamoyl]-3-phenylpropyl]sulfonyl]-2-(morpholinocarbonyl)ethyl]carbamate, MS: 831 (M+H)+, and the epimeric tert-butyl [(S)-2-[[(R or S)-2-[[(S)-1-[[(1S,2R,3S)-1-(cyclohexylmethyl)-3-cyclopropyl-2,3-dihydroxypropyl]carbamoyl]-2- imidazol-4-ylethyl]carbamoyl]-3-phenylpropyl]sulfonyl]-2-(morpholinocarbonyl)ethyl]carbamate, MS: 831 (M+H)+, each as a colourless solid;

from (S)-α-amino-N-[(1S,2R,3S)-1-(cyclohexylmethyl)-3-cyclopropyl-2,3-dihydroxypropyl]imidazole-4-propionamide and rac-α-[[[2-(morpholinocarbonyl)ethyl]sulfonyl]methyl]hydrocinnamic acid the (S)-N-[(1S,2R,3S)-1-(cyclohexylmethyl)-3-cyclopropyl-2,3-dihydroxypropyl]-α-[(R or S)-α-[[[2-(morpholinocarbonyl)ethyl]sulfonyl]methyl]hydrocinnamamido]imidazole-4-propionamide, MS 716 (M+H)+, and the epimeric (S)-N-[(1S,2R,3S)-1-(cyclohexylmethyl-3-cyclopropyl-2,3-dihydroxypropyl]-α-[(S or R)-α-[[[2-(morpholinocarbonyl)ethyl]sulfonyl]methyl]hydrocinnamamido]imidazole-4-propionamide, MS: 716 (M+H)+, each as a colourless solid;

from (S)-α-amino-N-[(1S,2R,3S)-1-(cyclohexylmethyl)-3-cyclopropyl-2,3-dihydroxypropyl]imidazole-4-propionamide and (RS)-α-[[[(R)-2-(1-tert-butoxyformamido)-2-(methoxycarbonyl)-1,1-dimethylethyl]sulfonyl]methyl]hydrocinnamic acid the tert-butyl [(R)-2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate, MS: 804 (M+H)+, and the epimeric tert-butyl [(R)-2-[[(S or R)-2-[[(S)-1-[[(1S,2R,3S)-1-(cyclohexylmethyl)-3-cyclopropyl-2,3-dihydroxypropyl]carbamoyl]-2-imidazole-4-ylethyl]carbamoyl]-3-phenylpropyl]sulfonyl]-1-(methoxycarbonyl)-2-methylpropyl]carbamate, MS: 804 (M+H)+, each as a colourless solid;

from (S)-α-amino-N-[(1S,2R,3S)-1-(cyclohexylmethyl)-3-cyclopropyl-2,3-dihydroxypropyl]imidazole-4-propionamide and (RS)-α-[[[(S)-2-(1-tert-butoxyformamido)-2-(methoxycarbonyl)-1,1-dimethylethyl]sulfonyl]methyl]hydrocinnamic acid the tert-butyl [(S)-2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl-2-methylpropyl]carbamate, MS: 804 (M+H)+, and the epimeric tert-butyl [(S)-2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate, MS: 804 (M+H)+, each as a colourless solid;

from (S)-α-amino-N-[(1S,2R,3S)-1-(cyclohexylmethyl)-3-cyclopropyl-2,3-dihydroxypropyl]imidazole-4-propionamide and (RS)-α-[[[(R)-2-(1-benzyloxy)formamido]-2-(methoxycarbonyl)-1,1-dimethylethyl]sulfonyl]methyl]hydrocinnamic acid the benzyl [(R)-2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate, MS: 838 (M+H)+, and the epimeric benzyl [(R)-2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate, MS: 838 (M+H)+, each as a colourless foam;

from (S)-α-amino-N-[(1S,2R,3S)-1-(cyclohexylmethyl)-3-cyclopropyl-2,3-dihydroxypropyl]imidazole-4-propionamide and (RS)-α-[[[(S)-2-(1-benzyloxy)formamido]-2-(methoxycarbonyl)-1,1-dimethylethyl]sulfonyl]methyl]hydrocinnamic acid the benzyl [(S)-2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate MS: 838 (M+H)+, and the epimeric benzyl [(S)-2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate, MS: 838 (M+H)+, each as a colourless foam.

The acids used as the starting materials were prepared as follows:

(RS)-α-[[[(RS)-2,3-Dihydroxypropyl]sulfonyl]methyl]hydrocinnamic acid:

(a) In an analogous manner to that described in Example 1, paragraphs (d) and (g), by adding 3-mercapto-1,2-propanediol to benzyl 2-benzylacrylate and subsequently oxidizing with potassium monopersulphate triple salt there was obtained benzyl (RS)-α-[[[(RS)-2-hydroxy-3-(pivaloyloxy)propyl]sulfonyl]methyl]hydrocinnamate, catalytic hydrogenation of which yielded (RS)-α-[[[(RS)-2,3-dihydroxypropyl]sulfonyl]methyl]hydrocinnamic acid as a colourless solid which was used directly in the next step.

(RS)-α-[[[(R)-2-(1-tert-Butoxyformamido)-2-(morpholinocarbonyl)ethyl]sulfonyl]methyl]hydrocinnamic acid:

(b) In an analogous manner to that described in Example 1, paragraphs (d) and g), by adding Boc-L-cysteine to benzyl 2-benzylacrylate and subsequently oxidizing with potassium monopersulphate triple salt there was obtained 3-[[(RS)-2-[(benzyloxy)carbonyl]-3-phenylpropyl]sulfonyl]-N-(tert-butoxycarbonyl)-L-alanine as a colourless oil, MS: 506 (M+H)+.

(c) In an analogous manner to that described in Example 1, by condensing 3-[[(RS)-2-[(benzyloxy)carbonyl]-3-phenylpropyl]sulfonyl]-N-(tert-butoxycarbonyl)-L-alanine and morpholine there was obtained tert-butyl [(R)-2-[[(RS)-2-[(benzyloxy)carbonyl]-3-phenylpropyl]sulfonyl]-2-(morpholinocarbonyl)ethyl]carbamate as a colourless solid; MS: 575 (M+H)+.

(d) In an analogous manner to that described in Example 1, paragraph (g), by catalytically hydrogenating tert-butyl [(R)-2--[[(RS)-2-[(benzyloxy)carbonyl]-3-phenylpropyl]sulfonyl]-2(morpholinocarbonyl)ethyl]carbamate there was obtained (RS)-α-[[[(R)-2-(1-tert-butoxyformamido)-2-(morpholinocarbonyl)ethyl]sulfonyl]methyl]hydrocinnamic acid as a colourless oil, MS: 485 (M+H)+.

(RS)-α-[[[(S)-2-(1-tert-Butoxyformamido)-2-(morpholinocarbonyl)ethyl]sulfonyl]methyl]hydrocinnamic acid:

(e) In an analogous manner to that described in Example 3, paragraphs (b)–(d), starting from Boc-D-cysteine and benzyl 2-benzylacrylate there was obtained 3-[[(RS)-2-[(benzyloxy)carbonyl]-3-phenyl propyl]sulfonyl]-N-(tert-butoxycarbonyl)-D- alanine as a colourless oil, MS: 506 (M+H)+. Subsequent condensation with morpholine yielded benzyl (RS)-α-[[[(S)-2-(1-tert-butoxyformamido)-2-(morpholinocarbonyl)ethyl]sulfonyl]methyl]hydrocinnamate, MS: 575 (M+H)+, as an oil, catalytic hydrogenation of which gave (RS)-α-[[[(S)-2-(1-tert-butoxyformamido)-2-(morpholinocarbonyl)ethyl]sulfonyl]methyl]hydrocinnamic acid as a colourless solid, MS: 485 (M+H)+.

rac-α-[[[2-(Morpholinocarbonyl)ethyl]sulfonyl]methyl]hydrocinnamic acid:

(f) In an analogous manner to that described in Example 1, paragraph (d), by adding 3-mercaptopropionic acid to benzyl 2-benzylacrylate and subsequently oxidizing with potassium monopersulphate triple salt there was obtained rac-3-[[[2-(benzyloxy)carbonyl]-3-phenylpropyl]sulfonyl]propionic acid as a colourless oil, MS: 391 (M+H)+.

(g) In an analogous manner to that described in Example 1, by condensing rac-3-[[[2-(benzyloxy)carbonyl]-3-phenylpropyl]sulfonyl]propionic acid and morpholine there was obtained benzyl rac-[[[2-(morpholinocarbonyl)ethyl]sulfonyl]methyl]hydrocinnamate as a colourless oil, MS: 460 (M+H)+.

(h) Catalytic hydrogenation of benzyl rac-[[[2-(morpholinocarbonyl)ethyl]sulfonyl]methyl]hydrocinnamate analogously to Example 1, paragraph (g), yielded rac-[[[2-(morpholinocarbonyl)ethyl]sulfonyl]methyl]hydrocinnamic acid as a colourless oil, MS: 370 (M+H)+.

(RS)-α-[[[(R)-2-(1-tert-Butoxyformamido)-2-(methoxycarbonyl)1,1-dimethylethyl]sulfonyl]methyl]hydrocinnamic acid:

(i) In an analogous manner to that described in Example 1, paragraph (d), by adding D-penicillamine methyl ester to benzyl 2-benzylacrylate there was obtained benzyl (RS)-α-[[[(R)-2-amino-2-(methoxycarbonyl)-1,1-dimethylethyl]thio]methyl]hydrocinnamic acid, MS: 416 (M+H)+, as an oil, the amino group of which was protected according to a general procedure known from the literature by reaction with di-tert-butyl dicarbonate. Subsequent oxidation with 3-chloroperbenzoic acid in methylene chloride gave benzyl (RS)-α-[[[(R)-2-(1-tert-butoxyformamido)-2-(methoxycarbonyl)-1,1-dimethylethyl]sulfonyl]methyl]hydrocinnamate as a colourless oil, MS: 448 (M—Boc+H)+.

(j) Catalytic hydrogenation of benzyl (RS)-α-[[[(R)-2-(1-tert-butoxyformamido)-2-(methoxycarbonyl)-1,1-dimethyl]sulfonyl]methyl]hydrocinnamate analogously to Example 1, paragraph (g), yielded (RS)-α-[[[(R)-2-(1-tert-butoxyformamido)2-(methoxycarbonyl)-1,1-dimethylethyl]sulfonyl]methyl]hydrocinnamic acid as a colourless solid, MS: 458 (M+H)+.

(RS)-α-[[[(S)-2-(1-tert-Butoxyformamido)-2-(methoxycarbonyl)-1,1-dimethylethyl]sulfonyl]methyl]hydrocinnamic acid:

(k) In an analogous manner to that described in Example 1, paragraph (d), by adding L-penicillamine methyl ester (J. Chem. Soc. Dalton Trans. 1984, 1333) to benzyl 2-benzylacrylate there was obtained benzyl (RS)-α-[[[(S)-2-amino-2-(methoxycarbonyl)1,1-dimethylethyl]thio]methyl]hydrocinnamate, MS: 416 (M+H)+, as an oil, the amino group of which was protected according to a general procedure known from the literature by reaction with di-tert-butyl dicarbonate. Subsequent oxidation with 3-chloroperbenzoic acid in methylene chloride gave benzyl (RS)-α-[[[(S)-2-(1-tert-butoxyformamido)-2-(methoxycarbonyl)-1,1-dimethylethyl]sulfonyl]methyl]hydrocinnamate as a colourless oil, MS: 448 (M-Boc+H)+. p1 (l) Catalytic hydrogenation of benzyl (RS)-α-[[[(S)-2-(1-tert-butoxy- formamido)-2-(methoxycarbonyl)-1,1-dimethylethyl]sulfonyl]-methyl]hydrocinnamate analogously to Example 1, paragraph (g), yielded (RS)-α-[[[(S)-2-(1-tert-butoxyformamido)-2-(methoxycarbonyl)-1,1dimethylethyl]sulfonyl]methyl]hydrocinnamic acid as a colourless solid, MS: 401 (M—C4H8)+.

(RS)-α-[[[(R)-2-(1-Benzyloxyformamido)-2-(methoxycarbonyl)-1,1-dimethylethyl]sulfonyl]methyl]hydrocinnamic acid:

(m) A solution of 1.0g (2.19mmol) of (RS)-α-[[[(R)-2-(1-tert-butoxyformamido)-2-(methoxycarbonyl)-1,1-dimethylethyl]sulfonyl]methyl]hydrocinnamic acid was added dropwise at room temperature to 10 ml of 1.4 M hydrogen chloride in dioxan and stirred for a further 12 hours. After evaporation of the solvent under reduced pressure there was obtained a colourless foam which, without further purification and characterization, was dissolved in 8.5 ml of 1N sodium hydrogen carbonate solution and treated with 0.44 ml (3.07 mmol) of benzyl chloroformate. The thus-obtained suspension was stirred at room temperature for 12 hours. Subsequently, it was extracted twice with 250 ml of ether each time, the combined ether extracts were dried over magnesium sulphate and evaporated under reduced pressure. For purification, the oily crude product (1.05 g) was chromatographed on 50 g of silica gel firstly with methylene chloride then with a 95:5 mixture of methylene chloride and methanol as the eluent. There were obtained 430 mg of (RS)-α-[[[(R)-2-(1-benzyloxyformamido)-2-(methoxycarbonyl)-1,1-dimethylethyl]sulfonyl]methyl]hydrocinnamic acid as a colourless foam, MS: 493 (M+H)+.

(RS)-α-[[[(S)-2-(1-Benzyloxyformamido)-2-(methoxycarbonyl)-1,1-dimethylethyl]sulfonyl]methyl]hydrocinnamic acid:

(n) In an analogous manner to that described in Example 3, paragraph (m), starting from (RS)-α-[[[(S)-2-(1-tert-butoxyformamido-2-(methoxycarbonyl)-1,1-dimethylethyl]sulfonyl]methyl]hydrocinnamic acid by cleavage of the Boc protecting group and introduction of the benzyloxycarbonyl protecting group there was obtained (RS)-α-[[[(S)-2-(1-benzyloxyformamido)-2-(methoxycarbonyl)-1,1-dimethylethyl]sulfonyl]methyl]hydrocinnamic acid as a colourless foam, MS: 493 (M+H)+.

EXAMPLE 4

A solution of 140 mg (0.17 mmol) of tert-butyl [(R)-2-[[(S or R)-2-[[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-(morpholinocarbonyl)ethyl]carbamate in 5 ml of 2N hydrochloric acid and 5 ml of methanol was stirred at 500 for 3 hours. Subsequently, the reaction solution was poured into 50 ml of 1N sodium hydrogen carbonate solution and extracted twice with 100 ml of ethyl acetate each time. The organic extracts were washed with 50 ml of water, thereafter combined, dried over magnesium sulphate and evaporated under reduced pressure. There were obtained 106 mg of (S)-α-[(S or R)-α-[[[(R)-2-amino-2-(morpholinocarbonyl)ethyl]sulfonyl]methyl]hydrocinnamamido]-N-[(1S,2R,3S)-1-(cyclohexylmethyl)-3-cyclopropyl-2,3-dihydroxypropyl]imidazole-4-propionamide as a colourless solid, MS: 731 (M+H)+.

EXAMPLE 5

The following compounds were manufactured by cleavage of the Boc protecting group in an analogous manner to that described in Example 4:

From tert-Butyl [(R)-2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]-sulfonyl]-2-(morpholinocarbonyl)ethyl]carbamate the (S)-α-[(R or S )-α-[[[(R)-2-amino-2-(morpholinocarbonyl)ethyl]sulfonyl]methyl]hydrocinnamamido]-N-[(1S,2R,3S)-1-(cyclohexylmethyl)- 3-cyclopropyl-2,3-dihydroxypropyl]imidazole-4-propionamide as a colourless solid, MS: 731 (M+H)+. ;

from tert-butyl [(S)-2-[[(S or R)-2-[[(S)-1-[[(1S,2R,3S)-1-(cyclohexylmethyl-3-cyclopropyl-2,3-dihydroxypropyl]carbamoyl]-2-imidazol-4-ylethyl]carbamoyl]-3-phenylpropyl]sulfonyl]-2-(morpholinocarbonyl)ethyl]carbamate the (S)-α-[(S or R)-α-[[[(S)-2-amino-2-(morpholinocarbonyl)ethyl]sulfonyl]methyl]hydrocinnamamido]-N-[(1S,2R,3S)-1-(cyclohexylmethyl)-3-cyclopropyl-2,3-dihydroxypropyl]imidazole-4-propionamide as a colourless solid, MS: 731 (M+H)+;

from tert-butyl [(S)-2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-(morpholinocarbonyl)ethyl]carbamate the (S)-α-[(R or S)-α-[[[(S)-2-amino-2-(morpholinocarbonyl)ethyl]sulfonyl]methyl]hydrocinnamamido]-N-[(1S,2R,3S)-1-(cyclohexylmethyl)-3-cyclopropyl-2,3-dihydroxypropyl]imidazole-4-propionamide as a colourless solid, MS: 731 (M+H)+.

EXAMPLE 6

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl]imidazole-4-propionamaide and (S)-α-[[[1-[(2-hydroxyethyl)carbamoyl]-1-methylethyl]sulfonyl]methyl]hydrocinnamic acid the (S)-N-[(1S,2R,3S)-1-(cyclohexylmethyl)-3-cyclopropyl-2,3-dihydroxypropyl]-α-[(S)-α-[[[1-[(2-hydroxyethyl)carbamoyl]-1-methylethyl]sulfonyl]methyl]hydrocinnamamido]imidazole-4-propionamide as a colourless, amorphous solid, MS: 704 (M+H)+;

from (S)-α-amino-N-[(1S,2R,3S)-1-(cyclohexylmethyl)-3-cyclopropyl-2,3-dihydroxypropyl]imidazole-4-propionamide and (S)-α-[[[1-(2-hydroxyl-(hydroxymethyl)-1-methylethyl]carbamoyl] -1-methylethyl]sulfonyl]methyl]hydrocinnamic acid the (S)-N-[(1S,2R,3S)-1-(cyclohexylmethyl)-3-cyclopropyl-2,3-dihydroxypropyl]-α-[(S)-α-[[[1-[[2-hydroxyl-1-(hydroxymethyl)-1-methylethyl]carbamoyl]-1 -methylethyl]sulfonyl]methyl]hydrocinnamamido]imidazole-4-propionamide as a colourless, amorphous solid, MS: 748 (M+H)+;

from (S)-α-amino-N-[(1S,2R,3S)-1-(cyclohexylmethyl)-3-cyclopropyl-2,3-dihydroxypropyl]imidazole-4-propionamide and 2-[2-[[(S)-2-carboxy-3-phenylpropyl]sulfonyl]-2-methylpropionamido]-2-deoxy-D-glucopyranose the 2-[2-[[(S)-2-[[(S)-1-[[(1S ,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose as a colourless, amorphous solid, MS: 822 (M+H)+.

The hydrocinnamic acid derivatives used as the starting materials were prepared as follows:

(S)-α-[[[1-[(2-Hydroxyethyl)carbamoyl]-1-methylethyl]sulfonyl]methyl]hydrocinnamic acid:

(a) In an analgous manner to that described in Example 1, paragraph (d), by adding 2-mercaptoisobutyric acid to ethyl 2-benzylacrylate (EPA 0236734) and subsequently oxidizing the thioether there was obtained rac-2-[[2-(ethoxycarbonyl)-3-phenylpropyl]sulfonyl]-2-methylpropionic acid as a colourless oil, MS: 342 (M)+.

(b) In an analogous manner to that described in Example 1, by condensing rac-2-[[2-(ethoxycarbonyl)-3-phenylpropyl]sulfonyl]-2-methylpropionic acid and ethanolamine there was obtained rac-α-[[[1-[(2-hydroxyethyl)carbamoyl]-1-methylethyl]sulfonyl]methyl]hydrocinnamic acid as a colourless oil, MS: 386 (M+H)+.

(c) 0.1N sodium hydroxide solution was added dropwise while stirring to a mixture of 0.86 g (2.23 mmol) of rac-α-[[[1-[(2 -hydroxyethyl)carbamoyl]-1-methylethyl]sulfonyl]methyl]hydrocinnamic acid and 200 mg of α-chymotrypsin in 5 ml of ethanol and 100 ml of water in such a manner that the pH value was held at 7.5. After sodium hydroxide solution was no longer consumed the working-up of the reaction mixture was effected by adjusting to pH 8 and extracting twice with 40 ml of ether each time. The combined organic extracts were washed with 15 ml of saturated sodium hydrogen carbonate solution, dried over sodium sulphate and evaporated under reduced pressure. There was obtained ethyl (R)-α-[[[1-[(2-hydroxyethyl)carbamoyl]-1-methylethyl]sulfonyl]methyl]hydrocinnamate as a yellowish oil.

The aqueous phase and the sodium hydrogen carbonate phase were combined, adjusted to pH 3 with 1N hydrochloric acid and extracted twice with 40 ml of ethyl acetate each time. The combined ethyl acetate extracts were dried over sodium sulphate and evaporated under reduced pressure. There were obtained 298 mg of (S)-α-[[[1-[(2-hydroxyethyl)carbamoyl]-1-methylethyl]sulfonyl]methyl]hydrocinnamic acid as a colourless solid, MS: 358 (M+H)+.

(S)-α-[[[1-[(2-Hydroxy-1-(hydroxymethyl)-1-methylethyl]carbamoyl]-1-methylethyl]sulfonyl]methy]hydrocinnamic acid:

(d) In an analogous manner to that described in Example 1, by condensing rac-2-[[2-(ethoxycarbonyl)-3-phenylpropyl]sulfonyl]-2-methylpropionic acid and 2-amino-2-methyl-l,3-propanediol there was obtained ethyl (RS)-α-[[[1-(2-hydroxy-1-(hydroxymethyl)-1-methylethyl]carbamoyl]-1-methylethyl]sulfonyl]methyl]hydrocinnamate as a colourless oil, MS: 430 (M+H)+. Subsequent enzymatic hydrolysis using α-chymotrypsin analogously to paragraph (c) above yielded (S)-α-[[[1-[(2-hydroxyl-(hydroxymethyl)-1-methylethyl]carbamoyl]-1
-methylethyl]sulfonyl]methyl]hydrocinnamic acid
as a colourless foam, MS: 402 (M+H)+.
2-[2-[[(S)-Carboxy-3-phenylpropyl]sulfonyl]-2-methylpropionamido]-2-deoxy-D-glucopyranose:

(e) In an analogous manner to that described in Example 1, by condensing rac-2-[[2-(ethoxycarbonyl)-3-phenylpropyl]sulfonyl]-2-methylpropionic acid and glucosamine there was obtained 2-deoxy-2-[2-[[(RS)-2-(ethoxycarbonyl)-3-phenylpropyl]sulfonyl]-2-methylpropionamido]-D-glucopyranose as a colourless amorphous solid, MS: 504 (M+H)+. Subsequent enzymatic hydrolysis analogously to paragraph (c) above yielded 2-[2-[[(S)-2-carboxy-3-phenylpropyl]sulfonyl]-2-methylpropionamido]-2-deoxy-D-glucopyranose as a colourless, amorphous solid, MS: 498 (M+Na)+.

EXAMPLE 7

77 mg (0.76mmol) of triethylamine, 118 mg (0.76mmol) of HOBT and 289 mg (0.76 mmol) of HBTU were added in sequence at room temperature under nitrogen to a solution of 250 mg (0.69mmol) of (S)-α-amino-N-[(1S,2R,3S)-1-(cyclohexylmethyl)-3-cyclopropyl-2,3-dihydroxypropyl]imidazole-4propionamide and 281 mg (0.76 mmol) of rac-α-[[[1-[(cyclopropylmethoxy)carbonyl]-1-methylethyl]sulfonyl]methyl]hydrocinnamic acid in 20 ml of dimethylformamide. The yellow reaction solution was stirred at room temperature overnight. For the working-up, the reaction solution was evaporated in a high vacuum. The residue was taken up in 40 ml of ethyl acetate and extracted twice with in each case 10 ml of saturated sodium hydrogen carbonate solution and 10 ml of saturated sodium chloride solution. The organic extracts were dried over sodium sulphate and subsequently evaporated under reduced pressure. For purification, the residue (560 mg) was chromatographed on 50 g of silica gel using a 95:5:0.1 mixture of methylene chloride, methanol and pyridine as the eluent. After lyophilization from dioxan/water there were obtained 110 mg of the less polar cyclopropylmethyl 2-[[(R)-2-[[-(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionate, MS: 715 (M+H)+, and 142 mg of the more polar epimeric cyclopropylmethyl 2-[[(S)-2-[[(S)-1-[[(1S,2R,3S)-1 -(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionate, MS: 715 (M+H)+, each as a colourless powder.

The rac-α-[[[1-[(cyclopropylmethoxy)carbonyl]-1-methylethyl]sulfonyl]methyl]hydrocinnamic acid used as the starting material was prepared as follows:

(a) In an analogous manner to that described in Example 2, paragraph (c), by reacting (RS)-2-[[2-[(benzyloxy)carbonyl]-3-phenylpropyl]sulfonyl]-2-methylpropionyl chloride and hydroxymethylcyclopropane in pyridine there was obtained benzyl rac-α-[[[1-[(cyclopropylmethoxy)carbonyl]-1-methylethyl]sulfonyl]methyl]hydrocinnamate as a colourless oil; MS: 459 (M+H)+.

(b) Catalytic hydrogenation of benzyl rac-α-[[[1-[(cyclopropylmethoxy)carbonyl]-1-methylethyl]sulfonyl]methyl]hydrocinnamate analogously to Example 1, paragraph (g), yielded rac-α-[[[1-[(cyclopropylmethoxy)carbonyl]-1-methylethyl]sulfonyl]methyl]hydrocinnamic acid as a colourless solid, MS: 386 (M+NH4)+.

EXAMPLE 8

The following compounds were manufactured in an analogous manner to that described in Example 7:

From (S)-α-amino-N-[(1S,2R,3S)-1-(cyclohexylmethyl)-3-cyclopropyl-2,3-dihydroxypropyl]imidazole-4-propionamide and rac-α-[[[1-[[2-(2-ethoxyethoxy)ethoxy]carbonyl]-1-methylethyl]sulfonyl]methyl]hydrocinnamic acid the 2-(2-ethoxyethoxy)ethyl 2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionate, MS: 777 (M+H)+, and the epimeric 2-(2-ethoxyethoxy)ethyl 2-[[(R or S)-2-[[(S)-1-[[(1S,2R,3S)-1 -(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionate, MS: 777 (M+H)+, each as a colourless, amorphous solid;

from (S)-α-amino-N-[(1S,2R,3S)-1-(cyclohexylmethyl)-3-cyclopropyl-2,3-dihydroxypropyl]imidazole-4-propionamide and rac-α-[[[1-methyl-1-[[(2-piperidinoethoxy)carbonyl]ethyl]sulfonyl]methyl]hydrocinnamaic acid the 2-piperidinoethyl 2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionate, MS: 772 (M+H)+, and the epimeric 2-piperidinoethyl 2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionate, MS: 772 (M+H)+, each as a colourless solid;

from (S)-α-amino-N-[(1S,2R,3S)-1-(cyclohexylmethyl)-3-cyclopropyl-2,3-dihydroxypropyl]imidazole-4-propionamide and (RS)-α-[[[1-[[[(RS)-2,2-dimethyl-1,3-dioxolan-4-yl]methoxy]carbonyl]-1-methylethyl]sulfonyl]methyl]hydrocinnamic acid the [(RS)-2,2-dimethyl-1,3-dioxolan-4-yl]methyl [[(S or R)-2-[[[(S)-1-[[(1S,2R,3S)-1-(cyclohexylmethyl)-3-cyclopropyl-2,3-dihydroxypropyl]carbamoyl]-2-imidazol-4-yl]ethyl]carbamoyl]-3-phenylpropyl]sulfonyl]-2-methylpropionate, MS: 775 (M+H)+, and the epimeric [(RS)-2,2-dimethyl-1,3-dioxolan-4-yl]methyl [[(R or S)-2-[[[(S)-1-[[(1S,2R,3S)-1-(cyclohexylmethyl)-3-cyclopropyl-2,3-dihydroxypropyl]carbamoyl]-2-imidazol-4- yl]ethyl]carbamoyl]-3-phenylpropyl]sulfonyl]-2-methylpropionate, MS: 775 (M+H)+, each as a colourless foam.

The hydrocinnamic acid derivatives used as the starting materials were prepared as follows:
rac-α-[[[1-[[2-(2-Ethoxyethoxy)ethoxy]carbonyl]-1-methylethyl]sulfonyl]methyl]hydrocinnamic acid:

(a) In an analogous manner to that of Example 2, paragraph (c), by reacting (RS)-2-[[2-[(benzyloxy)carbonyl]-3-phenylpropyl]sulfonyl]-2-methylpropionyl chloride and diethylene glycol monoethyl ether in pyridine there was obtained benzyl rac-α-[[[1-[[2-(2-ethoxyethoxy)ethoxy]carbonyl]-1-methylethyl]sulfonyl]methyl]hydrocinnamate as a colourless oil, MS: 385 (M-COObenzyl)+.

(b) Catalytic hydrogenation of benzyl rac-α-[[[1-[[2-(2-ethoxyethoxy)ethoxy]carbonyl]-1-methylethyl]- sulfonyl]methyl]hydrocinnamate analogously to Example 1, paragraph (g), yielded rac-α-[[[1-[[2-(2-ethoxyethoxy)ethoxy]carbonyl]-1-methylethyl]sulfonyl]methyl]hydrocinnamic acid as a colourless oil, MS: 430 (M+H)+.

rac-α-[[[1-Methyl-1-[(2-piperidinoethoxy)carbonyl]ethyl]sulfonyl]methyl]hydrocinnamic acid:

(c) In an analogous manner to that described in Example 2, paragraph (c), by reacting (RS)-2-[[2-[(benzyloxy)carbonyl]-3-phenylpropyl]sulfonyl]-2-methylpropionyl chloride and 1-(2hydroxyethyl)-piperidine there was obtained benzyl rac-α-[[[1-methyl-1-[(2-piperidinoethoxy)carbonyl]ethyl]sulfonyl]methyl]hydrocinnamate as a colourless oil, MS: 516 (M+H)+.

(d) Catalytic hydrogenation of benzyl rac-α-[[[1-methyl-1-[(2-piperidinoethoxy)carbonyl]ethyl]sulfonyl]methyl]hydrocinnamate analogously to Example 1, paragraph (g), yielded rac-α-[[[1-methyl-1-[(2-piperidinoethoxy)carbonyl]ethyl]sulfonyl]methyl]hydrocinnamic acid as a colourless foam which was used directly in the next step.

(RS)-α-[[[1-[[[(RS)-2,2-Dimethyl-1,3-dioxolan-4-yl]methoxy]carbonyl]-1-methylethyl]sulfonyl]methyl]hydrocinnamic acid:

(e) In an analogous manner to that described in Example 2, paragraph (c), by reacting (RS)-2-[[2-[(benzyloxy)carbonyl]-3-phenylpropyl]sulfonyl]-2-methylpropionyl chloride with DL-α-β-isopropylideneglycerol there was obtained benzyl (RS)-α-[[[1-[[[(R S )-2,2-dimethyl-1,3-dioxolan-4-yl]methoxy]carbonyl]-1 -methylethyl]sulfonyl]methyl]hydrocinnamate as a colourless oil, MS: 427 (M-benzyl)+.

(f) Catalytic hydrogenation of benzyl (RS)-α-[[[1-[[[(RS)-2,2-dimethyl-1,3-dioxolan-4-yl]methoxy]carbonyl]-1-methylethyl]sulfonyl]methyl]hydrocinnamate analogously to Example 1, paragraph (g), yielded (RS)-α-[[[1-[[[(RS)-2,2-dimethyl-1,3-dioxolan-4-yl]methoxy]carbonyl]-1-methylethyl]sulfonyl]methyl]hydrocinnamic acid as a colourless solid, MS: 428 (M)+.

EXAMPLE 9

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl-]imidazole-4-propionamide and rac-α-[[[1,1-dimethyl-2-(octadecanoyloxy)ethyl]sulfonyl]methyl]hydrocinnamic acid the 2-[[(R or S)-2-[[(S)-1-[[(1S,2R,3S)-1-(cyclohexylmethyl)o3-cyclopropyl-2,3-dihydroxypropyl]carbamoyl]-2-imidazol-4-ylethyl]carbamoyl]-3-phenylpropyl]sulfonyl]-2-methylpropyl octadecanoate, MS: 914 (M+H)+, and the epimeric 2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl octadecanoate, MS: 914 (M+H)+, each as a colourless solid;

- from (S)-α-amino-N-[(1S,2R,3S)-1-(cyclohexylmethyl)-3-cyclopropyl-2,3-dihydroxypropyl-]imidazole-4-propionamide and rac-α-[[[2-(methoxyacetoxy)-1,1-dimethylethyl]sulfonyl]methyl]hydrocinnamic acid the 2-[[(R or S)-2-[[(S)-1-[[(1S,2R,3S)-1-(cyclohexylmethyl)-3-cyclopropyl-2,3-dihydroxypropyl]carbamoyl]-2-imidazol-4-yl ethyl]carbamoyl]-3-phenylpropyl]sulfonyl]-2-methylpropyl methoxyacetate, MS: 719 (M+H)+, and the epimeric 2-[[(S or R)-2-[[(S)-1-[[(1S,2R,3S)-1 -cyclohexylmethyl)-3-cyclopropyl-2,3-dihydroxypropyl]carbamoyl]-2-imidazol-4-ylethyl]carbamoyl]-3-phenylpropyl]sulphonyl]-2-methylpropyl methoxyacetate, MS: 719 (M+H)+, each as a colourless solid;

from (S)-α-amino-N-[(1S,2R,3S)-1-(cyclohexylmethyl)-3-cyclopropyl-2,3-dihydroxypropyl-]imidazole-4-propionamide and rac-α-[[[2-(benzoyloxy)-1,1-dimethylethyl]sulfonyl]methyl]hydrocinnamic acid the 2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl benzoate, MS: 751 (M+H)+, and the epimeric 2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl benzoate, MS: 751 (M+H)+, each as a colourless, amorphous solid;

from (S)-α-amino-N-[(1S,2R,3S)-1-(cyclohexylmethyl)-3-cyclopropyl-2,3-dihydroxypropyl-]imidazole-4-propionamide and rac-2-[[[2-[(cyclopropylcarbonyl)oxy]-1,1-dimethylethyl]sulfonyl]-methyl]hydrocinnamic acid the 2-[[(R or S)-2-[[(S)-1-[[(1S ,2R,3S)-1-(cyclopropylmethyl)-3-cyclopropyl-2,3-dihydroxypropyl]carbamoyl]-2-imidazol-4-ylethyl]carbamoyl]-3-phenylpropyl]sulfonyl]-2-methylpropyl cyclopropanecarboxylate, MS: (M+H)+, and the epimeric 2-[[(S or R)-2-[[(S)-1-[(1S,2R,3S)-1-(cyclopropylmethyl)-3-cyclopropyl-2,3-dihydroxypropyl]carbamoyl]-2-imidazol-4-ylethyl]carbamoyl]-3-phenylpropyl]sulfonyl]-2-methylpropyl cyclopropanecarboxylate, MS: (M+H)+, each as a colourless, amorphous solid;

from (S)-α-amino-N-[(1S,2R,3S)-1-(cyclohexylmethyl)-3-cyclopropyl-2,3-dihydroxypropyl-]imidazole-4-propionamide and rac-α-[[[2-[N-(tert-butoxycarbonyl)glycyl]oxy]-1,1-dimethylethyl]sulfonyl]methyl]hydrocinnamic acid the N-(tert-butoxycarbonyl)glycine 2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3 -phenylpropyl]sulfonyl]-2-methylpropyl ester, MS: 804 (M+H)+, and the epimeric N-(tert-butoxycarbonyl)glycine 2-[[(R or S)-2-[[(S)-1-[[(1S ,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl ester, MS: 804 (M+H)+, each as a colourless, amorphous solid.

The hydrocinnamic acid derivatives used as the starting materials were prepared as follows:

rac-α-[[[1,1-Dimethyl-2-(octadecanoyloxy)ethyl]sulfonyl]methyl]hydrocinnamic acid:

(a) A solution of 9.4 g (22.2 mmol) of (RS)-2-[[2-[(benzyloxy)carbonyl]-3-phenylpropyl]sulfonyl]-2-methylpropionyl chloride in 45 ml of tetrahydrofuran was treated dropwise at 0° within 15 minutes with 2.3 ml (23.3 mmol) of 10M borane-dimethyl sulphide complex and subsequently stirred at room temperature for a further 3 hours. Thereafter, the mixture was cooled to 0° and then about 2 ml of methanol, 30 ml of water and 30 ml of saturated sodium hydrogen carbonate solution were added.

The mixture was then extracted three times with 35 ml of ether each time, finally the combined organic extracts were dried over sodium sulphate and evaporated under reduced pressure. The crude product was triturated with 50 ml of ether, there being obtained after suction filtration and drying 6.7 g of benzyl rac-α-[[(2-hydroxy-1,1-dimethylethyl)sulfonyl]methyl]hydrocinnamate as a colourless solid, MS: 408 (M+NH4)+.

(b) A solution of 420 mg (1.08 mmol) of benzyl rac-α-[[(2-hydroxy-1,1-dimethylethyl)sulfonyl]methyl]hydrocinnamate, 610 mg (2.15 mmol) of oleic acid, 710 mg (1.88 mmol) of HBTU and 660 mg (5.38 mmol) of 4-dimethylaminopyridine in 10 ml of methylene chloride was stirred at room temperature for 15 hours. The reaction solution was subsequently poured into 70 ml of ice-cold 2N sodium carbonate solution and extracted three times with 150 ml of ethyl acetate each time. The organic extracts were washed with 70 ml of ammonium chloride solution, then combined, dried over magnesium sulphate and evaporated under reduced pressure. For purification, the crude product (1.25 g) was chromatographed on 50 g of silica gel with a 95:5 mixture of toluene and ethyl acetate as the eluent. There were obtained 580 mg of benzyl rac-α-[[[1,1-dimethyl-2-[[(Z)-9octadecenoyl]oxy]ethyl]sulfonyl]methyl]hydrocinnamate as a colourless oil, MS: 655 (M+H)+.

(c) By catalytically hydrogenating benzyl rac-α-[[[1,1-dimethyl-2-[[(Z)-9-octadecenoyl]oxy]ethyl]sulfonyl]methyl]hydrocinnamate analogously to Example 1, paragraph (g), there was obtained rac-α-[[[1,1-dimethyl-2-(octadecanoyloxy)ethyl]sulfonyl]methyl]hydrocinnamic acid as a colourless oil, MS: 567 (M+H)+.

rac-α-[[[2-(Methoxyacetoxy)-1,1-dimethylethyl]sulfonyl]methyl]hydrocinnamic acid:

(d) A mixture of 422 mg (1.08 mmol) of benzyl rac-α-[[(2-hydroxyl-1,1-dimethylethyl)sulfonyl]methyl]hydrocinnamate, 2 ml (2.2 mmol) of methoxyacetyl chloride and 100 mg (0.8 mmol) of 4-dimethylaminopyridine in 2 ml of pyridine was stirred at 900 for 15 hours. Subsequently, the mixture was poured on to ice and 150 ml of 3N sulphuric acid and extracted three times with 300 ml of ether each time. The organic extracts were then washed with in each case 150 ml of ice-cold 3N sulphuric acid, water, 1M sodium hydrogen carbonate solution and saturated sodium chloride solution, then dried over magnesium sulphate and evaporated under reduced pressure. For purification, the crude product (540 mg of brown oil) was chromatographed on 50 g of silica gel with a 4:1 mixture of toluene and ethyl acetate. There were obtained 180 mg of benzyl rac-α-[[[2-(methoxyacetoxy)-1,1-dimethylethyl]sulfonyl]methyl]hydrocinnamate as a colourless oil, MS: 463 (M+H)+.

(e) By catalytically hydrogenating benzyl rac-α-[[[2-(methoxyacetoxy)-1,1-dimethylethyl]sulfonyl]methyl]hydrocinnamate analogously to Example 1, paragraph (g), there was obtained rac-α-[[[ 2-(methoxyacetoxy)-1,1-dimethylethyl]sulfonyl]methyl]hydrocinnamic acid as a colourless oil which was used directly in the next step.

rac-α-[[[2-(Benzyloxy)-1,1-dimethylethyl]sulfonyl]methyl]hydrocinnamic acid:

(f) In an analogous manner to that described in paragraph (d) above, by reacting benzoyl chloride with benzyl rac-α-[[(2-hydroxy-1,1-dimethylethyl)sulfonyl]methyl]hydrocinnamate in pyridine there was obtained benzyl rac-α-[[[2-(benzoyloxy)-1,1dimethylethyl]sulfonyl]methyl]hydrocinnamate as a colourless oil, MS: 403 (M-benzyl)+.

(g) Catalytic hydrogenation of benzyl rac-α-[[[2-(benzoyloxy)-1,1-dimethylethyl]sulfonyl]methyl]hydrocinnamate analogously to Example 1, paragraph (g), yielded rac-α-[[[2-(benzoyloxy)-1,1-dimethylethyl]sulfonyl]methyl]hydrocinnamic acid as a colourless solid, MS: 358 (M-HCOOH)+.

rac-2-[[[2-[(Cyclopropylcarbonyl)oxy]-1,1-dimethylethyl]sulfonyl]methyl]hydrocinnamic acid:

(h) In an analogous manner to that described in paragraph (d) above, by reacting cyclopropanecarbonyl chloride and benzyl rac-α-[[(2-hydroxy-1,1-dimethylethyl)sulfonyl]methyl]hydrocinnamate in pyridine there was obtained benzyl rac-[[[2-[(cyclopropylcarbonyl)oxy]-1,1-dimethylethyl]sulfonyl]methyl]hydrocinnamate as a colourless oil, MS: 367 (M-benzyl)+.

(i) Catalytic hydrogenation of benzyl rac-2-[[[2-[(cyclopropylcarbonyl)oxy]-1,1-dimethylethyl]sulfonyl]methyl]hydrocinnamate analogously to Example 1, paragraph (g), yielded rac-2-[[[2-[[[2-[(cyclopropylcarbonyl)oxy]-1,1-dimethylethyl]sulfonyl]methyl]hydrocinnamic acid as a colourless solid, MS: 322 (M-HCOOH)+.

rac-α-2-[[[2-[[N-(tert-Butoxycarbonyl)glycyl]oxy]-1,1-dimethylethyl]sulfonyl]methyl]hydrocinnamic acid:

(j) In an analogous manner to that described in paragraph (b) above, by condensing Boc-glycine and benzyl rac-α-[[2-hydroxy-1,1-dimethylethyl)sulfonyl]methyl]hydrocinnamate there was obtained N-(tert-butoxycarbonyl)glycine rac-2-[[2-[[2[(benzyloxy)carbonyl]-3-phenylpropyl]sulfonyl]-2-methylpropyl ester as a colourless oil, MS: 548 (M+H)+.

(k) Catalytic hydrogenation of N-(tert-butoxycarbonyl)glycine rac-2-[[2-[(benzyloxy)carbonyl]-3-phenylpropyl]sulfonyl]-2-methylpropyl ester analogously to Example 1, paragraph (g), yielded rac-α-2-[[[2-[[N-(tert-butoxycarbonyl)glycyl]oxy]-1,1-dimethylethyl]sulfonyl]methyl]hydrocinnamic acid as a colourless, amorphous solid, MS 458 (M+H)+.

EXAMPLE 10

The following compounds were manufactured in an analogous manner to that described in Example 1:

From (S)-α-[[[1-(morpholinocarbonyl)-1-methylethyl]sulfonyl]methyl]hydrocinnamic acid and (S)-2-amino-N-[(1S,2R,3 S)-1-(cyclohexylmethyl)-3-cyclopropyl-2,3-dihydroxypropyl]hexanamide the (S)-N-[(S)-1-[[(1S,2R,3S)-1-(cyclohexylmethyl)-3-cyclopropyl-2,3-dihydroxypropyl]carbamoyl]pentyl]-α-[[[1-methyl-1-(morpholinocarbonyl)ethyl]sulfonyl]methyl]hydrocinnamamide as a colourless foam, MS: 706 (M+H)+;

from (S)-α-[[[1-(morpholinocarbonyl)-1-methylethyl]sulfonyl]methyl]hydrocinnamic acid and (R)-2-amino-N-[(1S,2R,3S)-1-(cyclohexylmethyl)-3-cyclopropyl-2,3-dihydroxypropyl]-3-methylthio)-propionamide the (S)-N-[(R)-[[(1S,2R,3S)-1-(cyclohexylmethyl)-3-cyclopropyl-2,3-dihydroxypropyl]carbamoyl]-2-(methylthio )ethyl]-α-[[[1-

(morpholinocarbonyl)-1-methylethyl]sulfonyl]methyl]hydrocinnamamide as a colourless solid, MS: 710 (M+H)+.

The (S)-α-[[[1-(morpholinocarbonyl)-1-methylethyl]sulfonyl]methyl]hydrocinnamic acid used as the starting material was prepared as follows:

(a) In an analogous manner to that described in Example 1, paragraphs (e) and (f), by condensing rac-2-[[2-(ethoxycarbonyl)-3-phenylpropyl]sulfonyl]-2-methylpropionic acid and morpholine there was obtained ethyl rac-α-[[[1-(morpholinocarbonyl)-1-methylethyl]sulfonyl]methyl]hydrocinnamate as a colourless foam, MS: 411 (M)+, enzymatic hydrolysis of which using α-chymotrypsin analogously to Example 6, paragraph (c), yielded (S)-α-[[[1-(morpholinocarbonyl)-1-methylethyl]sulfonyl]methyl]hydrocinnamic acid as a colourless foam, MS: 383 (M)+.

The amines used as the starting materials were prepared as follows:

(S)-2-Amino-N-[(1S,2R,3S)-1-(cyclohexylmethyl)-3-cyclopropyl-2,3-dihydroxypropyl]hexanamide:

(b) Analogously to the procedure described in Example 1, paragraph (c), by condensing (1S,2R,3S)-3-amino-4-cyclohexyl-1-cyclopropyl-1,2-butanediol and Fmoc-norleucine there was obtained 9H-fluoren-9-ylmethyl [(S)-1-[[(1S,2R,3S)-1-(cyclohexylmethyl)-3-cyclopropyl-2,3-dihydroxypropyl]carbamoyl]pentyl]carbamate which, after reaction with piperidine in methylene chloride, yielded (S)-2-amino-N-[(1S,2R,3S)-1-(cyclohexylmethyl)-3-cyclopropyl-2,3-dihydroxypropyl]hexanamide as a colourless foam, MS: 322 (M−H₂)+.

(R)-2-Amino-N-[(1S,2R,3S)-1-(cyclohexylmethyl)-3-cyclopropyl-2,3-dihydroxypropyl]-3-(methylthio)propionamide:

(c) Analogously to the procedure described in Example 1, paragraph (c), by condensing (1S,2R,3S)-3-amino-4-cyclohexyl-1-cyclopropyl-1,2-butanediol and Fmoc-S-methylcysteine there was obtained 9H-fluoren-9-ylmethyl [(S)-1-[[(1S,2R,3S)-1-(cyclohexylmethyl)-3-cyclopropyl-2,3-dihydroxypropyl]carbamoyl]-2-[(methylthio)ethyl]carbamate which, after reaction with piperidine in methylene chloride yielded (R)-2-amino-N-[(1S,2R,3 S)-1-(cyclohexylmethyl)-3-cyclopropyl-2,3-dihydroxypropyl]-3-(methylthio)propionamide as a colourless solid, MS: 345 (M+H)+.

The Fmoc-S-methylcysteine used as the starting material was obtained according to the procedure for the preparation of Fmoc-amino acids generally known in the literature by reacting 9H-fluroenylmethylsuccinimidyl carbonate and S-methylcysteine.

EXAMPLE 11

The following compounds were manufactured in an analogous manner to that described in Example 1:

From (1S,2R,3S)-3-amino-4-cyclohexyl-1-cyclopropyl-1,2-butanediol and DL-2-hydroxy-N-[(S)-α-[[[(1-methyl-1-(morpholinocarbonyl)ethyl]sulfonyl]methyl]hydrocinnamoyl]glycine the (S)-N-[(R or S)-[[(1S,2R,3S)-1-(cyclohexylmethyl)-3-cyclopropyl-2,3-dihydroxypropyl]carbamoyl]hydroxymethyl]-α-[[[(1-methyl-1-(morpholinocarbonyl)ethyl]sulfonyl]methyl]hydrocinnamamide, MS: 666 (M+H)+, and the epimeric (S)-N-[(S or R)-[[(1S,2R,3S)-1-(cyclohexylmethyl)-3-cyclopropyl-2,3-dihydroxypropyl]carbamoyl]hydroxymethyl]-α-[[[(1-methyl-1-(morpholinocarbonyl)ethyl]sulfonyl]methyl]hydrocinnamamide, MS: 666 (M+H)+, each as a colourless solid;

from (1S,2R,3S)-3-amino-4-cyclohexyl-1-cyclopropyl-1,2-butanediol and D or L-2-ethoxy-N-[(S)-α-[[[(1-methyl-1-(morpholinocarbonyl)ethyl]sulfonyl]methyl]hydrocinnamoyl]glycine the (S)-N-[(R or S)-[[(1S,2R,3S)-1-(cyclohexylmethyl)-3-cyclopropyl-2,3-dihydroxypropyl]carbamoyl]ethoxymethyl]-α-[[[(1-methyl-1-(morpholinocarbonyl)ethyl]sulfonyl]methyl]hydrocinnamamide as a colourless solid, MS: 694 (M+H)+;

from (1S,2R,3S)-3-amino-4-cyclohexyl-1-cyclopropyl-1,2-butanediol and L or D-2-ethoxy-N-[(S)-α-[[[(1-methyl-1-(morpholinocarbonyl)ethyl]sulfonyl]methyl]hydrocinnamoyl]glycine the (S)-N-[(S or R)-[[(1S,2R,3S)-1-(cyclohexylmethyl)-3-cyclopropyl-2,3-dihydroxypropyl]carbamoyl]ethoxymethyl]-α-[[[(1-methyl-1-(morpholinocarbonyl)ethyl]sulfonyl]methyl]hydrocinnamamide as a colourless solid, MS: 694 (M+H)+;

from (1S,2R,3S)-3-amino-4-cyclohexyl-1-cyclopropyl-1,2-butanediol and DL-N-[(S)-α-[[[(1-methyl-1-(morpholinocarbonyl)ethyl]sulfonyl]methyl]hydrocinnamoyl]-2-(methylthio)glycine the (S)-N-[(RS)-[[(1S ,2R,3S)-1-(cyclohexylmethyl)-3-cyclopropyl-2,3-dihydroxypropyl]carbamoyl](methylthio)methyl)]-α-[[[(1-methyl-1-(morpholinocarbonyl)ethyl]sulfonyl]methyl]hydrocinnamamide as a colourless solid, MS: 696 (M+H)+;

from (1S,2R,3S)-3-amino-4-cyclohexyl-1-cyclopropyl-1,2-butanediol and D or L-2-(allyloxy)-N-[(S)-α-[[[1-methyl-1-(morpholinocarbonyl)ethyl]sulfonyl]methyl]hydrocinnamoyl]glycine the (S)-N-[(S or R)-(allyloxy)[[(1S,2R,3S)-1-(cyclohexylmethyl)-3-cyclopropyl-2,3-dihydroxypropyl]carbamoyl]methyl]-α-[[[1-methyl-1-(morpholinocarbonyl)ethyl]sulfonyl]methyl]hydrocinnamamide as a colourless solid, MS: 728 (M+Na)+.

from (1S,2R,3S)-3-amino-4-cyclohexyl-1-cyclopropyl-1,2-butanediol and L or D-2-(allyloxy)-N-[(S)-α-[[[1-methyl-1(morpholinocarbonyl)ethyl]sulfonyl]methyl]hydrocinnamoyl]glycine the (S)-N-[(R or S)-(allyloxy)[[(1S,2R,3S)-1-(cyclohexylmethyl)-3-cyclopropyl-2,3-dihydroxypropyl]carbamoyl]methyl]-α-[[[1-methyl-1-(morpholinocarbonyl)ethyl]sulfonyl]methyl]hydrocinnamamide as a colourless solid, MS: 728 (M+Na)+.

from (1S,2R,3S)-3-amino-4-cyclohexyl-1-cyclopropyl-1,2-butanediol and monomethyl (RS)-[(S)-α-[[[1-methyl-1-(morpholinocarbonyl)ethyl]sulfonyl]methyl]hydrocinnamido]malonate the methyl (RS)-N-[(1S,2R,3S)-1-(cyclohexylmethyl)-3-cyclopropyl-2,3-dihydroxypropyl]-2-[(S)-α-[[[1-methyl-1-(morpholinocarbonyl)ethyl]sulfonyl]methyl]hydrocinnamido]malonate, MS: 708 (M+H)+, and the (S)-N-[[[(1S,2R,3S)-1-(cyclohexylmethyl)-3-cyclopropyl-2,3-dihydroxypropyl]carbamoyl]methyl]-α-[[[1-methyl-1-(morpholinocarbonyl)ethyl]sulfonyl]methyl]hydrocinnamamide, MS: 650 (M+H)+, each as a colourless solid.

The acids used as the starting materials were prepared as follows:

DL-2-Hydroxy-N-[(S)-{x-[[[(1-methyl-1-(morpholinocarbonyl)ethyl]sulfonyl]methyl]hydrocinnamoyl]glycine:

(a) Analogously to the procedure described by Wang et al. in Synthesis 1989, 37 a mixture of 15.34 g (40mmol) of (S)-α-[[[(1-methyl-1-(morpholinocarbonyl)ethyl]sulfonyl]methyl]hydrocinnamic acid, 9.29 g (40 mmol) of dicyclohexylcarbodiimide and 6.89 g (50 mmol) of HOBT in 160 ml of methylene chloride and 40 ml of dimethylformamide was stirred at room temperature for 4 hours. Thereafter, the reaction mixture was filtered, the yellowish solution obtained was diluted with 200 ml of methylene chloride and cooled to 0°. Ammonia was conducted into this solution until it was saturated. The suspension obtained was stirred at room temperature for 1 hour. Subsequently, the solid formed was filtered off under suction and washed with 100 ml of methylene chloride. The yellow coloured filtrate was then washed twice with in each case 200 ml of water and twice with 200 ml of saturated sodium chloride solution. The wash solutions were extracted with 500 ml of methylene chloride. The combined organic phases were dried over sodium sulphate and thereafter evaporated under reduced pressure. For purification, the yellowish crude product obtained (15.3 g) was chromatographed on 1.3 kg of silica gel using a 4:1 mixture of ethyl acetate and hexane as the eluent. There were obtained 13.6 g of (S)-α-[[[(1-methyl-1-(morpholinocarbonyl)ethyl]sulfonyl]methyl]hydrocinnamamide as a colourless powder, MS: 383 $(M+H)^+$.

(b) By reacting glyoxylic acid monohydrate with (S)-α-[[[(1-methyl-1-(morpholinocarbonyl)ethyl]sulfonyl]methyl]hydrocinnamamide in acetone under reflux analogously to the procedure described in EPA 0343654 there was obtained DL-2-hydroxy-N-[(S)-α-[[[(1-methyl-1-(morpholinocarbonyl)ethyl]sulfonyl]methyl]hydrocinnamoyl]glycine, MS: 457 $(M+H)^+$, in the form of colourless crystals.

The following compounds were also prepared analogously to the procedure described in EPA 0343654:

D or L-2-Ethoxy-N-[(S)-α-[[[(1-methyl-1-(morpholinocarbonyl)ethyl]sulfonyl]methyl]hydrocinnamoyl]glycine and L or D-2-ethoxy-N-[(S)-α-[[[(1-methyl-1-(morpholinocarbonyl)ethyl]sulfonyl]methyl]hydrocinnamoyl]glycine:

(c) By reacting DL-2-hydroxy-N-[(S)-α-[[[(1-methyl-1(morpholinocarbonyl)ethyl]sulfonyl]methyl]hydrocinnamoyl]glycine with ethanol and sulphuric acid, followed by a chromatographic separation of the two diastereomeric esters the L or D-2-(ethylthio)-N-[(S)-α-[[[1-methyl-1-(morpholinocarbonyl)ethyl]sulfonyl]methyl]hydrocinnamoyl]glycine ethyl ester, MS: 513 $(M+H)^+$, and the D or L-2-(ethlythio)-N-[(S)-α-[[[1-methyl-1-morpholinocarbonyl)ethyl]sulfonyl]methyl]hydrocinnamoyl]glycine ethyl ester, MS: 513 $(M+H)^+$, each as a colourless solid.

(d) By hydrolyzing L or D-2-(ethylthio)-N-[(S)-α-[[[1-methyl-1(morpholinocarbonyl)ethyl]sulfonyl]methyl]hydrocinnamoyl]glycine ethyl ester with 1N sodium hydroxide in ethanol the D or L-2-ethoxy-N-[(S)-α-[[[1-methyl-1-(morpholinocarbonyl)ethyl]sulfonyl]methyl]hydrocinnamoyl]glycine, MS: 507 $(M+Na)^+$, as a colourless solid.

(e) By hydrolysing D or L-2-(ethylthio)-N-[(S)-α-[[[1-methyl-1-(morpholinocarbonyl)ethyl]sulfonyl]methyl]hydrocinnamoyl]glycine ethyl ester with 1N sodium hydroxide in ethanol the L or D-2-ethoxy-N-[(S)-α-[[[1-methyl-1-(morpholinocarbonyl)ethyl] sulfonyl]methyl]hydrocinnamoyl]glycine, MS: 507 $(M+Na)^+$, as a colourless solid.

DL-N-[(S)-α-[[[1-Methyl-1-(morpholinocarbonyl)ethyl]sulfonyl]methyl]hydrocinnamoyl]-2-(methylthio)glycine:

(f) By reacting DL-2-hydroxy-N-[(S)-α-[[[(1-methyl-1-(morpholinocarbonyl)ethyl]sulfonyl]methyl]hydrocinnamoyl]glycine with ethyl mercaptan and sulphuric acid in glacial acetic acid the DL-N-[(S)-α-[[[1-Methyl-1-(morpholinocarbonyl)ethyl]sulfonyl]methyl]hydrocinnamoyl]-2-(methylthio)glycine, MS: 487 $(M+H)^+$, as a colourless solid.

D or L-2-(Allyloxy)-N-[(S)-α-[[[1-methyl-1-(morpholinocarbonyl)ethyl]sulfonyl]methyl]hydrocinnamoyl]glycine and L or D-2-(allyloxy)-N-[(S)-α-[[[1-methyl-1-(morpholinocarbonyl)ethyl]sulfonyl]methyl]hydrocinnamoyl]glycine:

(g) By reacting DL-2-hydroxy-N-[(S)-α-[[[(1-methyl-1-(morpholinocarbonyl)ethyl]sulfonyl]methyl]hydrocinnamoyl]glycine with allyl alcohol and sulphuric acid followed by a chromatographic separation of the two diastereomeric esters the L or D-2-(allyloxy)-N-[(S)-α-[[[1-methyl-1-(morpholinocarbonyl)ethyl]sulfonyl]methyl]hydrocinnamoyl]glycine allyl ester, MS: 645 [M+H+thioglycerol (=matrix)]$^+$, and the D or L-2-(allyloxy)-N-[(S)-α-[[[1-methyl-1-(morpholinocarbonyl)ethyl]sulfonyl]methyl]hydrocinnamoyl]glycine allyl ester, MS: 645 [M+H+thioglycerol (=matrix)]$^+$, each as a colourless solid.

(h) By hydrolyzing L or D-2-(allyloxy)-N-[(S)-α-[[[1-methyl-1-(morpholinocarbonyl)ethyl]sulfonyl]methyl]hydrocinnamoyl]glycine allyl ester with 1N sodium hydroxide in dioxan the D L-2-(allyloxy)-N-[(S)-α-[[[1-methyl-1-(morpholinocarbonyl)ethyl]sulfonyl]methyl]hydrocinnamoyl]glycine, MS: 627 [M+Na+thioglycerol (=matrix)]$^+$, as a colourless solid.

(i) By hydrolysing D or L-2-(allyloxy)-N-[(S)-α-[[[1-methyl-1-(morpholinocarbonyl)ethyl]sulfonyl]methyl]hydrocinnamoyl] glycine allyl ester with 1N sodium hydroxide in dioxan the L or D-2-(allyloxy)-N-[(S)-α-[[[1-methyl-1-(morpholinocarbonyl)ethyl]sulfonyl]methyl]hydrocinnamoyl]glycine, MS 627 [M+Na+thioglycerol (=matrix)]$^+$, as a colourless solid.

Monomethyl (RS)-[(S)-α-[[[1-methyl-1-(morpholinocarbonyl)ethyl]sulfonyl]methyl]hydrocinnamamido]malonate:

(j) By condensing ethyl (S)-α-[[[1-methyl-1-(morpholinocarbonyl)ethyl]sulfonyl]methyl]hydrocinnamate and dimethyl aminomalonate the dimethyl [(S)-α-[[[(1-methyl-1-(morpholinocarbonyl)ethyl]sulfonyl]methyl]hydrocinnamamido]malonate, MS: 513 $(M+H)^+$, as a colourless solid.

(k) By hydrolyzing dimethyl [(S)-α-[[[(1-methyl-1-(morpholinocarbonyl)ethyl]sulfonyl]methyl]hydrocinnamamido]malonate with 1N sodium hydroxide in methanol the monomethyl (RS)-[(S)-α-[[[1-methyl-1-(morpholinocarbonyl)ethyl]sulfonyl]methyl]hydrocinnamamido]malonate, MS: 499 $(M+H)^+$, as a colourless solid.

EXAMPLE 12

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl]imidazole-4-propionamide and rac-α-[[[2-[(isopropylcarbamoyl)oxy]-1,1-dimethylethyl]sulfonyl]methyl]hydrocinnamic acid the 2-[[(S or R)-2-[[(S)-1-[[((1S ,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl isopropylcarbamate, MS: 732 (M+H)+, and the epimeric 2-[[(R or S)-2-[[(S)-1-[[((1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl isopropylcarbamate, MS: 732 (M+H)+, each as a colourless solid;

from (S)-α-amino-N-[(1S,2R,3S)-1-(cyclohexylmethyl)-3-cyclopropyl-2,3-dihydroxypropyl]imidazole-4-propionamide and rac-α-[[[2-[(tert-butylcarbamoyl)oxy]-1,1-dimethylethyl]sulphonyl]methyl]hydrocinnamic acid the 2-[[(R or S)-2-[[(S)-1-[(1S,2R,3S)-1-(cyclohexylmethyl)-3-cyclopropyl-2,3-dihydroxypropyl]carbamoyl]-2-imidazol-4-ylethyl]carbamoyl]-3-phenyl]propyl]sulfonyl]-2-methylpropyl tert-butylcarbamate, MS: 746 (M+H)+, as a colourless solid, and the 2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl tert-butylcarbamate, MS: 746 (M+H)+, as a colourless, amorphous solid.

The hydrocinnamic acids used as the starting materials were prepared as follows:

rac-α-[[[2-[(Isopropylcarbamoyl)oxy]-1,1-dimethylethyl]sulfonyl]methyl]hydrocinnamic acid:

(a) A solution of 1.0 g (2.56 mmol) of benzyl rac-α-[[(2-hydroxy-1,1-dimethylethyl)sulfonyl]methyl]hydrocinnamate and 0.97 g (10.24 mmol) of isopropyl isocyanate in 20 ml of dry toluene was heated to 100o for 4 hours. Subsequently, the reaction solution was evaporated under reduced pressure. The benzyl rac-α-[[[2-[(isopropylcarbamoyl)oxy]-1,1-dimethylethyl]sulfonyl]methyl]hydrocinnamate was obtained in quantitative yield as a yellowish oil, MS: 384 (M-benzyl)+.

(b) In an analogous manner to that described in Example 1, paragraph (g), by catalytically hydrogenating benzyl rac-α-[[[2-[(isopropylcarbamoyl)oxy]-1,1-dimethylethyl]sulfonyl]methyl]hydrocinnamate there was obtained rac-α-[[[2-[(isopropylcarbamoyl)oxy]-1,1-dimethylethyl]sulfonyl]methyl]hydrocinnamic acid in quantitative yield as an amorphous solid, MS: 300 [M−O=C=N-isopropyl)]+. rac-α-[[[2-[(tert-Butylcarbamoyl)oxy]-1,1-dimethylethyl]sulfonyl]methyl]hydrocinnamic acid:

(c) In an analogous manner to that described in paragraph (a) above, by reacting benzyl rac-α-[[(2-hydroxy-1,1-dimethylethyl)sulfonyl]methyl]hydrocinnamate and tert-butyl isocyanate there was obtained benzyl rac-α-[[[2-[(tert-butylcarbamoyl)oxy]-1,1-dimethylethyl]sulfonyl]methyl]hydrocinnamate in quantitative yield as a colourless solid, MS: 490 (M+H)+.

(d) Catalytic hydrogenation of benzyl rac-α-[[[2-[(tert-butylcarbamoyl)oxy]-1,1-dimethylethyl]sulfonyl]methyl]hydrocinnamate analogously to Example 1, paragraph (g), yielded rac-α-[[[2-[(tert-butylcarbamoyl)oxy]-1,1-dimethylethyl]sulfonyl]methyl]hydrocinnamic acid as a colourless solid, MS: 400 (M+H)+.

EXAMPLE 13

In an analogous manner to that described in Example 1, by condensing (S)-α-[[[1-methyl-1-(morpholinocarbonyl)ethyl]sulfonyl]methyl]hydrocinnamic acid and (S)-α-amino-N-[(1S ,2R,3S)-1-(cyclohexylmethyl)-2,3-dihydroxy-5-methylhexyl]-imidazole-4-propionamide (EPA 0189203) there was obtained (S)-N-[(1S,2R,3S)-1-(cyclohexylmethyl)-2,3-dihydroxy-5-methylhexyl]-α-[(S)-α-[[[(1-methyl-1-(morpholinocarbonyl)ethyl]sulfonyl]methyl]hydrocinnamamido]imidazole-4-propionamide as a colourless resin, MS: 746 (M+H)+.

EXAMPLE 14

In an analogous manner to that described in Example 1, by condensing (S)-α-[[[1-methyl-1-(morpholinocarbonyl)ethyl]sulfonyl]methyl]hydrocinnamic acid and (S)-α-amino-N-[(1S,2R,3S)-1-(cyclohexylmethyl)-2,3-dihydroxy-4-methylpentyl]imidazole-4-propionamide (EPA 0332008) there was obtained (S)-N-[(1S,2R,3S)-1-(cyclohexylmethyl)-2,3-dihydroxy-4-methylpentyl]-α-[(S)-α-[[[(1-methyl-1-(morpholinocarbonyl)ethyl] sulfonyl]methyl]hydrocinnamamido]imidazole-4-propionamide as a colourless resin, MS: 732 (M+H)+.

EXAMPLE 15

The following compounds were manufactured in an analogous manner to that described in Example 1:

From (S)-α-amino-N-[(1S,2R,3S)-1-(cyclohexylmethyl)-3-cyclopropyl-2,3-dihydroxypropyl]imidazole-4-propionamide and (S)-α-[[[1-methyl-1-(morpholinocarbonyl)ethyl]sulfonyl]methyl]-3-(naphthalen-1-yl)propionic acid the (S)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]-3-(naphthalen-1-yl)propionamido]imidazole-4-propionamide as a colourless foam, MS: 780 (M+H)+;

from (S)-α-amino-N-[(1S,2R,3S)-1-(cyclohexylmethyl)-3-cyclopropyl-2,3-dihydroxypropyl]imidazole-4-propionamide and (S)-p-fluoro-α-[[[1-methyl-1-(morpholinocarbonyl)ethyl]sulfonyl]methyl]hydrocinnamic acid the (S)-N-[(1S,2R,3S)-1-(cyclohexylmethyl)-3-cyclopropyl-2,3-dihydroxypropyl]-α-[(S)-p-fluoro-α-[[[1-methyl-1-(morpholinocarbonyl)ethyl]sulfonyl]methyl]hydrocinnamamido]imidazole-4-propionamide as a colourless foam, MS: 748 (M+H)+;

from (S)-α-amino-N-[(1S,2R,3S)-1-(cyclohexylmethyl)-3-cyclopropyl-2,3-dihydroxypropyl]imidazole-4-propionamide and (S)-α-[[[1-methyl-1-(morpholinocarbonyl)ethyl]sulfonyl]methyl]-3-(thiophen-2-yl)propionic acid the (S)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]-3-(thiophen-2-yl)propionamido]imidazole-4-propionamide as a colourless foam, MS: 736 (M+H)+;

from (S)-α-amino-N-[(1S,2R,3S)-1-(cyclohexylmethyl)-3-cyclopropyl-2,3-dihydroxypropyl]imidazole-4-propionamide and (S)-α-[[[1-methyl- 1-(morpholinocarbonyl)ethyl]sulfonyl]-methyl]cyclohexanepropionic acid the (S)-N-[(1S,2R,-3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]-3-cyclohexylpropionamido]imidazole-4-propionamide as a colourless foam, MS: 736 (M+H)+.

The acids used as the starting materials were prepared as follows:

(S)-α-[[[1-Methyl-1-(morpholinocarbonyl)ethyl]sulfonyl]methyl]-3-(naphthalen-1-yl)propionic acid:

In an analogous manner to that described in Example 1, paragraphs (d) and (e), and Example 2, paragraph (a), starting from 2-mercaptoisobutyric acid and ethyl 2-methylene-3-(naphthalen-1-yl)propionate there was obtained ethyl (R,S)-α-[[[1-methyl-1-(morpholinocarbonyl)ethyl]sulfonyl]methyl]-3-(naphthalen-1-yl)propionate which was saponified enzymatically in an analogous manner to that described in Example 6, paragraph (c), and thus yielded (S)-α-[[[1-methyl-1-(morpholinocarbonyl)ethyl]sulfonyl]methyl]-3-(naphthalen-1-yl)propionic acid, MS: 456 (M+H)+.

(S)-p-Fluoro-α-[[[1-methyl-1-(morpholinocarbonyl)ethyl]sulfonyl]methyl]hydrocinnamic acid:

In an analogous manner to that described in Example 1, paragraphs (d) and (e), and Example 2, paragraph (a), starting from 2-mercaptoisobutyric acid and ethyl 3-(4-fluorophenyl)-2-methylenepropionate there was obtained ethyl (R,S)-p-fluoro-α-[[[1-methyl-1-(morpholinocarbonyl)ethyl]sulfonyl]methyl]hydrocinnamate which was saponified enzymatically in an analogous manner to that described in Example 6, paragraph (c), and thus yielded (S)-p-fluoro-α-[[[1-methyl-1-(morpholinocarbonyl)ethyl]sulfonyl]methyl]hydrocinnamic acid, MS: 402 (M+H)+.

(S)-α-[[[1-Methyl-1-(morpholinocarbonyl)ethyl]sulfonyl]methyl]-3-(thiophen-2-yl)propionic acid:

In an analogous manner to that described in Example 1, paragraph (d) and (e), and Example 2, paragraph (a), starting from 2-mercaptoisobutyric acid and ethyl 2-methylene-3-(thiophen-2yl)propionate there was obtained ethyl (R,S)-α-[[[1-methyl-1-(morpholinocarbonyl)ethyl]sulfonyl]methyl]-3-(thiophen-2yl)propionate which was saponified enzymatically in an analogous manner to that described in Example 6, paragraph (c), and thus yielded (S)-α-[[[1-methyl-1-(morpholinocarbonyl)ethyl]sulfonyl]methyl]-3-(thiophen-2-yl)propionic acid, MS: 390 (M+H)+.

(S)-α-[[[1-Methyl-1-(morpholinocarbonyl)ethyl]sulfonyl]methyl]cyclohexanepropionic acid:

In an analogous manner to that described in Example 1, paragraphs (d) and (e), starting from 2-mercaptoisobutyric acid and ethyl 2-benzylacrylate there was obtained (RS)-2-[[2-[(ethoxy)carbonyl]-3-phenylpropyl]sulfonyl]-2-methylpropionyl chloride, reaction of which with morpholine analogously to Example 2, paragraph (a), and subsequent enzymatic hydrolysis analogously to Example 6, paragraph (c), yielded (S)-α-[[[1-methyl-1-(morpholinocarbonyl)ethyl]sulfonyl]methyl]hydrocinnamic acid, MS: 383 (M)+, as a colourless solid.

A solution of 610mg (1.59mmol) (S)-α-[[[1-methyl-1-(morpholinocarbonyl)ethyl]sulfonyl]methyl]hydrocinnamic acid in 20 ml of methanol was hydrogenated in the presence of 60 mg of rhodium on aluminium oxide at 500 for 4 hours at a pressure of $10^6$ Pa of hydrogen. Subsequently, the catalyst was filtered off and rinsed with methanol. The methanolic solution was evaporated under reduced pressure, whereby 580 mg of (S)-α-[[[1-methyl-1-(morpholinocarbonyl)ethyl]sulfonyl]methyl]cyclohexanepropionic acid, MS: 346 $(M-C_3H_7)^+$ were obtained as a colourless crystalline solid.

EXAMPLE 16

The following compounds were manufactured in an analogous manner to that described in Example 1:

From (S or R)-α-amino-N-[(1S,2R,3S)-1-(cyclohexylmethyl)-3-cyclopropyl-2,3-dihydroxypropyl]-3-(pyridin-3-yl)propionamide and (S)-α-[[[1-methyl-1-(morpholinocarbonyl)ethyl]sulfonyl]methyl]hydrocinnamic acid the (S or R)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(pyridin-3-yl)propionamide as a colourless foam, MS: 741 (M+H)+;

from (R or S)-α-amino-N-[(1S,2R,3S)-1-(cyclohexylmethyl)-3-cyclopropyl-2,3-dihydroxypropyl]-3-(pyridin-3-yl)propionamide and (S)-α-[[[1-methyl-1-(morpholinocarbonyl)ethyl]sulfonyl]methyl]hydrocinnamic acid the (R or S)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(pyridin-3-yl)propionamide as a colourless foam, MS: 741 (M+H)+;

from (S or R)-α-amino-N-[(1S,2R,3S)-1-(cyclohexylmethyl)-3-cyclopropyl-2,3-dihydroxypropyl]-3-(pyridin-2-yl)propionamide and (S)-α-[[[1-methyl-1-(morpholinocarbonyl)ethyl]sulfonyl]methyl]hydrocinnamic acid the (S or R)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(pyridin-2-yl)propionamide as a colourless foam, MS: 741 (M+H)+;

from (R or S)-α-amino-N-[(1S,2R,3S)-1-(cyclohexylmethyl)-3-cyclopropyl-2,3-dihydroxypropyl]-3-(pyridin-2-yl)propionamide and (S)-α-[[[1-methyl-1-(morpholinocarbonyl)ethyl]sulfonyl]methyl]hydrocinnamic acid the (R or S)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]           -sulfonyl]methyl]hydrocinnamamido]-3-(pyridin-2-yl)propionamide as a colourless foam, MS: 741 (M+H)+;

from (S or R)-α-amino-N-[(1S,2R,3S)-1-(cyclohexylmethyl)-3-cyclopropyl-2,3-dihydroxypropyl]-3-(pyridin-4-yl)propionamide and (S)-α-[[[1-methyl-1-(morpholinocarbonyl)ethyl]sulfonyl]methyl]hydrocinnamic acid the (S or R)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(pyridin-4-yl)propionamide as a colourless foam, MS: 741 (M+H)+;

from (R or S)-α-amino-N-[(1S,2R,3S)-1-(cyclohexylmethyl)-3-cyclopropyl-2,3-dihydroxypropyl]-3-(pyridin-4-yl)propionamide and (S)-α-[[[1-methyl-1-(morpholinocarbonyl)ethyl]sulfonyl]methyl]hydrocinnamic acid the (R or S)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-

3-(pyridin-4-yl)propionamide as a colourless foam, MS: 741 (M+H)+;

from (S)-α-amino-N-[(1S,2R,3S)-1-(cyclohexylmethyl)-3-cyclopropyl-2,3-dihydroxypropyl]-3-(pyrazol-1-yl)propionamide and (S)-α-[[[1-methyl-1-(morpholinocarbonyl)ethyl]sulfonyl]methyl]hydrocinnamic acid the (S)-N-[(1S,2R,3S)-1-(cyclohexylmethyl)-3-cyclopropyl-2,3-dihydroxypropyl]-α-[(S)-a-[[[1-methyl-1-(morpholinocarbonyl)ethyl]sulfonyl]methyl]hydrocinnamamido]-3-(pyrazol-1-yl)propionamide as a colourless foam, MS: 730 (M+H)+;

from (S)-α-amino-N-[(1S,2R,3S)-1-(cyclohexylmethyl)-3-cyclopropyl-2,3-dihydroxypropyl]-3-(imidazol-1-yl)propionamide and (S)-α-[[[1-methyl-1-(morpholinocarbonyl)ethyl]sulfonyl]methyl]hydrocinnamic acid the (S)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(imidazol-1-yl)propionamide as a colourless foam, MS: 730 (M+H)+;

from (RS)-α-amino-N-[(1S,2R,3S)-1-(cyclohexylmethyl)-3-cyclopropyl-2,3-dihydroxypropyl]-3-(thiophen-2-yl)propionamide and (S)-α-[[[1-methyl-1-(morpholinocarbonyl)ethyl]sulfonyl]methyl]hydrocinnamic acid the less polar (S or R)-N-[(1S,2R,3S)-1-(cyclohexylmethyl)o3-cyclopropyl-2,3-dihydroxypropyl]-α-[(S)-α-[[[1-methyl-1-(morpholinocarbonyl)ethyl]sulfonyl]methyl]hydrocinnamamido]-3-(thiophen-2-yl)propionamide, MS: 746 (M+H)+, and the more polar epimer (R or S)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(thiophen-2-yl)propionamide, MS: 746 (M+H)+, each as a colourless foam;

from (RS)-α-amino-N-[(1S,2R,3S)-1-(cyclohexylmethyl)-3-cyclopropyl-2,3-dihydroxypropyl]-3-(furan-2-yl)propionamide and (S)-α-[[[1-methyl-1-(morpholinocarbonyl)ethyl]sulfonyl]methyl]hydrocinnamic acid the less polar (S or R)-N-[-(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(furan-2-yl)propionamide, MS: 730 (M+H)+, and the more polar epimer (R or S)-N-[-(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(furan-2-yl)propionamide, MS: 730 (M+H)+, each as a colourless foam.

The amines used as the starting materials were prepared as follows:

(S or R)- and (R or S)-α-Amino-N-[(1S,2R,3S)-1-(cyclohexylmethyl)-3-cyclopropyl-2,3-dihydroxypropyl]-3-(pyridin-3-yl)propionamide:

1.27 g (3.3 mmol) of HBTU and 0.45 ml (3.3 mmol) of triethylamine were added to a solution of 878 mg (3.3 mmol) of N-(tert-butoxycarbonyl)-3-(pyridin-3-yl)-D,L-alanine [J. Gen. Chem. USSR, 40, 2488 (1970)]and 750 mg (3.3 mmol) of (1S,2R,3S)-3-amino-4-cyclohexyl-1-cyclopropyl-1,2-butanediol in 33 ml of acetonitrile and the mixture was stirred at room temperature overnight. The colourless crystals obtained after filtration were dissolved in 30 ml of ethanol and 23.3 ml of 1N hydrochloric acid were added thereto. After 24 hours at 50° the solution was made basic with 2N sodium hydroxide solution and evaporated under reduced pressure, and the residue was partitioned between water and ethyl acetate. The aqueous phase was extracted three times with ethyl acetate, the combined organic phases were dried with magnesium sulphate, filtered and evaporated under reduced pressure. Chromatography of the residue (silica gel, methylene chloride/methanol/ammonia 140/10/1) yielded 315 mg of (S or R)-α-amino-N-[(1S,2R,3S)-1-cyclohexylmethyl)-3-cyclopropyl-2,3-dihydroxypropyl]-3-(pyridin-3-yl)propionamide, MS: 267 (M+H)+, as a colourless foam, as well as 315 mg of (R or S)-α-amino-N-[(1S,2R,3S)-1-(cyclohexylmethyl)-3-cyclopropyl-2,3-dihydroxypropyl]-3-(pyridin-3-yl)propionamide, MS: 267 (M+H)+, as a colourless foam.

(S or R)- and (R or S)-α-Amino-N-[(1S,2R,3S)-1-(cyclohexylmethyl)-3-cyclopropyl-2,3-dihydroxypropyl]-3-(pyridin-2-yl)propionamide:

In an analogous manner to that described above, by the condensation of N-(tert-butoxycarbonyl)-3-(pyridin-2-yl)-D,L-alanine [J. Gen. Chem. USSR, 40, 2488 (1970)1 and (1S,2R,3S)-3-amino-4-cyclohexyl-1-cyclopropyl-1,2-butanediol followed by acidic hydrolysis there were obtained (S or R)-α-amino-N-[(1S,2R,3 S)-1-(cyclohexylmethyl)-3-cyclopropyl-2,3-dihydroxypropyl]-3-(pyridin-2-yl)propionamide, MS: 267 (M+H)+, and (R or S)-α-amino-N-[(1S,2R,3S)-1-(cyclohexylmethyl)-3-cyclopropyl-2,3-dihydroxypropyl]-3-(pyridin-2-yl)propionamide, MS: 267 (M+H)+, each as a colourless foam.

(S or R)- and (R or S)-α-Amino-N-[(1S,2R,3S)-1-(cyclohexylmethyl)-3-cyclopropyl-2,3-dihydroxypropyl]-3-(pyridin-4-yl)propionamide:

In an analogous manner to that described above, by the condensation of N-(tert-butoxycarbonyl)-3-(pyridin-4-yl)-D,L-alanine [J. Gen. Chem. USSR, 40, 2488 (1970)]and (1S,2R,3S)-3-amino-4-cyclohexyl-1-cyclopropyl-1,2-butanediol followed by acidic hydrolysis there were obtained (S or R)-α-amino-N-[(1S,2R,3 S)-1-(cyclohexylmethyl)-3-cyclopropyl-2,3-dihydroxypropyl]-3-(pyridin-4-yl)propionamide, MS: 267 (M+H)+, and (R or S)-α-amino-N-[(1S,2R,3S)-1-(cyclohexylmethyl)-3-cyclopropyl-2,3-dihydroxypropyl]-3-(pyridin-4-yl)propionamide, MS: 267 (M+H)+, each as a colourless foam.

(S)-α-amino-N-[(1S,2R,3S)-1-(cyclohexylmethyl)-3-cyclopropyl-2,3-dihydroxypropyl]-3-(pyrazol-1-yl)propionamide:

1.03 g (2.83 mmol) of HBTU and 0.39 ml (2.83 mmol) of triethylamine were added to a solution of 820 mg (2.83 mmol) of N-[(benzyloxy)carbonyl]-3-(pyrazol-1-yl)-L-alanine [J. Am. Chem. Soc. 107, 7105 (1985)]and 644 mg (2.83 mmol) of (1S,2R,3S)-3-amino-4-cyclohexyl-1-cyclopropyl-1,2-butanediol in 28 ml of acetonitrile and the mixture was stirred at room temperature overnight. The crystals obtained after filtration were dissolved in 30 ml of ethanol and hydrogenated at 400 for two hours. Filtration over diatomaceous earth and evaporation under reduced pressure yielded 670 mg of (S)-α-amino-N-[(1S,2R,3S)-1-(cyclohexylmethyl)-3-cyclopropyl-2,3-dihydroxypropyl]-3-(pyrazol-1-yl)propionamide, MS: 365 (M+H)+, as a colourless foam.

(S)-α-Amino-N-[(1S,2R,3S)-1-(cyclohexylmethyl)-3-cyclopropyl-2,3-dihydroxypropyl]-3-(imidazol-1-yl)propionamide:

In an analogous manner to that described above, by the condensation of N-[(benzyloxy)carbonyl]-3-(imidazol-1-yl)-L-alanine and (1S,2R,3S)-3-amino-4- cyclohexyl-1-cyclopropyl-1,2-butanediol followed by catalytic hydrogenation there was obtained (S)-α-amino-N-[(1S,2R,3S)-1-(cyclohexylmethyl)-3-cyclopropyl-2,3-dihydroxypropyl]-3-(imidazol-1-yl)propionamide, MS: 365 (M+H)+, as a colourless foam.

The N-[(benzyloxy)carbonyl]-3-(imidazol-1-yl)-L-alanine, MS: 290 (M+H)+, which was used was prepared in analogy to the synthesis of N-[(benzyloxy)carbonyl]-3-(pyrazol-1-yl)-L-alanine described in J. Am. Chem. Soc. 107, 7105 (1985), by replacing the pyrazole by imidazole.

(RS)-α-Amino-N-[(1S,2R,3S)-1-(cyclohexylmethyl)-3-cyclopropyl-2,3-dihydroxypropyl]-3-(thiophen-2-yl)propionamide:

In an analogous manner to that described above, by the condensation of rac-α-(tert-butoxyformamido)-3-(thiophen-2-yl)propionic acid [Pol. J. Chem. 54(11–12), 2225 (1980)] and (1S,2R,3S)-3-amino-4-cyclohexyl-1-cyclopropyl-1,2-butanediol followed by acidic hydrolysis there was obtained (RS)-α-amino-N-[(1S,2R,3S)-1-(cyclohexylmethyl)-3-cyclopropyl-2,3-dihydroxypropyl]-3-(thiophen-2-yl)propionamide, MS: 381 (M+H)+ as a colourless foam.

(RS)-α-Amino-N-[(1S,2R,3S)-1-(cyclohexylmethyl)-3-cyclopropyl-2,3-dihydroxypropyl]-3-(furan-2-yl)propionamide:

In an analogous manner to that described above, by the condensation of (RS)-α-(1-benzyloxyformamido)-3-(furan-2-yl)propionic acid [J. Biol. Chem. 171, 383 (1947)]and (1S,2R,3S)-3-amino-4-cyclohexyl-1-cyclopropyl-1,2-butanediol followed by catalytic hydrogenation there was obtained rac-α-amino-N-[(1S,2R,3S)-1-(cyclohexylmethyl)-3-cyclopropyl-2,3-dihydroxypropyl]-3-(furan-2-yl)propionamide, MS: 365 (M+H)+, as a colourless foam.

EXAMPLE 17

The following compounds were manufactured in an analogous manner to that described in Example 1:

From (S)-α-[[[1-methyl-1-[methyl-[2-(2-pyridyl)ethyl]carbamoyl]ethyl]sulfonyl]methyl]hydrocinnamic acid and (S)-amino-N-[(1S,2R,3S)-1-(cyclohexylmethyl)-3-cyclopropyl-2,3 -dihydroxypropyl]imidazole-4-propionamide the (S)-N--[(1S,2R,3S)-1-(cyclohexylmethyl)-3-cyclopropyl-2,3-dihydroxypropyl]-α-[(S)-α-[[[1-methyl-1-[methyl-[2-(2-pyridyl)ethyl]carbamoyl]ethyl]sulfonyl]methyl]hydrocinnamamido]imidazole-4-propionamide as a colourless foam, MS: 779 (M+H)+;

-from (S)-α-[[[1-methyl-1-[methyl-[2-(2-pyridyl)ethyl]carbamoyl]ethyl]sulfonyl]methyl]hydrocinnamic acid and (S)-amino-N-[(1S,2R,3S)-1-(cyclohexylmethyl)-3-cyclopropyl-2,3-dihydroxypropyl]imidazole-4-propionamide the (S)-N-[(S)-1-[[(1S,2R,3S)-1-(cyclohexylmethyl)-3-cyclopropyl-2,3-dihydroxypropyl]carbamoyl]pentyl]-α-[[1-[methyl-[2-2-pyridyl)ethyl]sulfonyl]methyl]hydrocinnamamide as a colourless foam, MS: 755 (M+H)+;

from (S)-α-[[[(morpholinocarbonyl)methyl]sulfonyl]methyl]hydrocinnamic acid and (S)-amino-N-[(1S,2R,3S)-1-(cyclohexylmethyl)-3-cyclopropyl-2,3-dihydroxypropyl]imidazole-4-propionamide the (S)-N-[(1S,2R,3S)-1-(cyclohexylmethyl)-3-cyclopropyl-2,3-dihydroxypropyl]-α-[(S)-α-[[[(morpholinocarbonyl)methyl]sulfonyl]methyl]hydrocinnamamido]imidazole-4-propionamide as a colourless solid, MS: 702 (M+H)+;

from (S)-α-[[[(RS)-1-(morpholinocarbonyl)ethyl]sulfonyl]methyl]hydrocinnamic acid and (S)-amino-N-[(1S,2R,3S)-1-(cyclohexylmethyl)-3-cyclopropyl-2,3-dihydroxypropyl]imidazole-4-propionamide the (S)-N-[(1S,2R,3S)-1-(cyclohexylmethyl)-3-cyclopropyl-2,3-dihydroxypropyl]-α-[(S)-α-[[[(RS)-1-(morpholinocarbonyl)ethyl]sulfonyl]methyl]hydrocinnamamido]imidazole-4-propionamide as a colourless amorphous solid, MS: 716 (M+)+.

from (S)-α-[[[1-methyl-1-[(tetrahydro-4H-1,4-thiazin-4-yl)carbonyl]ethyl]sulfonyl]methyl]hydrocinnamic acid and (S)-amino-N-[(1S,2R,3S)-1-(cyclohexylmethyl)-3-cyclopropyl-2,3-dihydroxypropyl]imidazole-4-propionamide the (S)-N-[(1S,2R,3S)-1-(cyclohexylmethyl)-3-cyclopropyl-2,3-dihydroxypropyl]-α-[(S)-α-[[[ 1-methyl-1-[(tetrahydro-4 H-1,4-thiazin-4-yl)carbonyl]ethyl]sulfonyl]methyl]hydrocinnamamido]imidazole-4-propionamide as a colourless solid, MS: 746 (M+H)+;

from (S)-α-[[[1-methyl-1-[(tetrahydro-4'H-1,4'-thiazin-4'-yl)carbonyl]ethyl]sulfonyl]methyl]hydrocinnamic acid 1',1'-dioxide and (S)-amino-N-[(1S,2R,3S)-1-(cyclohexylmethyl)-3-cyclopropyl-2,3-dihydroxypropyl]imidazole-4-propionamide the (S)-N-[(1S,2R,3S)-1-(cyclohexylmethyl)-3-cyclopropyl-2,3-dihydroxypropyl]-α-[(S)-α-[[[1-methyl-1-[(tetrahydro-4'H-1,4-thiazin-4'-yl)carbonyl]ethyl]sulfonyl]methyl]hydrocinnamamido]imidazole-4-propionamide-1',1'-dioxide as a colourless solid, MS: 778 (M+H)+;

from (S)-α-[[[1-methyl-1-[(4-methyl-1-piperazinyl)carbonyl]ethyl]sulfonyl]methyl]hydrocinnamic acid and (S)-amino-N-[(1S,2R,3S)-1-(cyclohexylmethyl)-3-cyclopropyl-2,3-dihydroxypropyl]imidazole-4-propionamide the (S)-N-[(1S,2R,3S)-1-(cyclohexylmethyl)-3-cyclopropyl-2,3-dihydroxypropyl]-α-[(S)-α-[[[1-methyl-1-[(4-methyl-1-piperazinyl)carbonyl]ethyl]sulfonyl]methyl]hydrocinnamamido]imidazole-4-propionamide as a colourless solid, MS: 743 (M+H)+;

from (S/R=9/1)-α-[[[1-[[2-(2-hydroxyethoxy)ethyl]carbamoyl]-1-methylethyl]sulfonyl]methyl]hydrocinnamic acid and (S)-amino-N-[(1S,2R,3S)-1-(cyclohexylmethyl)-3-cyclopropyl-2,3-dihydroxypropyl]imidazole-4-propionamide the (S)-N-[(1S,2R,3S)-1-(cyclohexylmethyl)-3-cyclopropyl-2,3-dihydroxypropyl]-α-[(S/R=9/1 )-α-[[1-[2-(2-hydroxyethoxy)carbamoyl]-1-methylethyl]sulfonyl]methyl]hydrocinnamamido]imidazole-4-propionamide as a colourless oil, MS: 748.3 (M+H)+.

The acids used as the starting materials were prepared as follows:

(S)-α-[[[1-Methyl-1-[methyl-[2-(2-pyridyl)ethyl]carbamoyl]ethyl]sulfonyl]methyl]hydrocinnamic acid:

In an analogous manner to that described in Example 1, by the condensation of rac-2-[[2-(ethoxycarbonyl)-3-phenylpropyl]sulfonyl]-2-methylpropionic acid and 2-(2-methylaminoethyl)pyridine there was obtained ethyl (S)-α-[[[1-methyl-1-[methyl[2-(2-pyridyl)ethyl]carbamoyl]ethyl]sulfonyl]methyl]hydrocinnamate. Subsequent enzymatic saponification, analogously to Example 6, paragraph (c), yielded (S)-α-[[[1-methyl-1-[methyl-[2(2-pyridyl)ethyl]carbamoyl]ethyl]sulfonyl]methyl]hydrocinnamic acid as a colourless solid, MS: 470 (M+H)+.

(S)-α-[[[(Morpholinocarbonyl)methyl]sulfonyl]methyl]hydrocinnamic acid:

In an analogous manner to that described in Example 1, paragraphs (d) and (e), and Example 2, paragraph (a), starting from 2-mercaptoacetic acid and ethyl 2-benzylacrylate there was obtained ethyl (RS)-α-[[[(morpholinocarbonyl)methyl]sulfonyl]methyl]hydrocinnamate as a colourless oil, MS: 383 (M)+, enzymatic saponification of which analogously to Example 6, paragraph (c), yielded (S)-α-[[[(morpholinocarbonyl)methyl]sulfonyl]methyl]hydrocinnamic acid, MS: 355 (M)+, as a colourless foam.

(S)-α-[[[(RS)-1-(Morpholinocarbonyl)ethyl]sulfonyl]methyl]hydrocinnamic acid:

In an analogous manner to that described in Example 1, paragraphs (d) and (e), and Example 2, paragraph (a), starting from thiolactic acid and ethyl 2-benzylacrylate there was obtained ethyl (RS)-α-[[[(RS)-1-(morpholinocarbonyl)ethyl]sulfonyl]methyl]hydrocinnamate, MS: 397 (M)+, as a colourless oil, enzymatic saponification of which analogously to Example 6, paragraph (c), yielded (S)-α-[[[(RS)-1-(morpholinocarbonyl)ethyl]sulfonyl]methyl]hydrocinnamic acid, MS: 369 (M)+, as a colourless foam.

(S)-α-[[[1-Methyl-1-[(tetrahydro-4H-1,4-thiazin-4-yl)carbonyl]ethyl]sulfonyl]methyl]hydrocinnamic acid:

In an analogous manner to that described in Example 1, paragraphs (d) and (e), starting from 2-mercaptoisobutyric acid and ethyl 2-benzylacrylate there was obtained (RS)-2-[[2-[(ethoxy)carbonyl]-3-phenylpropyl]sulfonyl]-2-methylpropionyl chloride, reaction of which with thiomorpholine analogously to Example 2, paragraph (a), and subsequent enzymatic hydrolysis analogously to Example 6, paragraph (c), yielded (S)-α-[[[1-methyl-1-[(tetrahydro-4H-1,4-thiazin-4-yl)carbonyl]ethyl]sulfonyl]methyl]hydrocinnamic acid, MS: 399 (M)+, as a colourless solid.

(S)-α-[[[1-Methyl-1-[(tetrahydro-4'H-1,4-thiazin-4'-yl)carbonyl]ethyl]sulfonyl]methyl]hydrocinnamic acid 1',1'-dioxide:

In an analogous manner to that described in Example 1, paragraph (d), by the oxidation of (S)-α-[[[1-methyl-1-[(tetrahydro-4H-1,4-thiazin-4- yl)carbonyl]ethyl]sulfonyl]methyl]hydrocinnamic acid with potassium monopersulphate triple salt there was obtained (S)-α-[[[1-methyl-1-[(tetrahydro-4'H-1,4-thiazin-4'-yl)carbonyl]ethyl]sulfonyl]methyl]hydrocinnamic acid 1',1'-dioxide, MS: 431 (M)+, as a colourless solid.

(S)-α-[[[1-Methyl-1-[(4-methyl-1-piperazinyl)carbonyl]ethyl]sulfonyl[methyl]hydrocinnamic acid:

In an analogous manner to that described in Example 1, paragraphs (d) and (e), starting from 2-mercaptoisobutyric acid and ethyl 2-benzylacrylate there was obtained (RS)-2-[[2-[(ethoxy)carbonyl]-3-phenylpropyl]sulfonyl]-2-methylpropionyl chloride, reaction of which with 1-methylpiperazine analogously to Example 2, paragraph (a), and subsequent enzymatic hydrolysis analogously to Example 6, paragraph (c), yielded (S)-α-[[[1-methyl-1-[(4-methyl-1-piperazinyl)carbonyl]ethyl]sulfonyl]methyl]hydrocinnamic acid, MS: 396 (M)+, as a colourless solid.

(S/R=9/1)-α-[[[1-[[2-(2-Hydroxyethoxy)ethyl]carbamoyl]-1-methylethyl]sulfonyl]methyl]hydrocinnamic acid:

In an analogous manner to that described in Example 6, paragraphs (a) to (c), starting from 2-mercaptoisobutyric acid and ethyl 2-benzylacrylate there was obtained (RS)-2-[[2-[(ethoxy)carbonyl]-3-phenylpropyl]sulfonyl]-2-methylpropionic acid, reaction of which 2-(2-aminoethoxy)ethanol and subsequent enzymatic hydrolysis of the resulting ethyl ester yielded (S/R=9/1 )-α-[[[1-[[2-(2-hydroxyethoxy)ethyl]carbamoyl]-1-methylethyl]sulfonyl]methyl]hydrocinnamic acid, MS: 401.9 (M+H)+, as a colourless oil.

EXAMPLE 18

0.14ml (1 mmol) of triethylamine and 191 mg (0.5 mmol) of HBTU were added to a solution of 365 mg (0.5 mmol) of N-[(S)-α-[[[1-methyl-1-[methyl-2-(2-pyridyl)ethyl]carbamoyl]ethyl]sulfonyl]methyl]hydrocinnamoyl]-3-(thiazol-4-yl)-D,L-alanine and 115 mg (0.5 mmol) of (1S,2R,3S)-3-amino-4-cyclohexyl-1-cyclopropyl-1,2-butanediol in 5 ml of acetonitrile and the mixture was stirred at room temperature overnight. The reaction solution was evaporated under reduced pressure and the residue obtained was partitioned between ethyl acetate and saturated sodium hydrogen carbonate solution. The aqueous phase was extracted three times with ethyl acetate. The organic phases were washed with water and saturated sodium chloride solution, dried over magnesium sulphate, filtered and evaporated under reduced pressure. Chromatography of the residue on silica gel using a 95:5 mixture of methylene chloride and methanol yielded 152 mg of the less polar (S or R)-N-[(1S,2R,3S)-1-(cyclohexylmethyl)-3-cyclopropyl-2,3-dihydroxypropyl]-α-[(S)-α-[[[1-methyl-1-[methyl-[2-(2pyridyl)ethyl]carbamoyl]ethyl]sulfonyl]methyl]hydrocinnamamido]-3-(thiazol-4-yl)propionamide, MS: 797 (M+H)+, and 114 mg of the more polar (R or S)-N-[(1S,2R,3S)-1-(cyclohexylmethyl)-3-cyclopropyl-2,3-dihydroxypropyl]-α-[(S)-α-[[[1-methyl-1-[methyl-[2-(2-pyridyl)ethyl]carbamoyl]ethyl]sulfonyl]methyl]hydrocinnamamido]-3-(thiazol-4-yl)propionamide, MS: 797 (M+H)+, each as a colourless foam.

The N-[(S)-α-[[[1-methyl-1-[methyl-[2-(2-pyridyl)ethyl]carbamoyl]ethyl]sulfonyl]methyl]hydrocinnamoyl]-3-(thiazol-4-yl)-D,L-alanine used as the starting material was prepared as follows:

(a) N-[(S)-α-[[[1-Methyl-1-[methyl-[2-(2-pyridyl)ethyl]carbamoyl]ethyl]sulfonyl]methyl]hydrocinnamoyl]-3-(thiazol-4-yl)D,L-alanine methyl ester:

0.28 ml (2.1 mmol) of triethylamine and 265 mg (0.7 mmol) of HBTU were added to a solution of 328 mg (0.7 mmol) of (S)-α-[[[1-methyl-1-[methyl-[2-(2-pyridyl)ethyl]carbamoyl]ethyl]sulfonyl]methyl]hydrocinnamic acid and 181 mg (0.7 mmol) 3-(thiazol-4-yl)-D,L-alanine methyl ester dihydrochloride in 7 ml of acetonitrile and the mixture was stirred at room temperature overnight. Evaporation of the solution under reduced pressure and chromatography of the residue on silica gel using a 200:10:1 mixture of methylene chloride, methanol and ammonia as the eluent yielded 309 mg of N-[(S)-α-[[[1-methyl-1-[methyl-[2-(2-pyridyl)ethyl]carbamoyl]ethyl]sulfonyl]methyl]hydrocinnamoyl]-3-(thiazol-4-yl)-D,L-alanine methyl ester as a colourless foam, MS: 601 (M+H)+.

(b) N-[(S)-α-[[[1-Methyl-1-[methyl-[2-(2-pyridyl)ethyl]carbamoyl]ethyl]sulfonyl]methyl]hydrocinnamoyl]-3-(thiazol-4-yl)-D,L-alanine:

A solution of 300 mg of N-[(S)-α-[[[1-methyl-1-[methyl-[2-(2-pyridyl)ethyl]carbamoyl]ethyl]sulfonyl]methyl]hydrocinnamoyl]-3-(thiazol-4-yl)-D,L-alanine methyl ester in 2.5 ml of dioxan was treated with a solution of 24.3 mg of lithium hydroxide hydrate in 1 ml of water and stirred at 50 for 3 hours. Subsequently, the solution was partitioned between ethyl acetate and water and the organic phase was extracted three times with water. The aqueous extracts were adjusted to pH 2 with ethyl acetate and with 2N hydrochloric acid and evaporated under reduced pressure. There were obtained 365 mg of N-[(S)-α-[[[1-methyl-1-[methyl-[2-(2-pyridyl)ethyl]carbamoyl]ethyl]sulfonyl]methyl]hydrocinnamoyl]-3-(thiazol-4-yl)-D,L-alanine as a colourless foam which was used directly in the next step.

EXAMPLE 19

In an analogous manner to that described in Example 18, paragraphs (a) and (b), from -α-[[[1-methyl-1-(morpholinocarbonyl)ethyl]sulfonyl]methyl]hydrocinnamic acid and 3-(thiazol-4-yl)-D,L-alanine methyl ester dihydrochloride there was obtained N-[(S)-α-[[[1-methyl-1-(morpholinocarbonyl)ethyl]sulfonyl]methyl]hydrocinnamoyl]-3-(thiazol-4- yl)- D,L-alanine methyl ester, which was saponified with lithium hydroxide to the corresponding acid. Coupling with (1S,2R,3S)-3-amino-4-cyclohexyl-1-cyclopropyl-1,2-butanediol and subsequent chromatography yielded (R or S)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(thiazol-4-yl)propionamide, MS 747 (M+H)+, and (S or R)-N-[(1S,2R,3S)-1-(cyclohexylmethyl)-3-cyclopropyl-2,3-dihydroxypropyl]-α-[(S)-α-[[[1-methyl-1-(morpholinocarbonyl)ethyl]sulfonyl]methyl]hydrocinnamamido]-3-(thiazol-4-yl)propionamide, MS 747 (M+H)+, each as a colourless foam.

EXAMPLE 20

The following compound was manufactured in an analogous manner to that described in Example 1:

From (S)-α-amino-N-[(1S,2R,3S)-1-benzyl-3-cyclopropyl-2,3-dihydroxypropyl]-4-imidazolepropionamide and -α-[[[1-methyl-1-(morpholinocarbonyl)ethyl]sulfonyl]methyl]hydrocinnamic acid the (S)-N-[(1S,2R,3S)-1-benzyl-3-cyclopropyl-2,3-dihydroxypropyl]-α-[(S)-α-[[[1-methyl-1-(morpholinocarbonyl)ethyl]sulfonyl]methyl]hydrocinnamamido]imidazol-4-propionamide, MS 724 (M+H)+, as a colourless foam.

The (S)-α-amino-N-[(1S,2R,3S)-1-benzyl-3-cyclopropyl-2,3-dihydroxypropyl]imidazole-4-propionamide used as the starting material was prepared as follows:

(a) tert-Butyl [(1S,2R)-1-benzyl-2-(cyclopropylcarbonyl)-2-hydroxyethyl]carbamate:

9.96 ml (124.5 mmol) of cyclopropyl bromide in 100 ml of ether were added dropwise within 30minutes to 3.03 g (124.5 mmol) of magnesium in 10 ml of abs. ether under slight reflux and the mixture was subsequently heated to reflux for 2 1/2 hours. Subsequently, 6.25 g (22.63 mmol) of tert-butyl [(1S,2R)-1-benzyl-2-cyano-2-hydroxyethyl]carbamate (EPA 0,266,950) were added dropwise thereto under reflux within 5 minutes and the mixture was heated to reflux for a further 2 ½ hours. Finally, the mixture was left to cool (10°), 10% citric acid was added dropwise thereto and the mixture was extracted twice with ether. The organic phase was washed with water and saturated sodium chloride solution, dried over magnesium sulphate, filtered and evaporated under reduced pressure. Chromatography on silica gel using a 9:1 mixture of toluene and ethyl acetate yielded tert-butyl [(1S,2R)-1-benzyl-2-(cyclopropylcarbonyl)-2-hydroxyethyl]carbamate as a pale yellow solid, MS: 246 (M−C3H9O)+.

(b) tert-Butyl [(1S,2R,3S)-1-benzyl-3-cyclopropyl-2,3-dihydroxypropyl]carbamate:

2.83 g (8.77 mmol) tert-butyl [(1S,2R)-1-benzyl-2-(cyclopropylcarbonyl)-2-hydroxyethyl]carbamate were dissolved in 130 ml of methylene chloride, 3 ml of acetic acid were added thereto and the mixture was finally treated portionwise at 0°–10° C. with 0.332 g (8.78 mmol) of sodium borohydride. The reaction solution was stirred at 50 for a further 2 hours and was then partitioned between 2N sodium hydrogen carbonate solution and methylene chloride. The organic phase was separated, washed with water and with saturated sodium chloride solution, dried over magnesium sulphate, filtered and evaporated under reduced pressure. Crystallization of the residue from ether/hexane yielded 2.1 g of tert-butyl [(1S,2R,3S)-1-benzyl-3-cyclopropyl-2,3-dihydroxypropyl]carbamate as colourless needles, m.p. 83–85°.

(c) (1S,2R,3S)-3-Amino-1-cyclopropyl-4-phenyl-1,2-butanediol:

A solution of 2.0 g (6.23 mmol) of tert-butyl [(1S,2R,3S)-1-benzyl-3-cyclopropyl-2,3-dihydroxypropyl]carbamate in 20 ml of methanol was treated with 20 ml of 2N hydrochloric acid and the solution was heated to 500 for 90 minutes. After cooling, the solution was neutralized by the addition of 40 ml of 1N sodium hydroxide solution and evaporated to dryness on a rotary evaporator under reduced pressure. The residue was partitioned between water and methylene chloride. The organic phase was washed with water and saturated sodium chloride solution, dried over magnesium sulphate, filtered and evaporated under reduced pressure. There was obtained 0.7 g of (1S,2R,3S)-3-amino-1-cyclopropyl-4-phenyl-1,2-butanediol as white crystalline solid, MS: 150 (M−C4H8O)+.

(d) (S)-α-Amino-N-[(1S,2R,3S)-1-benzyl-3-cyclopropyl-2,3-dihydroxypropyl]imidazole-4-propionamide:

In an analogous manner to that described in Example 1, paragraph (c), by the condensation of Fmoc-His(Fmoc)-OH and (1S,2R,3S)-3-amino-1-cyclopropyl-4-phenyl-1,2-butanediol followed by cleavage of the protecting groups using piperidine in methylene chloride there was obtained (S)-α-amino-N-[(1S,2R,3S)-1-benzyl-3-cyclopropyl-2,3-dihydroxypropyl]-imidazole-4-propionamide as a colourless foam, MS: 359 (M+H)+.

EXAMPLE 21

In an analogous manner to that described in Example 1, by the condensation of (RS)-α-[[[1-[(cis-2,6-dimethylmorpholino)carbonyl]-1-methylethyl]sulfonyl]methyl]hydrocinnamic acid and (S)-α-amino-N-[(1S,2R,3S)-1-(cyclohexylmethyl)-3-cyclopropyl- 2,3-dihydroxypropyl]imidazole-4-propionamide there was obtained the less polar (S)-N-[(1S,2R,3S)-1-(cyclohexylmethyl)-3-cyclopropyl-2,3-dihydroxypropyl]-α-[(R or S)-α-[[[1-[(cis-2,6-dimethylmorpholino)carbonyl]-1-methylethyl]sulfonyl]methyl]hydrocinnamamido]imidazole-4-propionamide, MS: 758 (M+H)+, and the more polar (S)-N-[(1S,2R,3S)-1-(cyclohexylmethyl)-3-cyclopropyl-2,3-dihydroxypropyl]-α-[(S or R)-α-[[[1-[(cis-2,6-dimethylmorpholino)carbonyl]-1-methylethyl]sulfonyl]methyl]hydrocinnamamido]imidazole-4-propionamide, MS: 758 (M+H)+, each as a colourless foam.

The (RS)-α-[[[1-[(cis-2,6-dimethylmorpholino)carbonyl]-1-methylethyl]sulfonyl]methyl]hydrocinnamic acid used as the starting material was prepared as follows:

In an analogous manner to that described in Example 2, paragraphs (c) and (d), by the reaction of (RS)-2-[[2-[(benzyloxy)carbonyl]-3-phenylpropyl]sulfonyl]-2-methylpropionyl chloride with 2,6-dimethylmorpholine in pyridine followed by chromatographic separation of the resulting diastereomers there was obtained benzyl (RS)-α-[[[1-[(cis-2,6-dimethylmorpholino)carbonyl]-1-methylethyl]sulfonyl]methyl]hydrocinnamate, MS: 501 (M)+, as a colourless oil.

Subsequent catalytic hydrogenation yielded (RS)-α-[[[1-[(cis-2,6-dimethylmorpholino)carbonyl]-1-methylethyl]sulfonyl]methyl]hydrocinnamic acid, MS: 411 (M)+, as a colourless foam.

EXAMPLE 22

The following compounds were obtained by cleavage of Boc protecting group in an analogous manner to that described in Example 4, without a basic working-up:

From tert-butyl 4-[2-[[(S or R)-2-[[(S)-1-[[(1S,2R,3S)-1-(cyclohexylmethyl)-3-cyclopropyl-2,3-dihydroxypropyl]carbamoyl] -2-imidazol-4- ylethyl]carbamoyl]-3-phenylpropyl]sulfonyl]-2-methylpropionyl]-1-piperazinecarboxylate (see Example 2) the (S)-N-[(1S,2R,3S)-1-(cyclohexylmethyl)-3-cyclopropyl-2,3-dihydroxypropyl]-α-[(S or R)-α-[[[1-methyl-1-(1-piperazinylcarbonyl)ethyl]sulfonyl]methyl]hydrocinnamamido]imidazole-4-propionamide dihydrochloride as a colourless solid; MS: 729 (M+H)+. (base);

from tert-butyl 4-[2-[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionyl]-1-piperazine carboxylate (see Example 2) the (S)-N-[(1S,2R,3S)-1-(cyclohexylmethyl)-3-cyclopropyl-2,3-dihydroxypropyl]-α-[(R or S)-α-[[[1-methyl-1-(1 piperazinylcarbonyl)ethyl]sulfonyl]methyl]hydrocinnamamido]imidazole-4-propionamide dihydrochloride as a colourless solid; MS: 729 (M+H)+(base).

EXAMPLE A

| Oral aqueous suspension | |
|---|---|
| Composition: | |
| 2-[2-[[(S)-2-[[(S)-1-[[(1S,2R,3S)-1-(Cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose micronized | 5.0 g |
| Polysorbate 80 | 0.3 g |
| Hydroxypropylmethylcellulose | 1.0 g |
| Flavouring | q.s |
| Methylparaben | 0.2 g |
| Propyleneparaben | 0.04 g |
| Water ad | 100.0 ml |

EXAMPLE B

| Example B Oral aqueous solution | |
|---|---|
| Composition: | |
| 2-[2-[[(S)-2-[[(S)-1-[[(1S,2R,3S)-1-(Cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose | 1.0 g |
| methanesulphonate | |
| Methylparaben | 0.2 g |
| Propylparaben | 0.04 g |
| Flavouring | q.s. |
| Water ad | 100.0 ml |

EXAMPLE C

| Tablets | |
|---|---|
| Composition: | |
| 1) 2-[2-[[(S)-2-[[(S)-1-[[(1S,2R,3S)-1-(Cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose methanesulphonate | 200 mg |
| 2) Anhydrous lactose | 160 mg |
| 3) Hydroxypropylmethylcellulose | 18 mg |
| 4) Sodium carboxymethylcellulose | 20 mg |
| 5) Magnesium stearate | 2 mg |
| Tablet weight | 400 mg |

Manufacturing procedure:

1) and 2) are mixed intensively. The mixture is thereafter moistened with an aqueous solution of 3) and kneaded, and the resulting mass is granulated, dried and seived. The granulate is mixed with 4) and 5) and pressed to tablets of suitable size.

EXAMPLE D

| Capsules | |
|---|---|
| Composition: | |
| 1) 2-[2-[[(S)-2-[[(S)-1-[[(1S,2R,3S)-1-(Cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose methanesulphonate | 200 mg |
| 2) Anhydrous lactose | 160 mg |
| 3) Hydroxypropylmethylcellulose | 18 mg |
| 4) Sodium carboxymethylcellulose | 20 mg |
| 5) magnesium stearate | 2 mg |
| Capsule fill weight | 400 mg |

Manufacturing procedure:

1) and 2) are mixed intensively. The mixture is thereafter moistened with an aqueous solution of 3) and kneaded, and the resulting mass is granulated, dried and sieved. The granulate is mixed with 4) and 5), the mixture is filled into capsules of suitable size.

EXAMPLE E

| Injection solution | |
|---|---|
| Composition: | 1 ml |
| 2-[2-[[(S)-2-[[(S)-1-[[(1S,2R,3S)-1-(Cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose methanesulphonate | 20 mg |
| Pyrogen-free D-mannitol | 10 mg |
| Water for injection ad | 1.0 ml |

Manufacturing procedure:

The active substance and the mannitol are dissolved in nitrogen-gassed water and subsequently lyophilized according to a conventional procedure.

EXAMPLE F

When the procedures described in Examples A–E are followed, corresponding galenical preparations can be manufactured from the following, likewise preferred compounds and their pharmaceutically usable salts:

2-[[(S or R)-2-[[(S)-1-[[(1S,2R,3S)-1-(Cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl methoxyacetate, tert-Butyl [(S)-2-[[(S or R)-2-[[(S)-1-[[(1S,2R,3S)-1-(cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate, (S)-N-[(1S,2R,3S)-1-(Cyclohexylmethyl)-3-cyclopropyl-2,3-dihydroxypropyl]-α-[(S)-α-[[[1-(morpholinocarbonyl)-1 -methyl]sulfonyl]methyl]hydrocinnamamido]imidazole-4-propionamide, (S)-N-[(1S,2R,3S)-1-(Cyclohexylmethyl)-3-cyclopropyl-2,3-dihydroxypropyl]-α-[(S)-α-[[[1-[(4-hydroxypiperidino)carbonyl]-1-methylethyl]sulfonyl]methyl]hydrocinnamamido]imidazole-4-propionamide, (S or R)-N-[(1S,2R,3S)-1-(Cyclohexylmethyl)-3-cyclopropyl-2,3-dihydroxypropyl]-α-[(S)-α-[[[1-methyl-1-[morpholinocarbonyl]ethyl]sulfonyl]methyl]hydrocinnamamido]-3-(thiazolyl-4-yl)propionamide, (S or R)-N-[(1S,2R,3S)-1-(Cyclohexylmethyl)-3-cyclopropyl--2,3-dihydroxypropyl]-α-[(S)-α-[[[1-methyl-1-(morpholinocarbonyl)ethyl]sulfonyl]methyl]hydrocinnamamido]-3-(pyridin-3-yl)propionamide.

We claim:

1. Compounds of the formula:

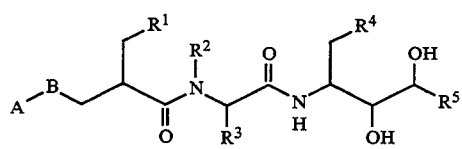

I wherein R¹ is cycloalkyl, phenyl, substituted phenyl, naphthyl, thienyl, pyridyl, ,quinolyl, isoquinolyl or benzyl, R² is hydrogen or methyl, R³ is hydrogen, hydroxy, alkyl, alkoxy, alkenyloxy, alkylthio, alkylthioalkyl or alkoxycarbonyl, or imidazol-1-ylmethyl, imidazol-2-ylmethyl or imidazol-4-ylmethyl, each of which can be methylated on a carbon atom and/or nitrogen atom, 2-aminoimidazol-4-ylmethyl, 5-iodoimidazol-4-ylmethyl, pyrazol-1-ylmethyl, pyrazol-3-ylmethyl, thiazol-2-ylmethyl, thiazol-4-ylmethyl, thiazol-5-ylmethyl, 2-aminothiazol-4-ylmethyl, thienylmethyl, furanylmethyl, pyridylmethyl, aminocarbonyl, aminocarbonylalkyl or alkoxycarbonylalkyl, R⁴ is cycloalkyl, substituted cycloalkyl, phenyl or halophenyl, R⁵ is cycloalkyl, cycloalkylalkyl or alkyl, B is a sulphur atom or a sulfinyl or sulfonyl group and A is the group

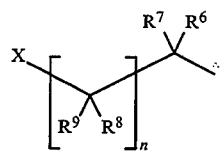

(a)

in which R⁶, R⁷ and R⁸ each independently are hydrogen or alkyl, R⁹ is hydrogen, alkyl, hydroxyalkyl, amino, alkoxycarbonylamino or benzyloxycarbonylamino, n is the integer zero or one and X is the group Y—CO— or, where n is the integer one, also the group Z—O—, wherein Y is cycloalkylamino, sulphoalkylamino or bisalkoxyalkylamino, or pyridylalkylamino or morpholinoalkylamino, each of which can be substituted at the amino group by alkyl; pyrazinylalkylamino, which can be substituted at the nitrogen atom and/or at the amino group by alkyl; 4-piperidinylalkylamino, which can be substituted at the nitrogen atom by alkyl, benzyl, benzyloxycarbonyl, alkoxycarbonyl or hydroxyalkyl and/or at the amino group by alkyl; alkoxycarbonylalkylamino, hydroxyalkoxyalkylamino, hydroxyalkylamino, bishydroxyalkylamino, the group (Rᵃ)(Rᵇ)N- in which Rᵃ and Rᵇ each independently are hydrogen or alkyl or together with the nitrogen atom to which they are attached are a saturated 5- or 6-membered heterocyclic ring which can contain an additional nitrogen atom or an oxygen or sulphur atom as a further hetero atom or can carry an oxo group, whereby the sulphur atom can also be present in the form of a sulfinyl or sulfonyl group, or which can be o substituted on one or two carbon atoms by alkyl, hydroxy, hydroxyalkyl or alkoxyalkoxy or on a second nitrogen atom which may be present by alkyl, benzyl, benzyloxycarbonyl, alkoxycarbonyl or hydroxyalkyl, or in which the optionally present second nitrogen atom can carry an oxygen atom, alkoxyalkoxyalkoxy, cycloalkylalkoxy, 1,3-dimethyldioxolan-2-ylalkoxy, the group (Rᵃ)(Rᵇ)N-alkoxy, the residue of a natural aminodesoxy sugar or, where R⁹ is different from hydrogen or alkyl, also alkoxy and Z is C₅-C₁₇-alkylcarbonyl, benzoyl, alkoxyalkylcarbonyl, cycloalkylcarbonyl, aminoalkylcarbonyl which can be substituted at the nitrogen atom by alkoxycarbonyl or benzyloxycarbonyl, alkylaminocarbonyl, phenylaminocarbonyl or, where R⁹ is different from hydrogen or alkyl, also hydrogen, in the form of optically pure diastereomers, mixtures of diastereomers, diastereomeric racemates or mixtures of diastereomeric racemates as well as pharmaceutically usable salts of these compounds.

2. Compounds in accordance with claim 1 wherein Z is alkoxyalkylcarbonyl, cycloalkylcarbonyl, aminoalkylcarbonyl which can be substituted at the nitrogen atom by alkoxycarbonyl or benzyloxycarbonyl, or alkylaminocarbonyl.

3. Compounds in accordance with claim 2 wherein Z is C₁-C₄-alkoxy-C₁-C₄-alkylcarbonyl, cyclo-propylcarbonyl, tert-butoxycarbonylamino-C₁-C₄-alkylcarbonyl, benzyloxycarbonylamino-C₁-C₄-alkylcarbonyl or CC₁-C₄-alkylaminocarbonyl.

4. A compound in accordance with claim 3 wherein said compound is N-(tert-butoxycarbonyl)glycine 2-

[[(R or S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl ester.

5. A compound in accordance with claim 3 wherein said compound is 2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropyl methoxyacetate.

6. Compounds in accordance with claim 1, wherein $R^1$ is cycloalkyl, phenyl, substituted phenyl, naphthyl, thienyl, pyridyl, quinolyl, isoquinolyl or benzyl, $R^2$ is hydrogen or methyl, $R^3$ is hydrogen, hydroxy, alkyl, alkoxy, alkenyloxy, alkylthio, alkylthioalkyl or alkoxycarbonyl, or imidazol-2-ylmethyl or imidazol-4-ylmethyl, each of which can be methylated on a carbon atom and/or nitrogen atom, 2-aminoimidazol-4-ylmethyl, 5-iodoimidazol-4-ylmethyl, thiazol-4-ylmethyl, thienylmethyl, furanylmethyl, pyridylmethyl, aminocarbonyl, aminocarbonylalkyl or alkoxycarbonylalkyl, $R^4$ is cycloalkyl, substituted cycloalkyl, phenyl or halophenyl, $R^5$ is cycloalkyl, cycloalkylalkyl or alkyl, B is a sulphur atom or a sulfinyl or sulfonyl group, $R^6$, $R^7$ and $R^8$ each independently are hydrogen or alkyl, $R^9$ is hydrogen, alkyl, hydroxyalkyl, amino, alkoxycarbonylamino or benzyloxycarbonylamino, n is the integer zero or one and X is the group Y—CO— or, where n is the integer one, also the group Z—O—, wherein Y is cycloalkylamino, sulphoalkylamino, bisalkoxyalkylamino or pyridylalkylamino, or 4-piperidinylalkylamino which can be substituted at the nitrogen atom by alkyl, benzyl, benzyloxycarbonyl, alkoxycarbonyl or hydroxyalkyl; alkoxycarbonylalkylamino, hydroxyalkylamino, bishydroxyalkylamino, the group $(R^a)(R^b)N$- in which $R^a$ and $R^b$ each independently are hydrogen or alkyl or together with the nitrogen atom to which they are attached are a saturated 5- or 6membered heterocyclic ring which can contain an additional nitrogen atom or an oxygen or sulphur atom as a further hetero atom, whereby the sulphur atom can also be present in the form of a sulfinyl or sulfonyl group, which can be substituted on one or two carbon atoms by alkyl, hydroxy, hydroxyalkyl or alkoxyalkoxy, on a second nitrogen atom which may be present by alkyl, benzyl, benzyloxycarbonyl, alkoxycarbonyl or hydroxyalkyl or which can carry an oxo group, alkoxyalkoxyalkoxy, cycloalkylalkoxy, 1,3-dimethyldioxolan-2-ylalkoxy, the group $(R^a)(R^b)N$-alkoxy, the residue of a natural aminodesoxy sugar or, where $R^9$ is different from hydrogen or alkyl, also alkoxy and Z is $C_5$-$C_{17}$-alkylcarbonyl, benzoyl, alkoxyalkylcarbonyl, cycloalkylcarbonyl, aminoalkylcarbonyl, which can be substituted at the nitrogen atom by alkoxycarbonyl or benzyloxycarbonyl, alkylaminocarbonyl, phenylaminocarbonyl or, where $R^9$ is different from hydrogen or alkyl, also hydrogen.

7. A compound in accordance with claim 6 wherein said compound is cyclopropylmethyl 2-[[(R)-2-[[-(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionate.

8. A compound in accordance with claim 6 wherein said compound is tert-butyl [(R)-2-[[(S or R)-2-[[(S)--1-[[(1S,2R,3S)-1-(cyclohexyl-methyl)-3-cyclopropyl-2,3-dihydroxypropyl]carbamoyl]-2-imidazol-4-ylethyl]carbamoyl]-3-phenylpropyl]sulfonyl]-2-(morpholinocarbonyl)ethyl]carbamate.

9. A compound in accordance with claim 6 wherein said compound is 2-[2-[[(S)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-2-methylpropionamido]-2-deoxy-D-glucopyranose.

10. A compound in accordance with claim 6 wherein said compound is (S)-α-[(S or R)-α-[[[(R)-2-amino-2-(morpholinocarbonyl)ethyl]sulfonyl]methyl]hydrocinnamamido]-N-[(1S,2R,3S)-1-(cyclo-hexylmethyl)-3-cyclopropyl-2,3-dihydroxypropyl]imidazole-4-propionamide.

11. A compound in accordance with claim 6 wherein said compound is tert-butyl [(S)-2-[[(S or R)-2-[[(S)-1-[[(1S,2R,3S)-1-(cyclohexylmethyl)-3-cyclopropyl-2,3-dihydroxypropyl]carbamoyl]-2-imidazol-4-ylethyl]carbamoyl]-3-phenylpropyl]sulfonyl]-1-(methoxycarbonyl)-2-methylpropyl]carbamate.

12. Compounds in accordance with claim 1, wherein $R^1$ is cycloalkyl, phenyl, substituted phenyl, naphthyl, thienyl or pyridyl, $R^2$ is hydrogen, $R^3$ is hydrogen, hydroxy, alkyl, alkoxy, allyloxy, alkythio, alkylthiomethyl, alkoxycarbonyl, imidazol-1-ylmethyl, imidazol-4-ylmethyl, 2-aminoimidazol-4-ylmethyl, 5-iodoimidazol-4-ylmethyl, pyrazol-1-ylmethyl, thiazol-4-ylmethyl, thien-2-ylmethyl, furan-2-ylmethyl, pyridylmethyl or aminocarbonyl, $R^4$ is cycloalkyl or phenyl, $R^5$ is cycloalkyl or alkyl, B is sulfonyl, $R^6$ and $R^7$ each are hydrogen or $C_1$-$C_4$-alkyl, Y is cycloalkylamino, sulphoalkylamino or bisalkoxyalkylamino, or pyridylalkylamino, each of which can be substituted at the amino group by alkyl; 4-piperidinylalkylamino, which can be substituted at the nitrogen atom by alkyl, benzyl, benzyloxycarbonyl, alkoxycarbonyl or hydroxyalkyl; alkoxycarbonylalkylamino, hydroxyalkoxyalkylamino, hydroxyalkylamino, bishydroxyalkylamino or the group $(R^a)(R^b)N$- in which $R^a$ and $R^b$ each independently are hydrogen or alkyl or together with the nitrogen atom to which they are attached are a saturated 5- or 6-membered heterocyclic ring which can contain an additional nitrogen atom or an oxygen or sulphur atom or can carry an oxo group, whereby the sulphur atom can also be present in the form of a sulfinyl or sulfonyl group, or which can be substituted on one or two carbon atoms by alkyl, hydroxy, hydroxyalkyl or alkoxyalkoxy or on a second nitrogen atom which may be present by alkyl, benzyl, benzyloxycarbonyl, alkoxycarbonyl or hydroxyalkyl, and n is the integer zero.

13. A compound in accordance with claim 12 wherein said compound is S)-N-[(1S,2R,3S)-1-(cyclohexylmethyl)-3-cyclopropyl-2,3-dihydroxypropyl]-α-[(S)-α-[[[1-[[2-hydroxy-1-(hydroxymethyl)-1-methylethyl]carbamoyl]-1-methylethyl]sulfonyl]methyl]hydrocinnamamido]imidazole-4-propionamide.

14. A compound in accordance with claim 12 wherein said compound is (S)-α-[(R or S)-α-[[[1-[(2pyridylmethyl)carbamoyl]-1-methylethyl]sulfonyl]methyl]hydrocinnamamido]-N-[(1S ,2R,3S)-1-(cyclohexylmethyl)-3-cyclopropyl-2,3-dihydroxypropyl]imidazole-4-propionamide.

15. A compound in accordance with claim 12 wherein said compound is (S)-α-[(R or S)-α-[[[1-[bis(2-methoxyethyl)carbamoyl]-1-methylethyl]sulfonyl]methyl]hydrocinnamamido]-N-[(1S ,2R,3S)-1-(cyclohexylmethyl)-3-cyclopropyl-2,3-dihydroxypropyl]imidazole-4-propionamide.

16. A compound in accordance with claim 12 wherein said compound is (S or R)-N-[(1S,2R,3S)-1-(cyclohexylmethyl)-3-cyclopropyl-2,3-dihydroxypropyl]-α-[(S)-α-[[[1-methyl-1-[morpholinocarbonyl]ethyl]sulfonyl]methyl]hydrocinnamamido]-3-(thiazolyl-4-yl)propionamide.

17. Compounds in accordance with claim 12 wherein $R^1$ is cyclohexyl, phenyl, napthyl or thienyl, $R^3$ is hydrogen, hydroxy, $C_1$–$C_4$-alkyl, $C_1$–$C_4$-alkoxy, allyloxy, $C_1$–$C_4$-alkylthio, $C_1$–$C_4$alkylthiomethyl, $C_1$–$C_4$-alkoxycarbonyl, imidazol-4-ylmethyl, thiazol-4-ylmethyl or pyridylmethyl, $R^4$ is cyclohexyl, $R^5$ is cyclopropyl-, isopropyl or isobutyl, $R^6$ and $R^7$ are methyl and Y is the group $(R^a)(R^b)N$-.

18. Compounds in accordance with claim 17 wherein $R^1$ is phenyl, $R^3$ is imidazol-4-ylmethyl or 3-pyridylmethyl, $R^5$ is cyclopropyl and Y is pyrrolidinyl, piperidinyl, piperazinyl, morpholinyl, thiomorpholinyl, 2-hydroxy-methylpyrrolidinyl, 3-hydroxypyrrolidinyl, 3,4-dihydroxy-pyrrolidinyl, 4-hydroxypiperidinyl, 4-oxopiperidinyl, 3,5-dimethylmorpholinyl, 4,4-dioxothiomorpholinyl, 4-oxothiomorpholinyl or 2,6-dimethylmorpholinyl.

19. A compound in accordance with claim 18 wherein said compound is (S)-N-[(1S,2R,3S)-1-(cyclohexylmethyl)-3-cyclopropyl-2,3-dihydroxypropyl]-α-[(S)-α-[[[1-[(4-hydroxypiperidino)carbonyl]-1-methylethyl]sulfonyl]methyl]hydrocinnamamido]imidazole-4-propionamide.

20. Compounds in accordance with claim 18 wherein Y is morpholinyl.

21. A compound in accordance with claim 20 wherein said compound is (S)-N-[(1S,2R,3S)-1-(cyclohexylmethyl)-3-cyclopropyl-2,3-dihydroxypropyl]-α-[(S)-α-[[[1-(morpholinocarbonyl)-1-methylethyl]sulfonyl]methyl]hydrocinnamamido]imidazole-4-propionamide.

22. A compound in accordance with claim 20 wherein said compound is (S or R)-N-[(1S,2R,3S)-1-(cyclohexylmethyl)-3-cyclopropyl-2,3-dihydroxypropyl]-α-[(S)-α-[[[1-methyl-1-[morpholinocarbonyl]ethyl]sulfonyl]methyl]hydrocinnamamido]-3-(pyridin-3-yl)propionamide.

23. Compounds of the formula:

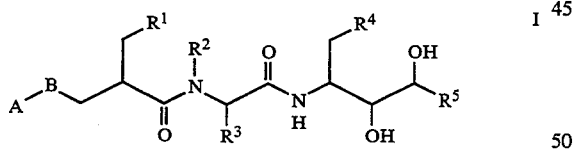

I wherein $R^1$ is cycloalkyl, phenyl, substituted phenyl, naphthyl, thienyl or pyridyl, $R^2$ is hydrogen, $R^3$ is hydrogen, hydroxy, alkyl, alkoxy, allyloxy, alkythio, alkylthiomethyl, alkoxycarbonyl, imidazol-1-ylmethyl, imidazol-4-ylmethyl, 2-aminoimidazol-4-ylmethyl, 5-iodoimidazol-4-ylmethyl, pyrazol-1-ylmethyl, thiazol-4-ylmethyl, thien-2-ylmethyl, furan-2-ylmethyl, pyridylmethyl or aminocarbonyl, $R^4$ is cycloalkyl or phenyl, $R^5$ is cycloalkyl or alkyl, B is sulfonyl,

(a)

24. A compound in accordance with claim 23 wherein said compound is (S)-α-[(R or S)-α-[[[1-[(1-b-enzyl-4-piperidinyl)carbamoyl]-1-methylethyl]sulfonyl]methyl]hydrocinnamamido]-N-[(1S,2R,3S)-1-(cyclohexylmethyl)-3-cyclopropyl-2,3-dihydroxypropyl]imidazole-4-propionamide.

25. Compounds of the formula:

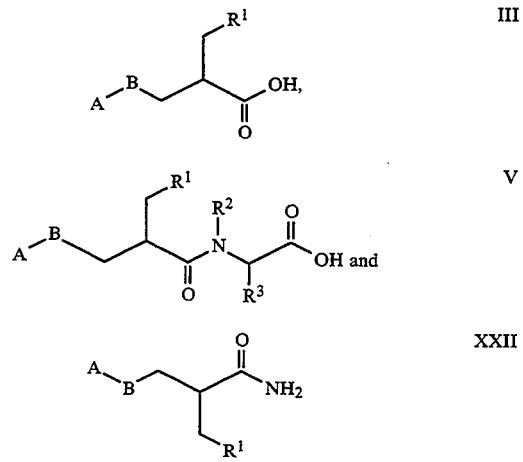

wherein A is the group

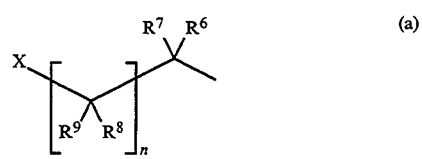

(a)

B is a sulphur atom or a sulfinyl or sulfonyl group, $R^1$ is cycloalkyl, phenyl, substituted phenyl, naphthyl, thienyl, pyridyl, quinolyl, isoquinolyl or benzyl, $R^2$ is hydrogen or methyl, $R^3$ is hydrogen, hydroxy, alkyl, alkoxy, alkenyloxy, alkylthio, alkylthioalkyl or alkoxycarbonyl, or imidazol-1-ylmethyl, imidazol-2-ylmethyl or imidazol-4-ylmethyl, each of which can be methylated on a carbon and/or nitrogen atom, 2-aminoimidazol-4-ylmethyl, 5-iodoimidazol-4-ylmethyl, pyrazol-1-ylmethyl, pyrazol-3-ylmethyl, thiazol-2-ylmethyl, thiazol-4-ylmethyl, thiazolyl-5-ylmethyl, 2-aminothiazol-4-ylmethyl, thienylmethyl, furanylmethyl, pyridylmethyl, aminocarbonyl, aminocarbonylalkyl or alkoxycarbonylalkyl, $R^6$, $R^7$ and $R^8$ each independently are hydrogen or alkyl, $R^9$ is hydrogen, alkyl, hydroxyalkyl, amino, alkoxycarbonylamino or benzyloxycarbonylamino, n is the integer zero or one and X is the group Y—CO— or, where n is the integer one, also the group Z—O—, wherein Y is cycloalkylamino, sulphoalkylamino, bisalkoxyalkylamino, or pyridylalkylamino or morpholinoalkylamino, each of which can be substituted at the amino group by alkyl; pyrazinylalkylamino, which can be substituted at the nitrogen atom and/or at the amino group by alkyl; 4-piperidinylalkylamino, which can be substituted at the nitrogen atom by alkyl, benzyl, benzyloxycarbonyl, alkoxycarbonyl or hydroxyalkyl an/or at the amino group by alkyl; alkoxycarbonylamino, hydroxyalkoxyalkylamino, hydroxyalkylamino, bishydroxyalkylamino, the group $(R^a)(R^b)N$- in which $R^a$ and $R^b$ each independently are hydrogen or alkyl or together with the nitrogen atom to which they are attached are a saturated 5- or 6-membered heterocyclic ring which can contain an additional nitrogen atom or an oxygen or sulphur atom as a further hetero atom or can carry an oxo group, whereby the sulphur atom can also be present in the form of a sulfinyl or sulfonyl group, or which can be substituted on one or two carbon atoms by alkyl, hydroxy, hydroxyalkyl or alkoxyalkoxy or on a second nitrogen atom which may be present by alkyl, benzyl, benzyloxycarbonyl, alkoxycarbonyl or hydroxyalkyl or in which the optionally present second nitrogen atom can carry an oxygen atom, alkoxyalkoxyalkoxy, cycloalkylalkoxy, 1,3-dimethyldioxolan-2-ylalkoxy, the group $(R^a)(R^b)$N-alkoxy, the residue of a natural aminodesoxy sugar or, where $R^9$ is different from hydrogen or alkyl, also alkoxy and Z is $C_5$-$C_{17}$-alkylcarbonyl, benzoyl, alkoxyalkylcarbonyl, cycloalkylcarbonyl, aminoalkylcarbonyl which can be substituted at the nitrogen atom by alkoxycarbonyl or benzyloxycarbonyl, alkylaminocarbonyl, phenylaminocarbonyl or, where $R^9$ is different from hydrogen or alkyl, also hydrogen.

26. A pharmaceutical composition for the control or prevention of high blood pressure and cardiac insufficiency, containing a compound in accordance with claim 1 and a therapeutically inert excipient.

* * * * *